(12) United States Patent
Kriesel et al.

(10) Patent No.: US 6,200,293 B1
(45) Date of Patent: *Mar. 13, 2001

(54) FLUID DELIVERY DEVICE WITH TEMPERATURE CONTROLLED ENERGY SOURCE

(75) Inventors: Marshall S. Kriesel, Saint Paul, CA (US); Thomas N. Thompson, Richfield, MN (US)

(73) Assignee: Science Incorporated, Bloomington, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/489,426

(22) Filed: Jan. 21, 2000

Related U.S. Application Data

(60) Continuation-in-part of application No. 09/387,447, filed on Sep. 1, 1999, which is a division of application No. 08/919,147, filed on Aug. 27, 1997, now Pat. No. 5,961,492.

(51) Int. Cl.[7] .................................................. A61M 37/00
(52) U.S. Cl. ................... 604/132; 604/153; 128/DIG. 12
(58) Field of Search .................. 604/890.1, 31, 604/81, 113, 119, 132, 142, 145, 151, 153, 185, 257, 259; 128/DIG. 1, DIG. 12; 222/94–96

(56) References Cited

U.S. PATENT DOCUMENTS

| | | | |
|---|---|---|---|
| 4,732,930 | * 3/1988 | Tanaka et al. | 524/742 |
| 5,263,323 | * 11/1993 | Maus et al. | 604/67 X |
| 5,368,570 | * 11/1994 | Thompson et al. | 604/132 X |
| 5,403,893 | * 4/1995 | Tanaka et al. | 525/218 |
| 5,505,706 | * 4/1996 | Maus et al. | 604/132 X |
| 5,693,108 | * 12/1997 | Kriesel et al. | 604/132 |

* cited by examiner

*Primary Examiner*—Anhtuan T. Nguyen
(74) *Attorney, Agent, or Firm*—James E. Brunton

(57) ABSTRACT

A fluid delivery apparatus for infusing medicinal fluids into a patient which is of a compact, low profile, laminate construction. The apparatus embodies a novel thermal expanding polymer material which uniquely functions as an internal energy source for expelling the medicinal fluids from the device. The apparatus can be used for subdermal, intradermal and intramuscular infusion of fluids and in one form of the invention, includes a novel delivery cannula having a body portion disposed within a circuitous channel formed within the base superstructure of the apparatus and a pierceable portion which extends outwardly from the base of the apparatus. By constructing the cannula in a circuitous configuration and dynamically connecting it to the base assembly, movement of the cannula relative to the base assembly is permitted thereby minimizing needle related tissue necrosis. The heat-expandable mass which is heated by the patient's body temperature in a manner to controllably expel fluid from the device uniquely functions to provide a conformable ullage within the reservoir of the device which will effectively avoid extended flow delivery rate trail-off at the end of the fluid delivery period. Further, the heat expandable mass can be specifically tailored to provide precise, predictable protocol delivery of the medicinal agent stored within the reservoir of the device.

25 Claims, 42 Drawing Sheets

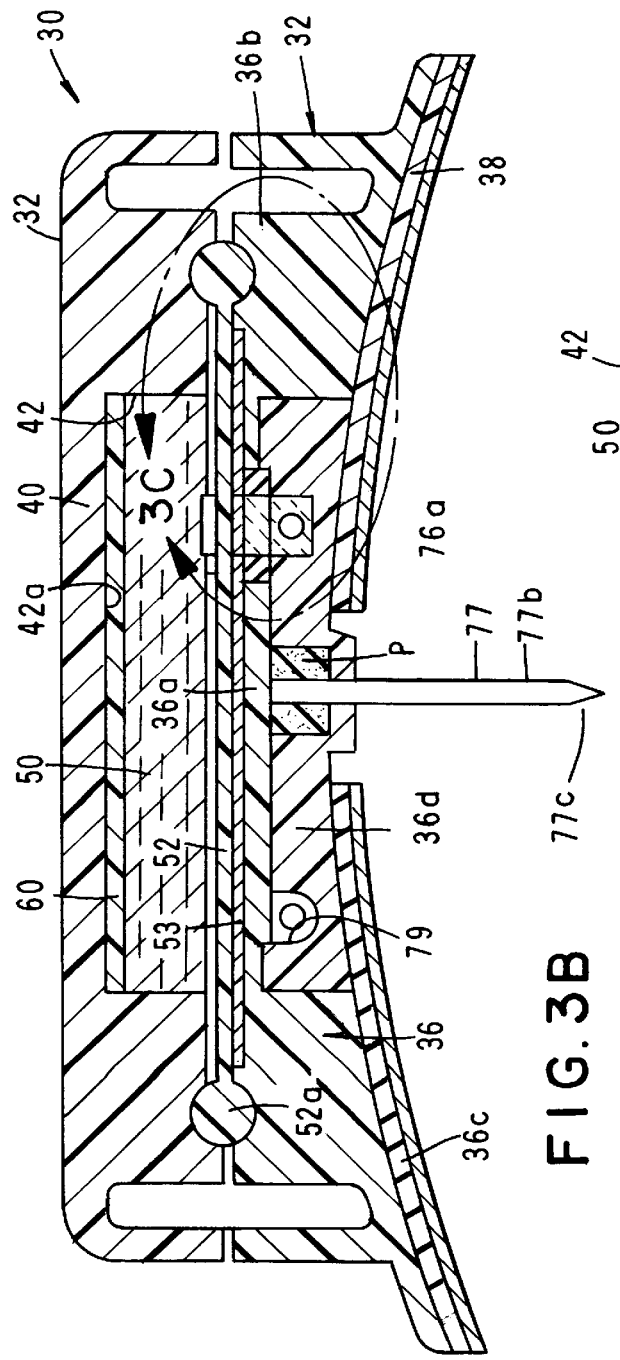
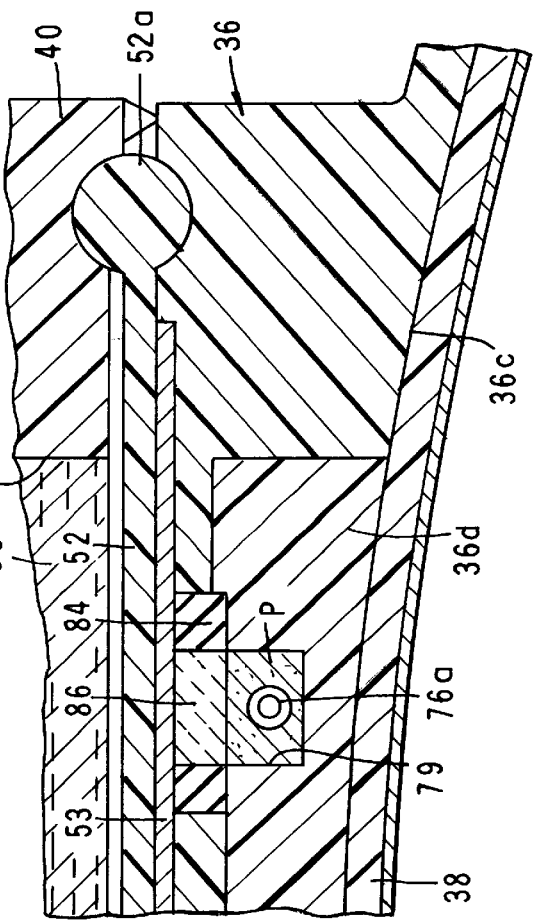
FIG. 3B
FIG. 3C

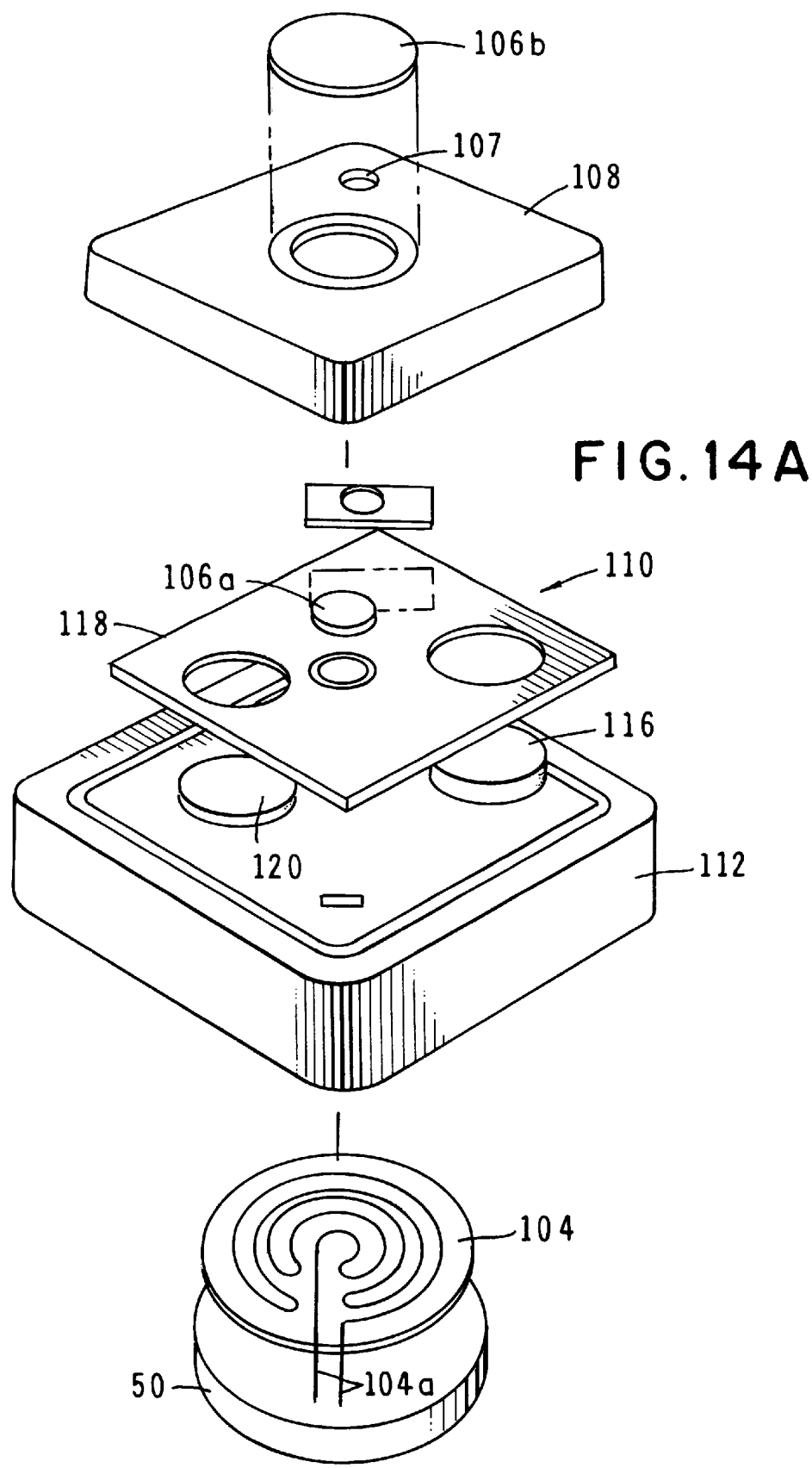

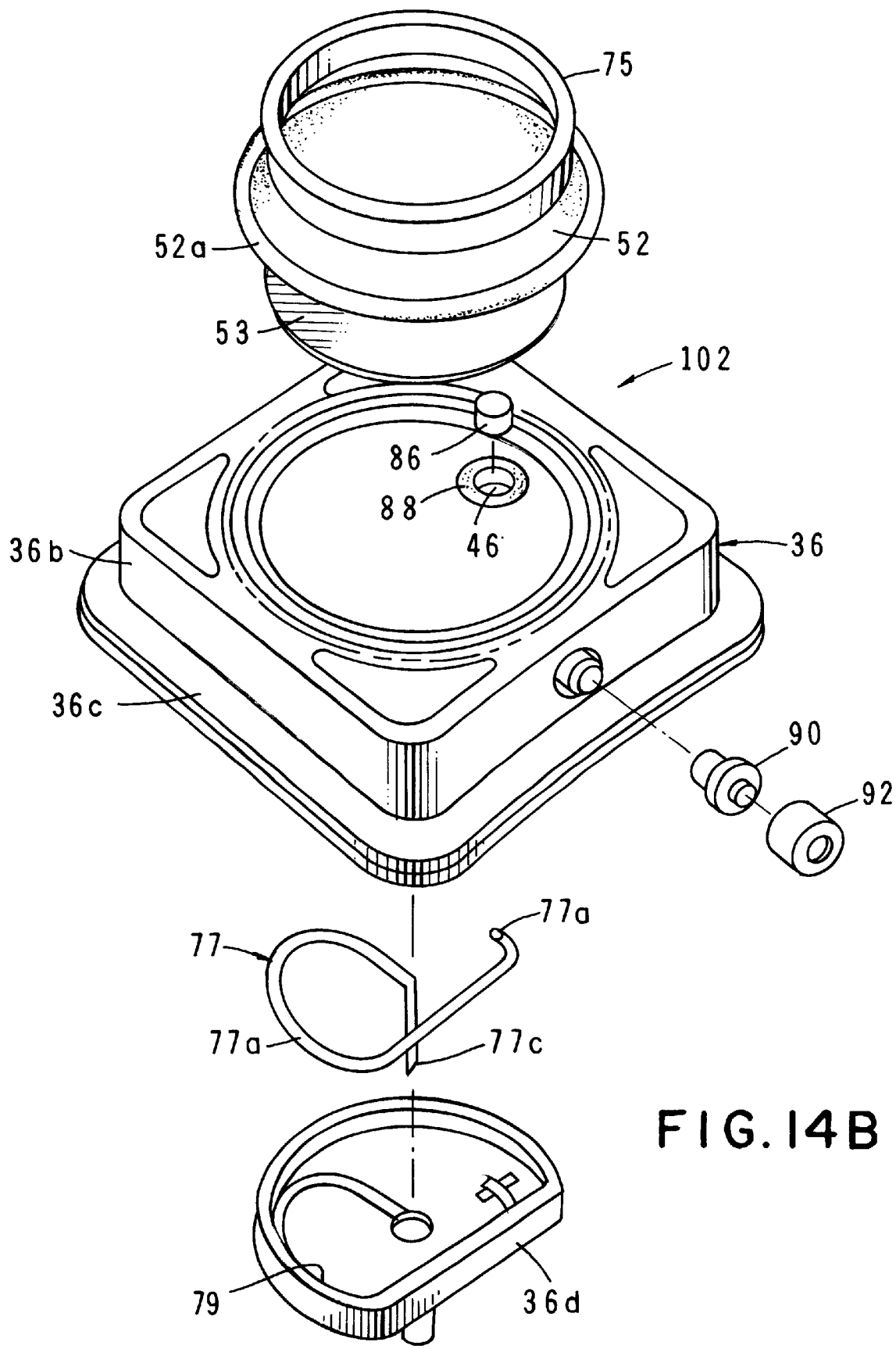

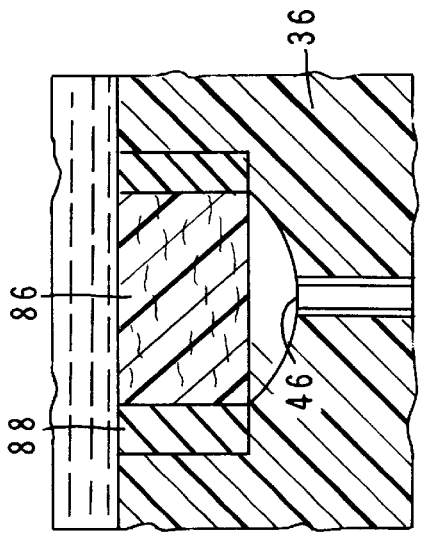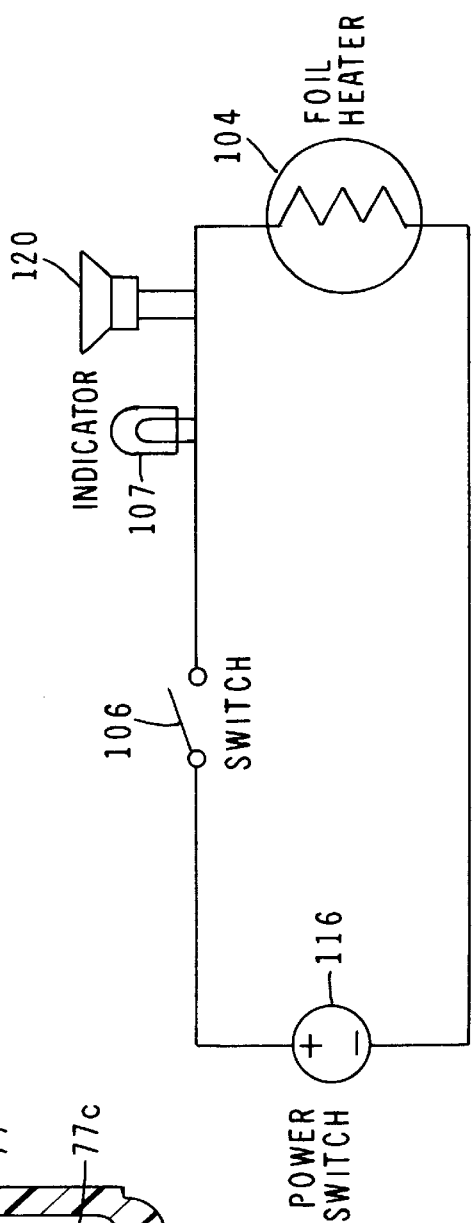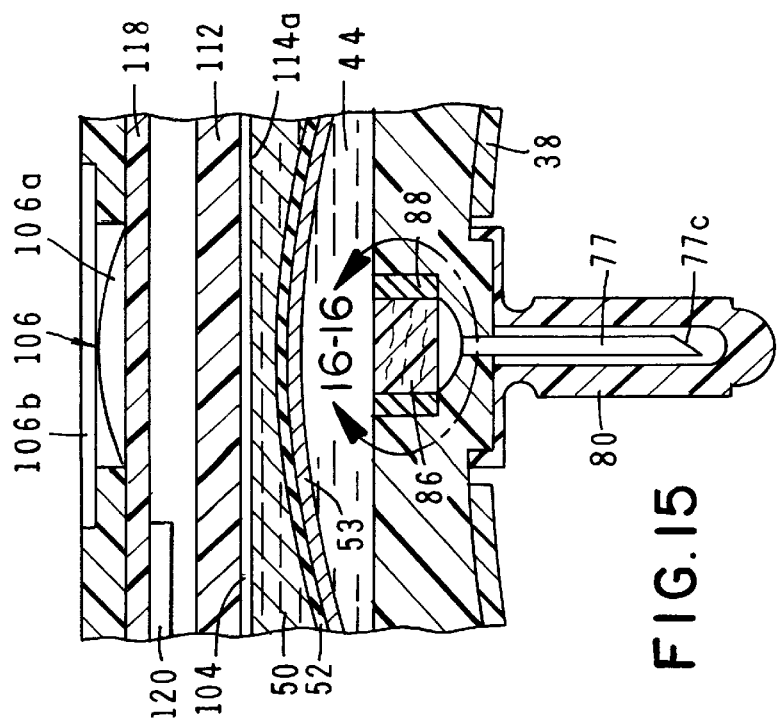

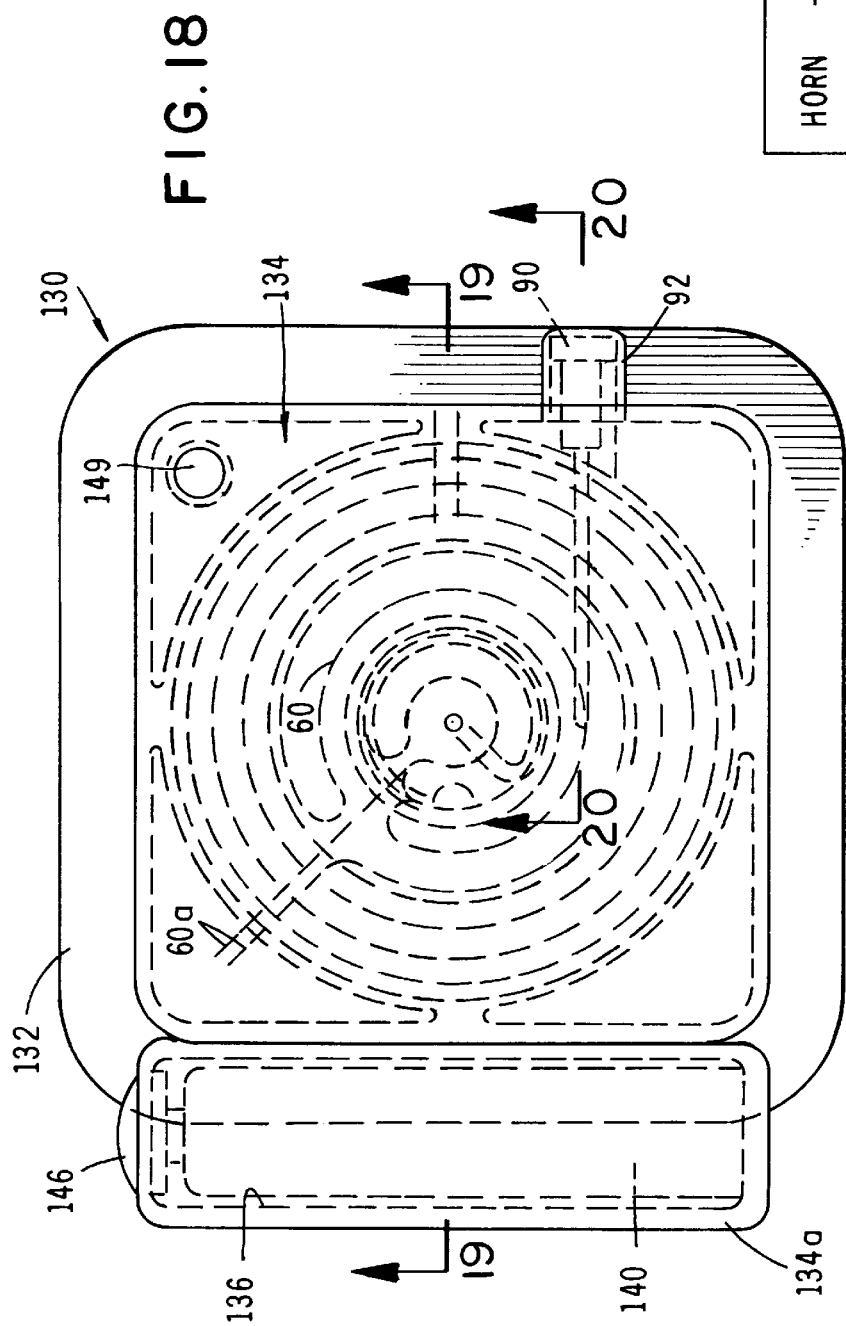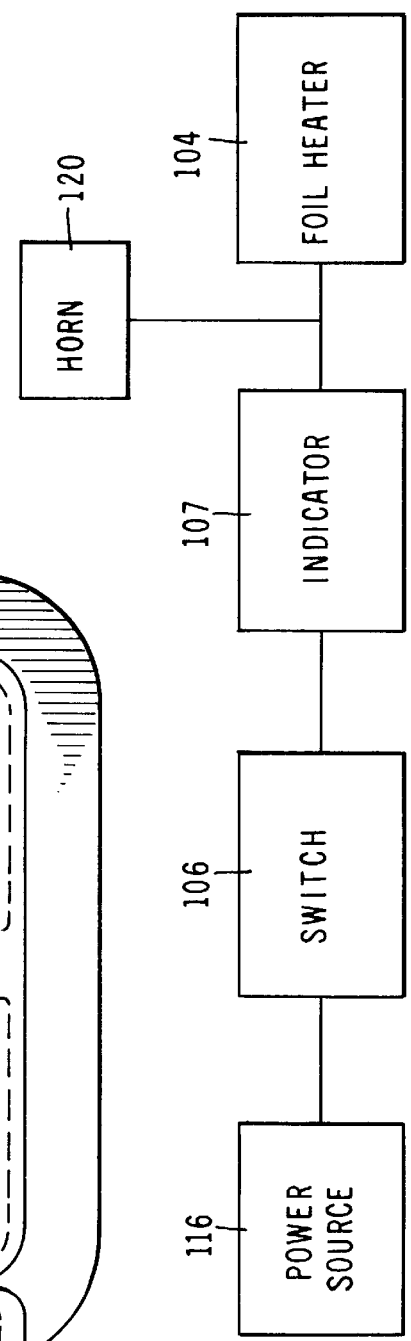

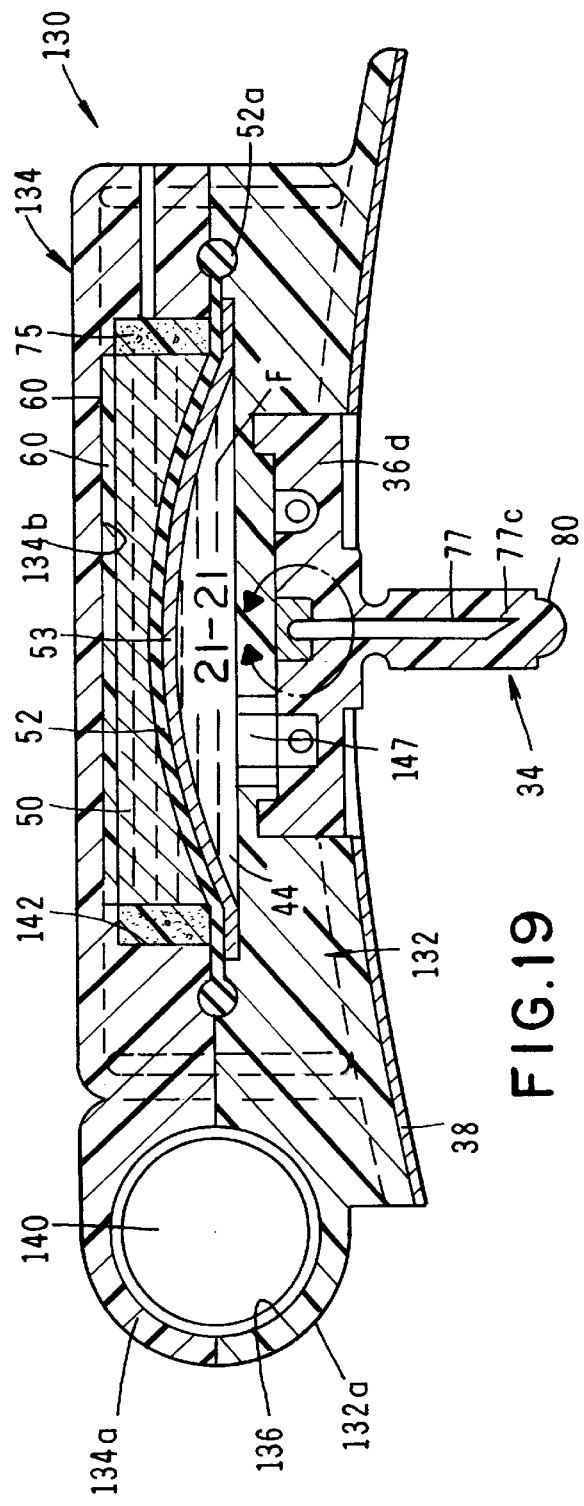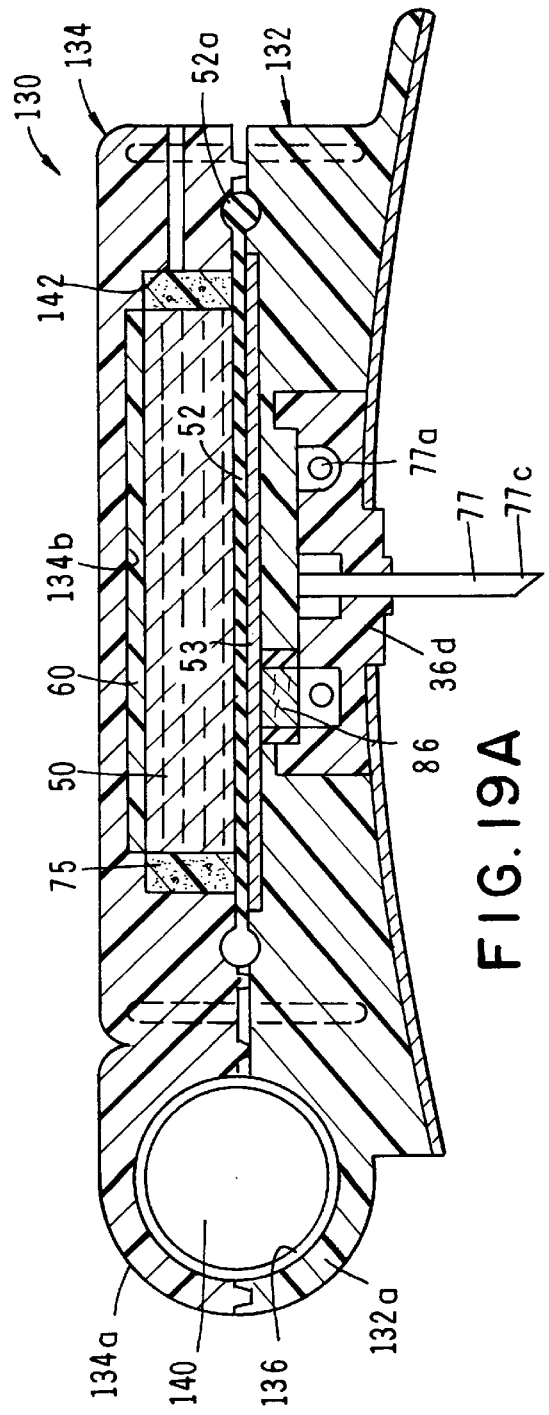

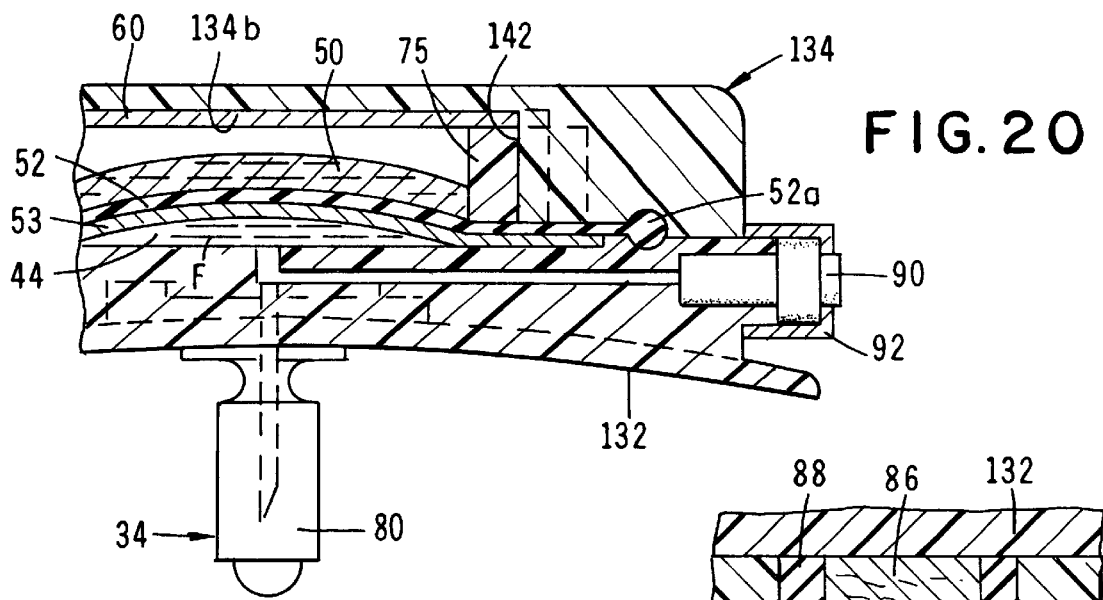
FIG. 20
FIG. 21
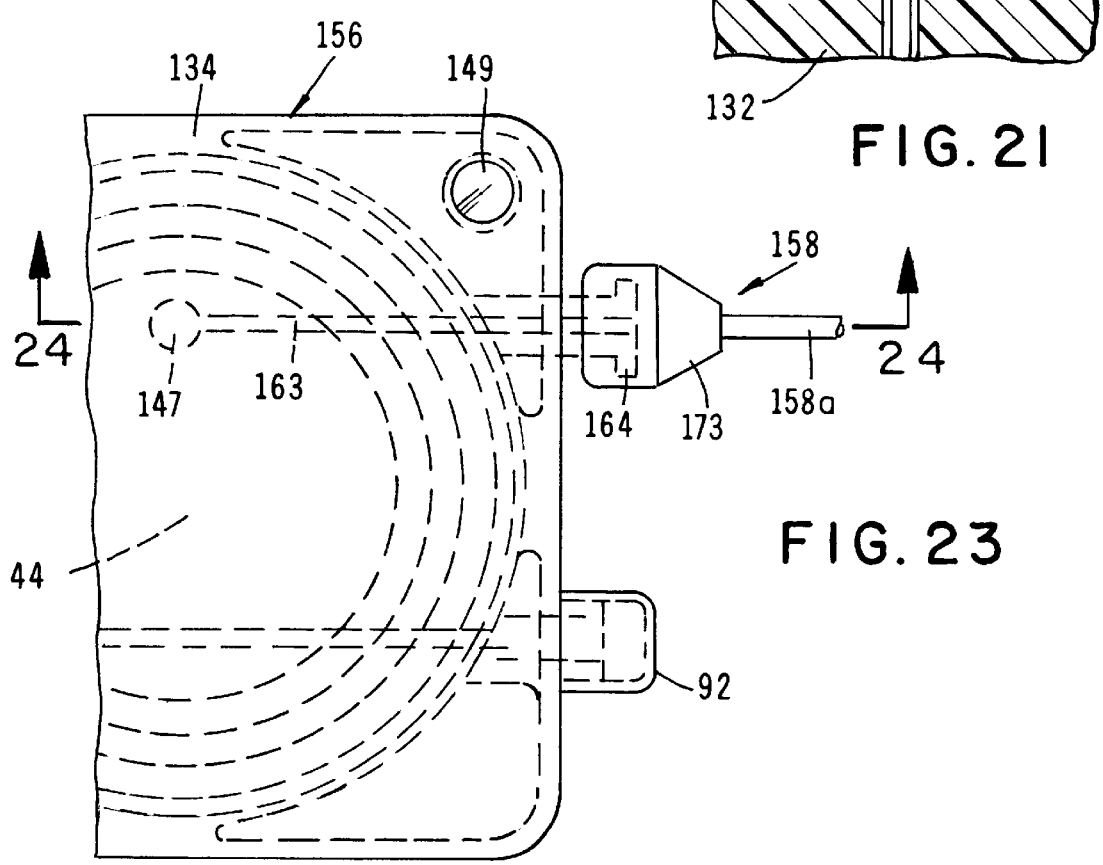
FIG. 23

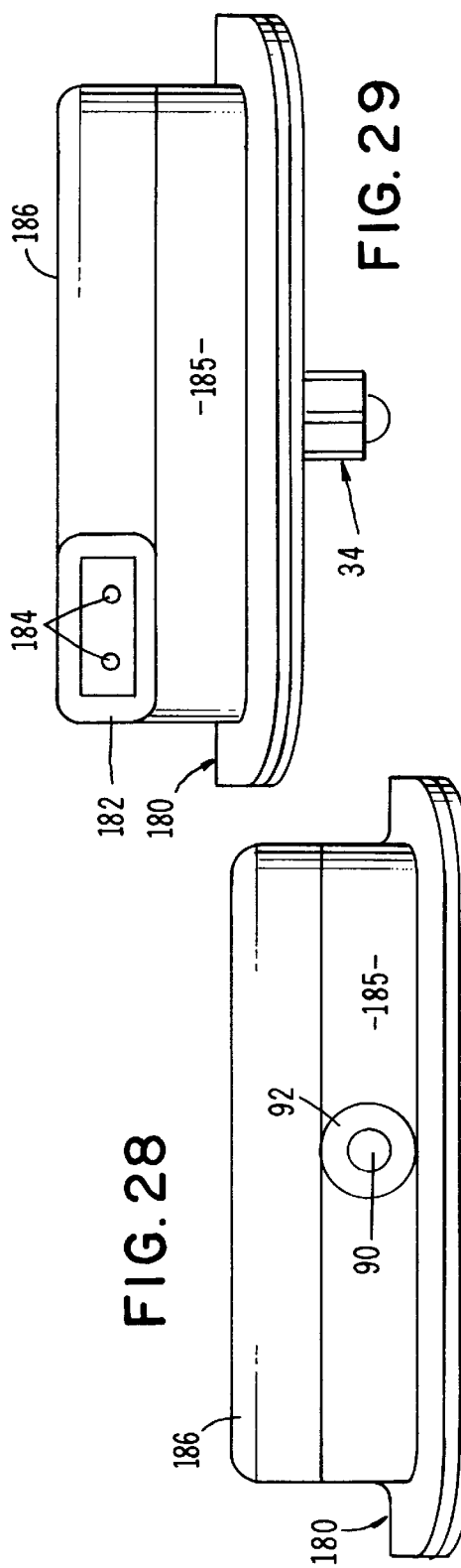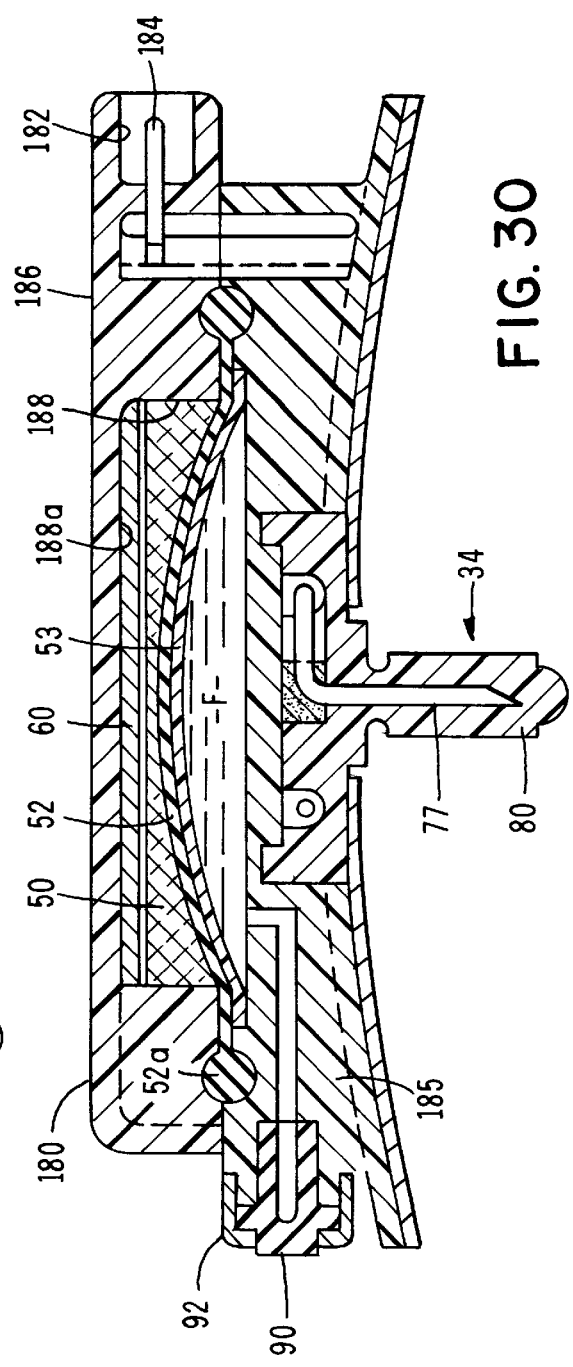

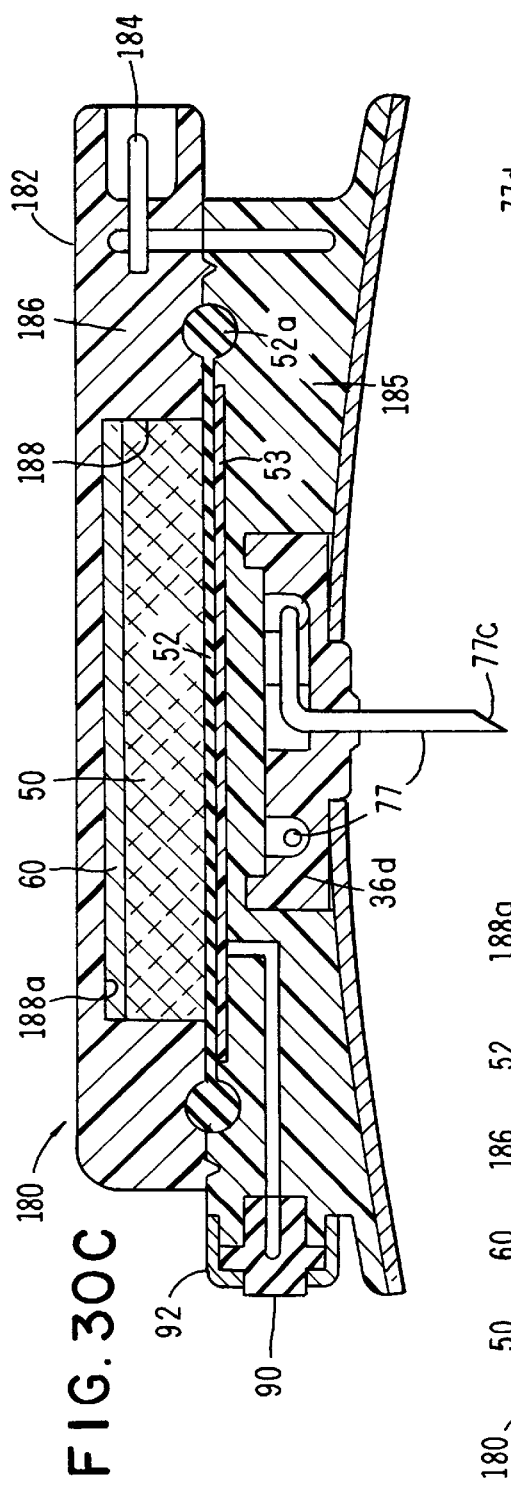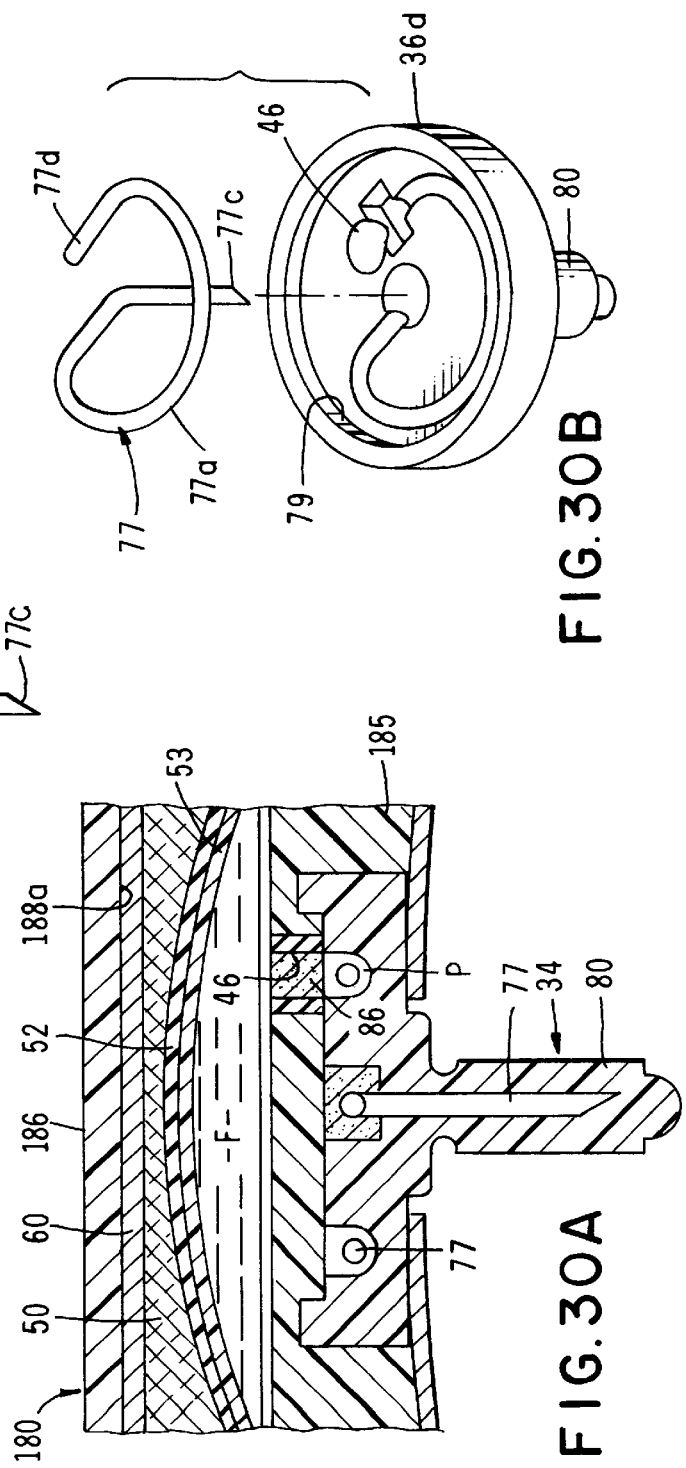
FIG.30C
FIG.30B
FIG.30A

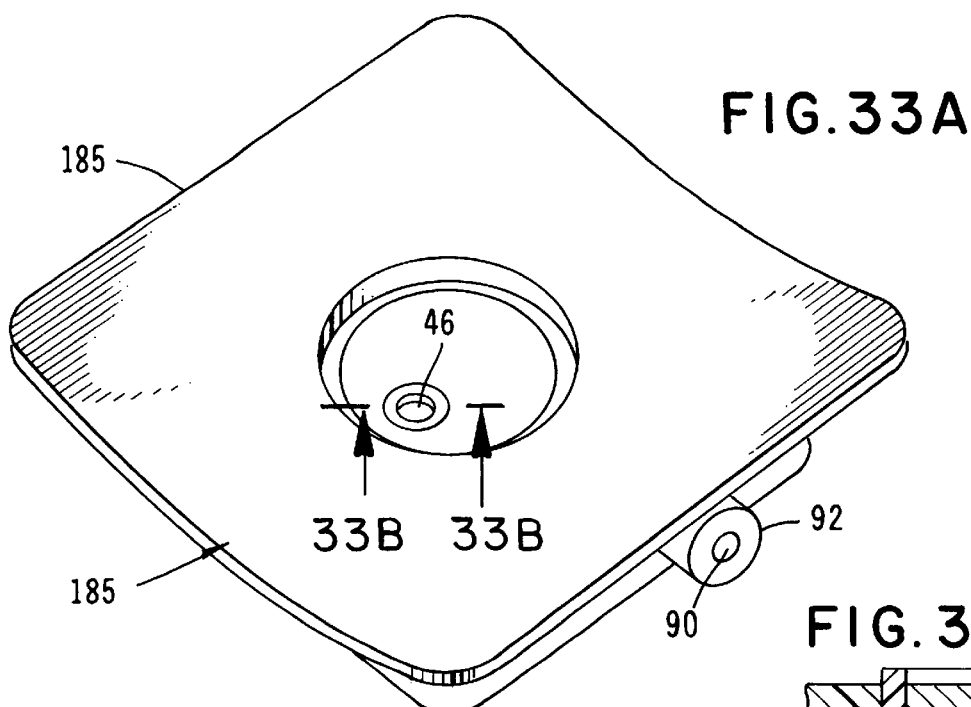
FIG. 33A
FIG. 33B
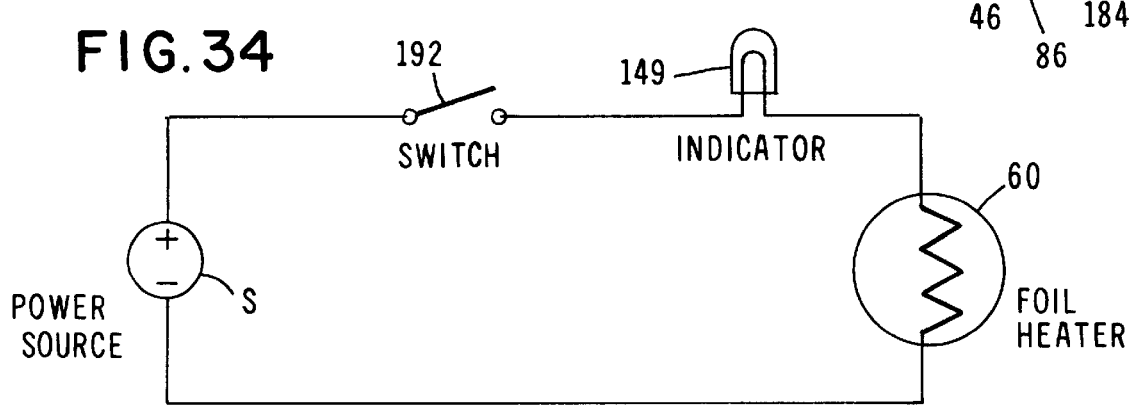
FIG. 34
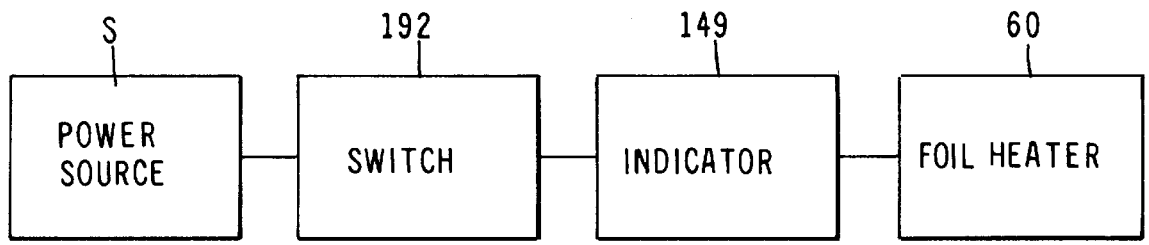
FIG. 34A

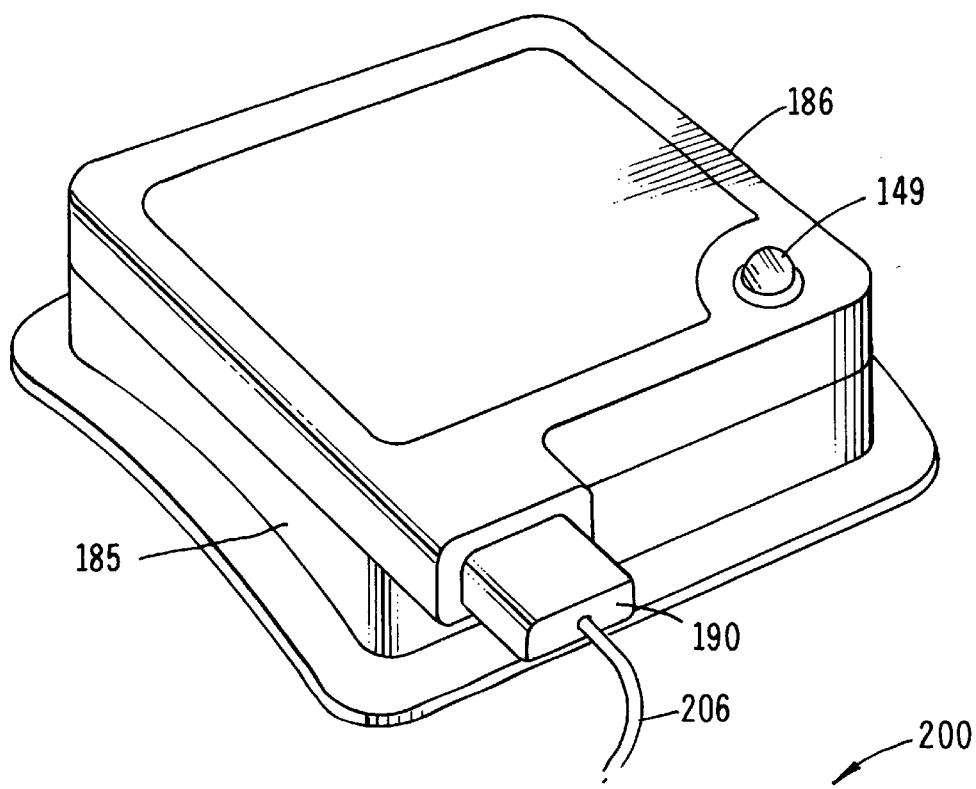
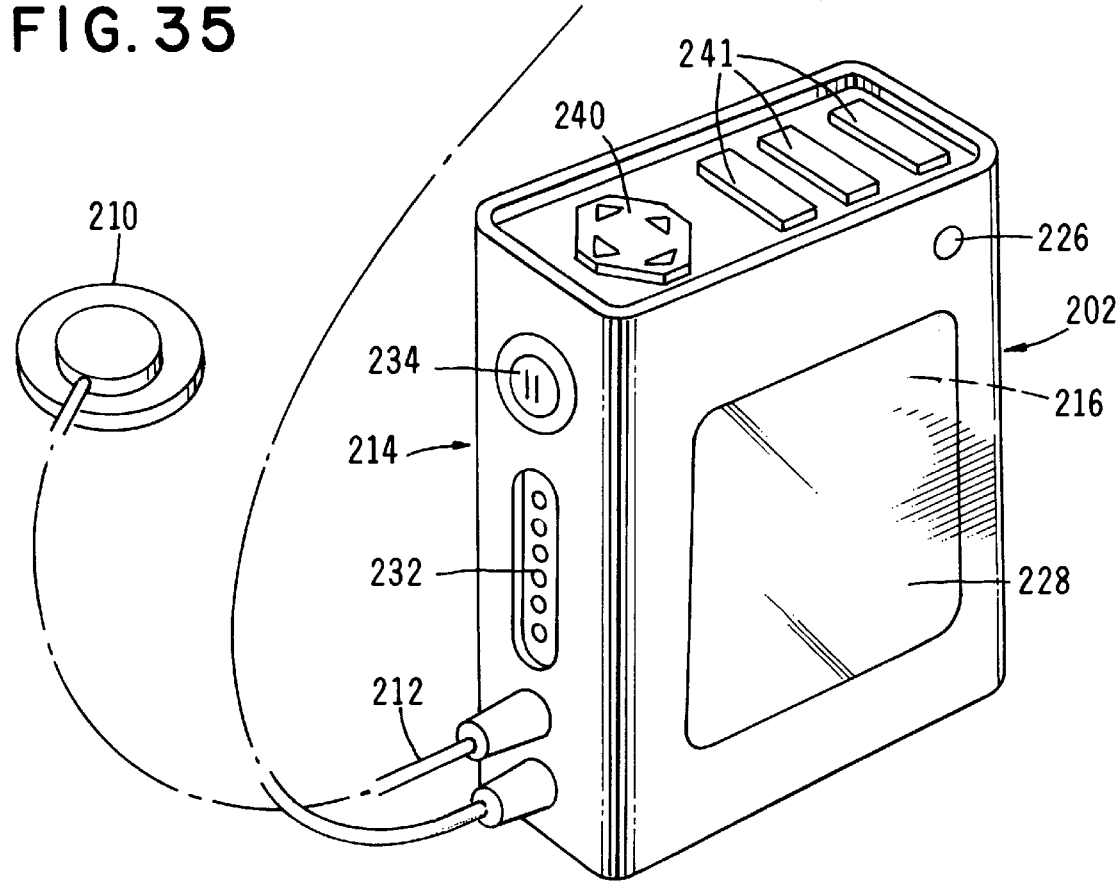
FIG. 35

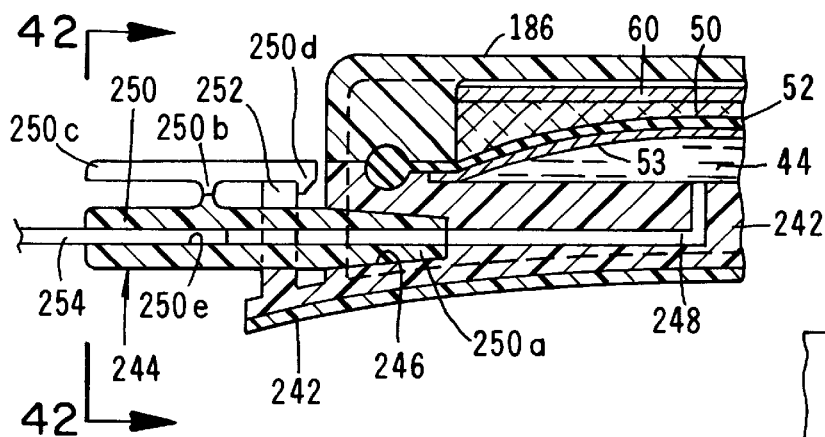
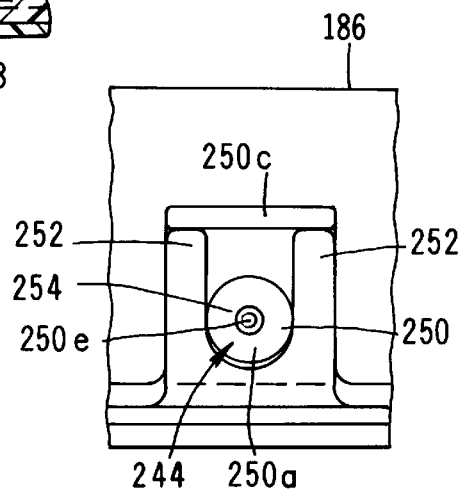
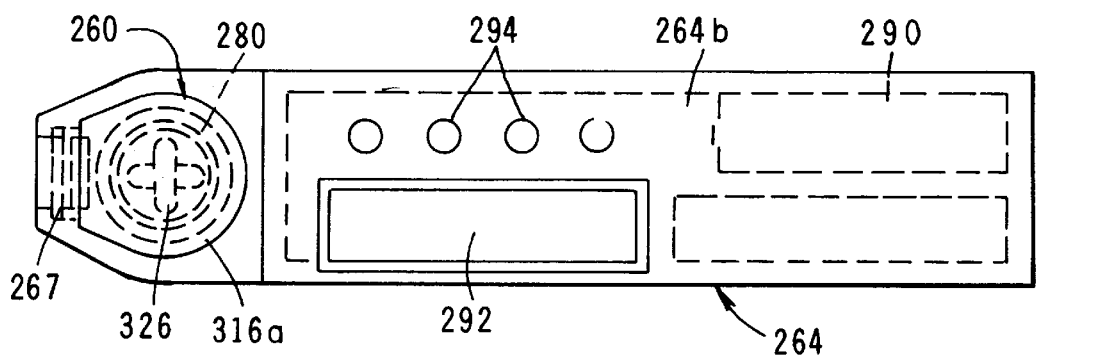
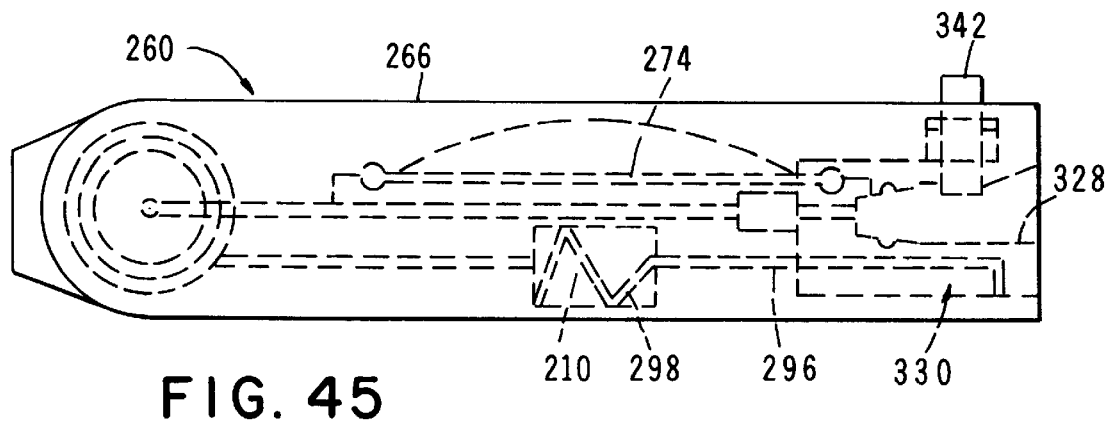

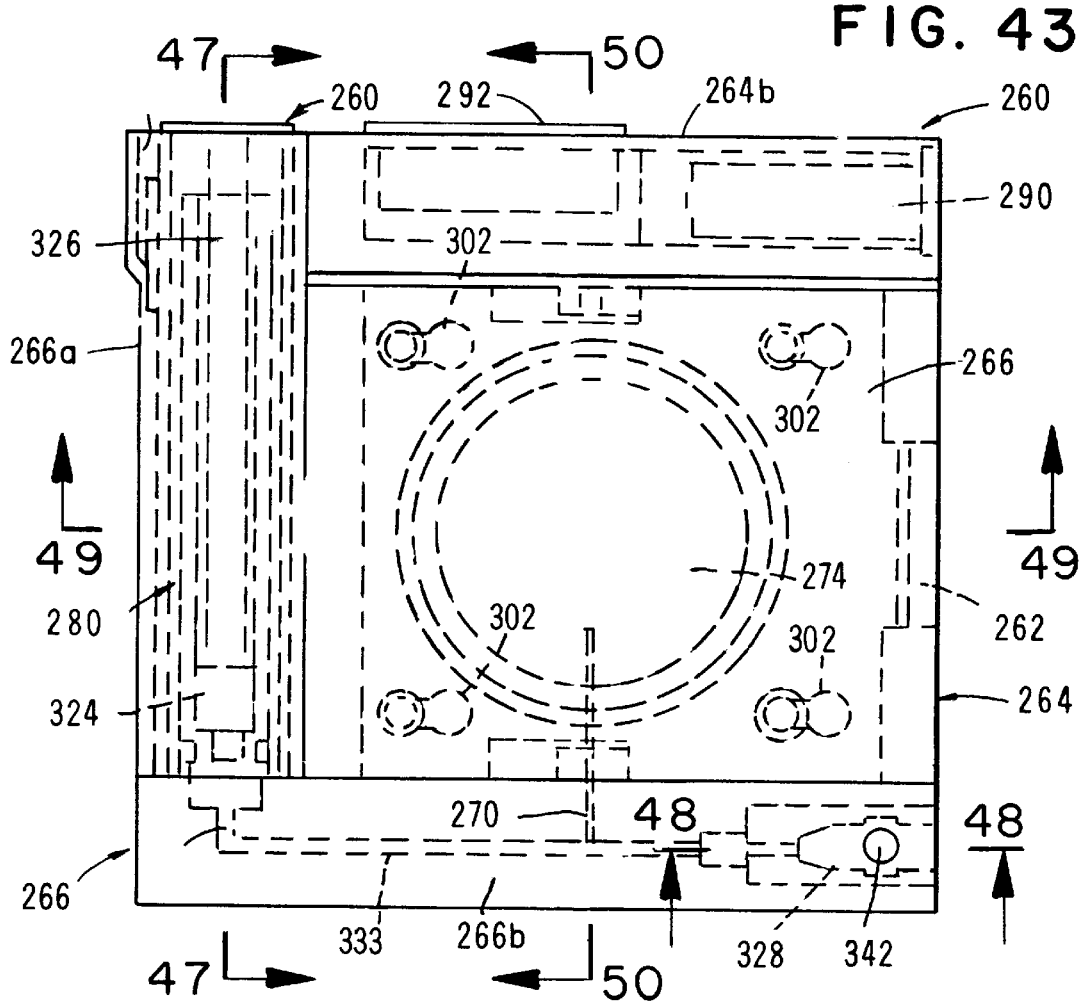
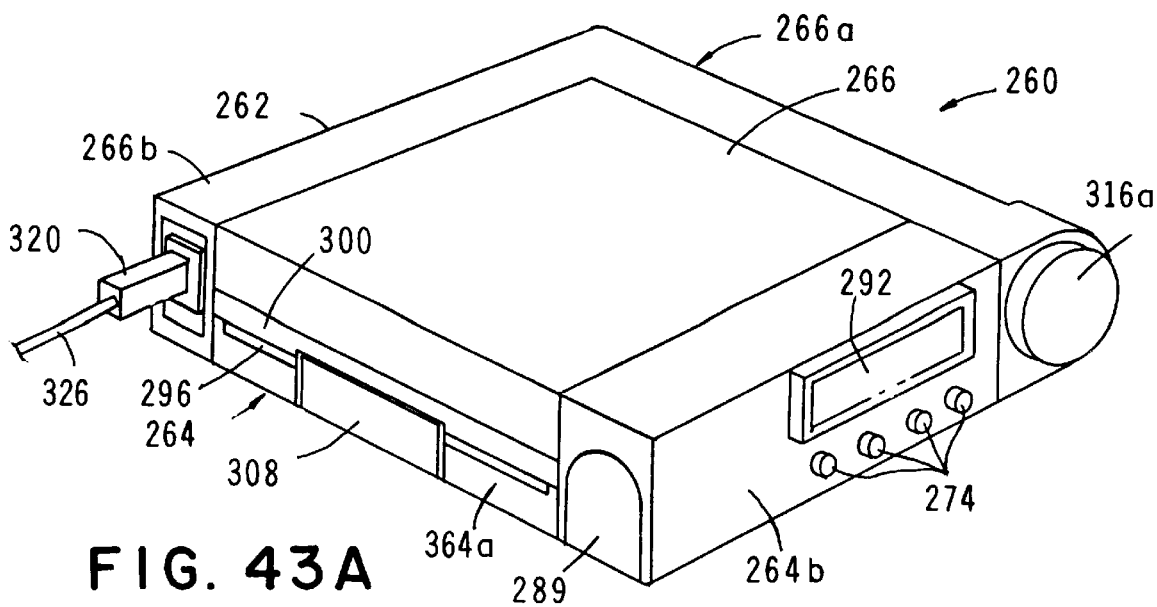
FIG. 43
FIG. 43A

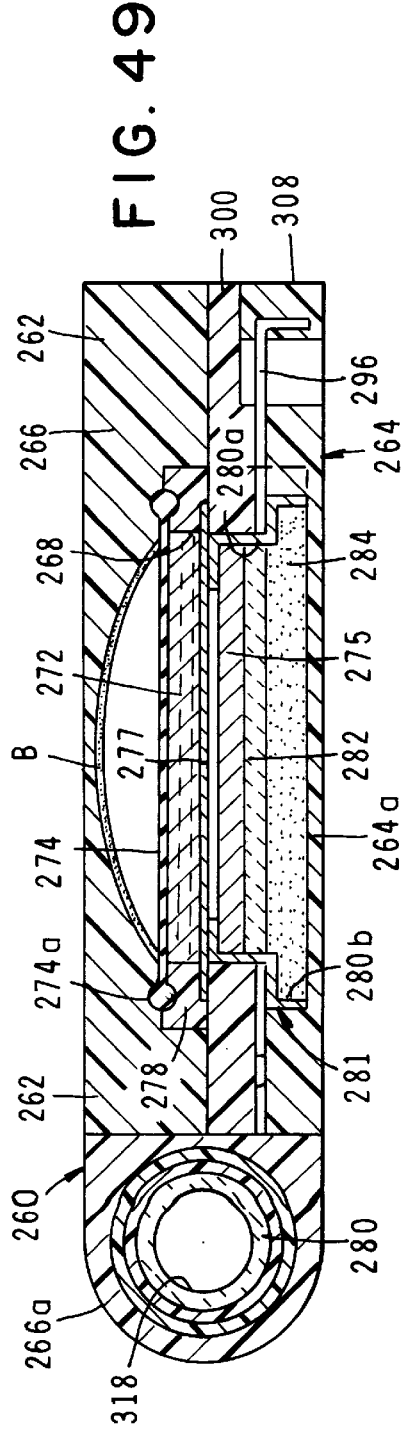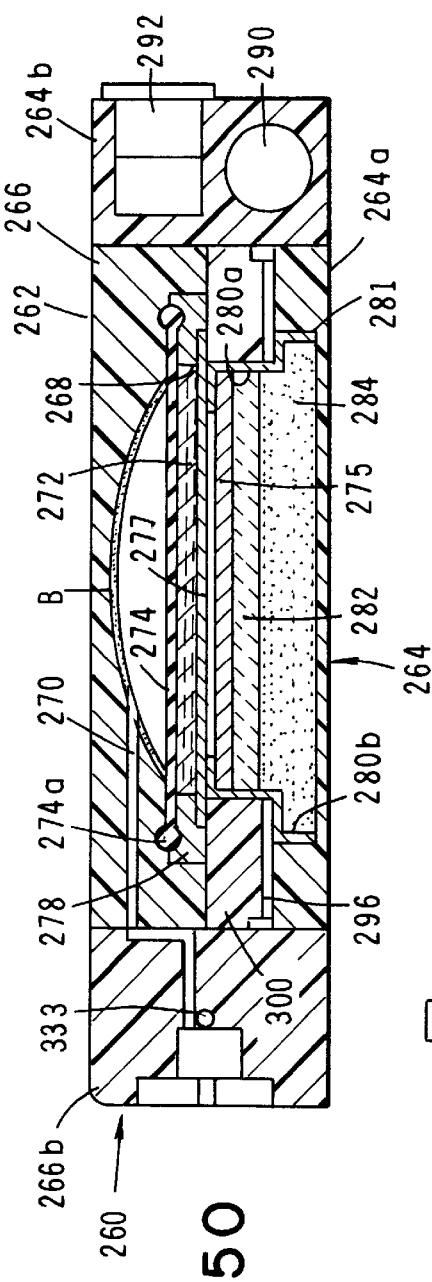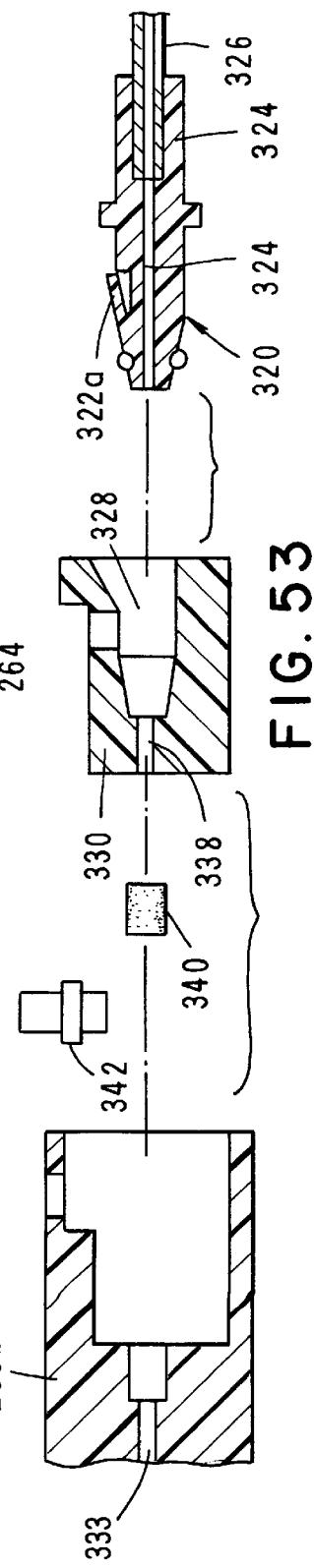

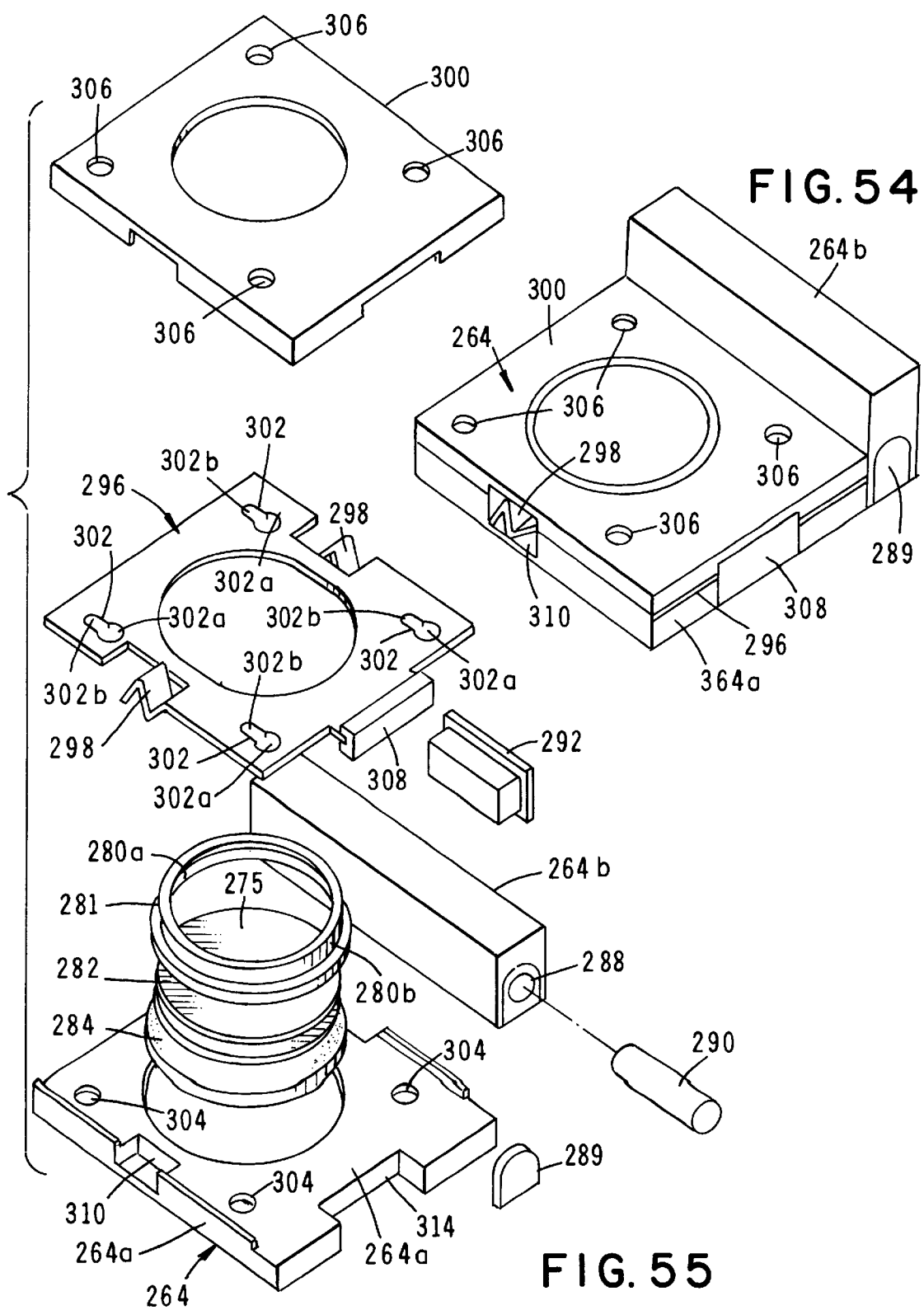

FLUID DELIVERY DEVICE WITH TEMPERATURE CONTROLLED ENERGY SOURCE

This is a Continuation-In-Part of co-pending application Ser. No. 09/387,447 filed Sep. 1, 1999, now allowed, which is a Divisional application of co-pending application Ser. No. 08/919,147 filed Aug. 27, 1997, now U.S. Pat. No. 5,961,492.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time.

2. Discussion of the Invention

The oral route is the most frequent route of drug administration. Oral administration is relatively easy for most patients and rarely causes physical discomfort. However, many medicinal agents require a parenteral route of administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug my mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow means coupled with electronic based controls and typically involve the use of intravenous administration sets and the familiar bottle or solution bag suspended above the patient. Such methods are cumbersome, imprecise and, generally non-ambulatory requiring bed confinement of the patient. Periodic monitoring of the apparatus by the nurse or doctor is required to detect malfunctions of the infusion apparatus.

Devices of the character from which liquid is expelled from a relatively thick-walled bladder by internal stresses within the distended bladder have also been suggested for infusion of medicaments. For example, such bladder, or "balloon" type devices, are described in U.S. Pat. No. 3,469,578, issued to Bierman and in U.S. Pat. No. 4,318,400, issued to Perry.

A family of highly unique fluid delivery devices has been developed by the present inventor. These novel devices make use of recently developed elastomeric films, expandable foams and similar materials, which, in cooperation with a base define a fluid chamber that contains the fluid to be dispensed. The elastomeric film membrane or the expandable member controllably forces fluid within the chamber into outlet fluid flow channels provided in the device. Elastomeric film membrane devices are described in detail in U.S. Pat. No. 5,205,820 issued to the present inventor. U.S. Pat. No. 5,468,226, also issued to the present inventor, describes various types of expandable cellular elastomers and elastomeric foams used as the energy source of the fluid delivery device for expelling fluid from various physical forms of the fluid delivery device. Because of the pertinence of U.S. Pat. Nos. 5,205,820 and 5,468,226, these patents are hereby incorporated herein by reference in their entirety as though fully set forth herein. Copending U.S. Application Ser. No. 08/541,030, filed Oct. 11, 1996 in which the present inventor is named as co-inventor, is also pertinent to one form of the apparatus of the invention which is described hereinafter. Accordingly, Ser. No. 08/541,030 is also hereby incorporated by reference as though fully set forth herein.

U.S. Ser. No. 08/919,147, now U.S. Pat. No. 5,961,492 is also incorporated by reference as though fully set forth herein.

The apparatus of the present invention, which takes various physical forms, makes use of novel temperature expansive material as an energy source. This family of devices can also be used with minimal professional assistance in an alternate health care environment, such as the home. By way of example, devices of the invention can be comfortably and conveniently removably affixed to the patient's body and can be used with or without remotely located infusion sets for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the embodiments of the present invention comprises an ambulatory fluid dispensing system which includes a relatively thin body attached rigid base assembly and a uniquely designed stored energy means which cooperates with the base assembly for controllably expelling fluid from the reservoir of the device. In this form of the invention, the stored energy means is provided in the form of a heat expandable gel, the nature of which will be described in greater detail hereinafter. In this particular form of the invention, a novel, remotely located subcutaneous infusion set can be quickly coupled to the base assembly to enable precise infusion of fluid to a patient upon stimulation of the expandable gel by the gel stimulation means of the invention.

Another embodiment of the invention comprises an ambulatory fluid dispensing system which includes a rigid base assembly and a uniquely designed stored energy means which cooperates with the base assembly for controllably expelling fluid from the reservoir of the device. In this latter form of the invention, the stored energy means is also provided in the form of an expandable gel and a remotely located subcutaneous infusion set can be quickly coupled to the base assembly to enable precise infusion of fluid to a patient upon stimulation of the expandable gel caused by operator energization of a battery powered heating element.

Alternatively, in other embodiments of the invention, infusion is accomplished by infusion means integrally formed with the base assembly.

In still other embodiments of the invention which also use a heat expandable gel as an energy source, medicinal fluids are delivered to the patient from the fluid dispenser via various types of infusion means. By way of example, such dispensers can accomplish parenteral administration of a beneficial agent by the subcutaneous, subdermal, intradermal, intramuscular or intravenous routes. Subcutaneous injection places the drug into the tissues between the skin and the muscle. Drugs administered in this manner are absorbed somewhat slowly. When the beneficial agent is administered subcutaneously, the needle can be inserted at a 45 degree angle or, in some cases, as with obese patients, at a 90 degree angle. A beneficial agent administered by the intravenous route is given directly into the blood by a needle inserted into a vein. In such instances, action occurs almost immediately. An intramuscular injection is the administration of a beneficial agent into a muscle. Agents given by this route are absorbed more rapidly than those given by the subcutaneous route. In addition, a larger volume (1–5 mL) can be given at one site. The sites for intramuscular administration are the deltoid muscle (upper arm), the ventrogluteal or dorsogluteal sites (hip), and the vastus lateralis (thigh). When giving a beneficial drug by the intramuscular route, the needle of the infusion means is preferably inserted at a 90 degree angle.

The primary thrust of the various inventions described herein is to provide novel expandable gel type fluid delivery systems which are compact, easy to use, relatively low profile and are eminently capable of meeting even the most stringent of fluid delivery tolerance requirements. In this regard, medical and pharmacological research continues to reveal the importance of the manner in which a medicinal agent is administered. For example, certain classes of pharmacological agents possess a very narrow dosage range of therapeutic effectiveness, in which case too small a dose will have no effect, while too great a dose can result in toxic reaction. In other instances, some forms of medication require an extended delivery time to achieve the utmost effectiveness of a medicinal therapeutic regimen.

SUMMARY OF THE INVENTION

It is an object of the present invention to provide a technically advanced, fluid delivery apparatus for infusing medicinal fluids into a patient which is of a compact, low profile, laminate construction. More particularly, it is an object of the invention to provide an apparatus of such a character which embodies a novel expanding polymer gel material which uniquely functions as an internal energy source for expelling the medicinal fluids from the device.

Another object of the invention is to provide an ambulatory fluid delivery apparatus which can conveniently be used for the precise infusion of various pharmaceutical fluids into an ambulatory patient at controlled rates over extended periods of time.

Another object of the invention is to provide an apparatus of the aforementioned character which is highly reliable and easy-to-use by lay persons in a non-hospital environment.

Another object of the invention is to provide an apparatus as described in the preceding paragraphs which can be used for subdermal, intradermal and intramuscular infusion of fluids. In this regard, in one form of the invention, the apparatus includes a novel and unique delivery cannula having a body portion disposed within a circuitous channel formed within the base superstructure of the apparatus and a pierceable portion which extends outwardly from the base of the apparatus. By constructing the cannula in a circuitous configuration and dynamically connecting it to the base assembly, movement of the cannula relative to the base assembly is permitted thereby minimizing needle related tissue necrosis.

Another object of the invention is to provide an apparatus which embodies as its stored energy source, a soft, pliable, semi-solid, heat-expandable mass which is heated either by the patient's body temperature or by an external stimulus in a manner to controllably expel fluid from the device.

Another object of the invention is to provide an apparatus as described in the preceding paragraph in which the heat expandable mass is specifically tailored to provide precise, predictable protocol delivery of the medicinal agent stored within the reservoir of the device.

Another object of the invention is to provide an apparatus of the class described which includes novel means for indicating the presence of fluid within the reservoir and for also indicating fluid flow from the reservoir.

A further object of the invention is to provide a low profile, fluid delivery low profile, body attaching fluid delivery device of laminate construction which can meet even the most stringent fluid delivery tolerance and flow signature requirements.

Another object of the invention is to provide an apparatus of the character described which is responsive to an external source of stimulation such as heat and radiation, and includes a three-dimensional polymer network which functions as a stored energy source that can be constructed from various types of polymeric conformable materials such as phase transition gels.

Another object of the invention is to provide stored energy sources of the character described in the preceding paragraph which comprise blends or laminate constructions of phase transition gels that will enable the achievement of multi-rate delivery protocols.

Another object of the invention is to provide an apparatus of the character described which includes a novel, combination filter and rate control assemblage disposed intermediate the fluid reservoir and the outlet port of the device or intermediate outlet port of the device and the infusion means.

Another object of the invention is to provide an apparatus of the character described which, due to its unique construction, can be manufactured inexpensively in large volume by automated machinery.

Other objects of the invention are set forth in U.S. Pat. Nos. 5,205,820 and 5,468,226, which patents are incorporated herein by reference. Still further objects of the invention will become apparent from the discussion which follows.

BRIEF DESCRIPTION OF THE DRAWINGS

FIG. 3B is an enlarged, cross-sectional view taken along lines 3B—3B of FIG. 1.

FIG. 3C is an enlarged, cross-sectional view of the area designated as 3C in FIG. 3B.

FIG. 14 is a generally perspective, exploded view of the apparatus shown in FIG. 10.

FIG. 15 is a fragmentary, cross-sectional view of the central portion of the device shown in FIG. 13.

FIG. 16 is an enlarged, cross-sectional view of the area designated in FIG. 15 as 16—16.

FIG. 17 is a generally schematic view of another form of the electrical circuitry of the invention.

FIG. 17A is a block diagram of the electrical circuitry shown in FIG. 17.

FIG. 18 is a top plan view of an alternate form of the fluid delivery apparatus of the invention.

FIG. 19 is a cross-sectional view taken along lines 19—19 of FIG. 18.

FIG. 19A is an enlarged, cross-sectional view similar to FIG. 19, but showing the heat expandable member expanded.

FIG. 20 is a cross-sectional view taken along lines 20—20 of FIG. 18.

FIG. 21 is an enlarged, cross-sectional view of the area designated in FIG. 19 as 21—21.

FIG. 23 is a fragmentary top plan view of still another form of the fluid delivery apparatus of the invention having a different type of infusion means.

FIG. 28 is a left side elevational view of the device shown in FIG. 27.

FIG. 29 is a right side elevational view of the device shown in FIG. 27.

FIG. 30 is a cross-sectional view taken along lines 30—30 of FIG. 27.

FIG. 30A is an enlarged, cross-sectional view taken along lines 30A—30A of FIG. 27.

FIG. 30B is a generally perspective, exploded view of the cannula assembly of the device shown in FIG. 30.

FIG. 30C is an enlarged, cross-sectional view similar to FIG. 30, but showing the heat expandable member expanded.

FIG. 33A is an enlarged generally perspective bottom view of the device shown in FIG. 33.

FIG. 33B is an enlarged, cross-sectional view taken along lines 33B—33B of FIG. 33A.

FIG. 34 is a generally schematic view of still another form of the electrical circuitry of the invention.

FIG. 34A is a block diagram of the electrical circuitry shown in FIG. 34.

FIG. 35 is a generally perspective view of still another embodiment of the invention which includes a novel controller component for controlling the infusion of beneficial agents to the patient and a novel sensor for sensing metabolic conditions of the patient.

FIG. 41 is a cross-sectional view taken along lines 41—41 of FIG. 40.

FIG. 42 is a view taken along lines 42—42 of FIG. 41.

FIG. 43 is a top plan view of yet another alternate form of the fluid delivery apparatus of the invention.

FIG. 43A is a generally perspective rear view of the device shown in FIG. 43.

FIG. 44 is rear view of the device shown in FIG. 43.

FIG. 45 is front view of the device shown in FIG. 43.

FIG. 49 is a cross-sectional view taken along lines 49—49 of FIG. 43.

FIG. 50 is a cross-sectional view taken along lines 50—50 of FIG. 43.

FIG. 53 is an exploded cross-sectional view of a portion of the apparatus shown in FIG. 48 along with a cross-sectional view of the mating delivery line quick disconnect assembly of the invention.

FIG. 54 is a generally perspective, top view of the electronics housing of the apparatus shown in FIG. 43.

FIG. 55 is a generally perspective, exploded view of the electronics housing shown in FIG. 54.

DESCRIPTION OF THE INVENTION

Figure 1:
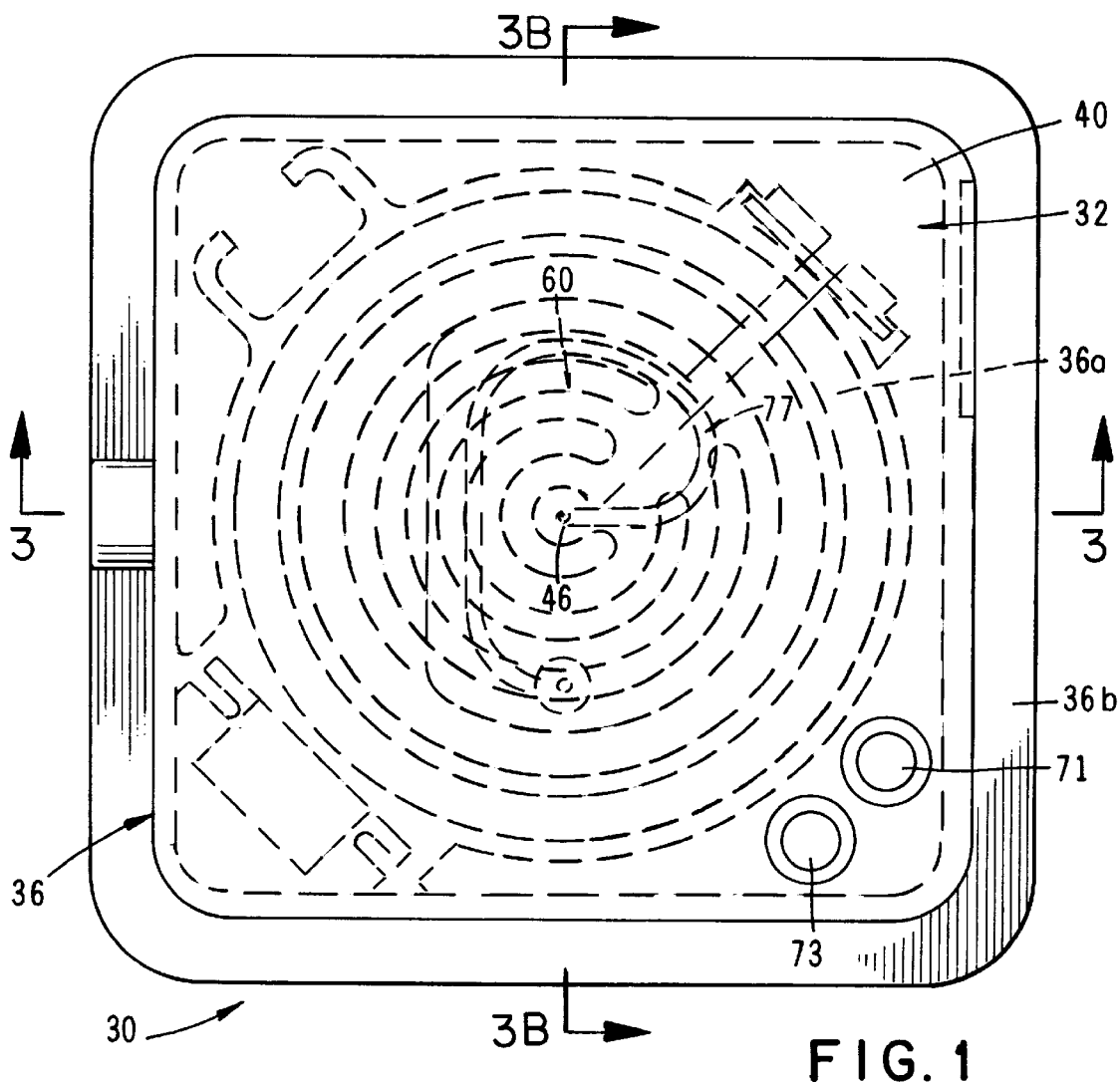
FIG. 1 is a top plan view of one form of the fluid delivery apparatus of the invention.
Figure 2:
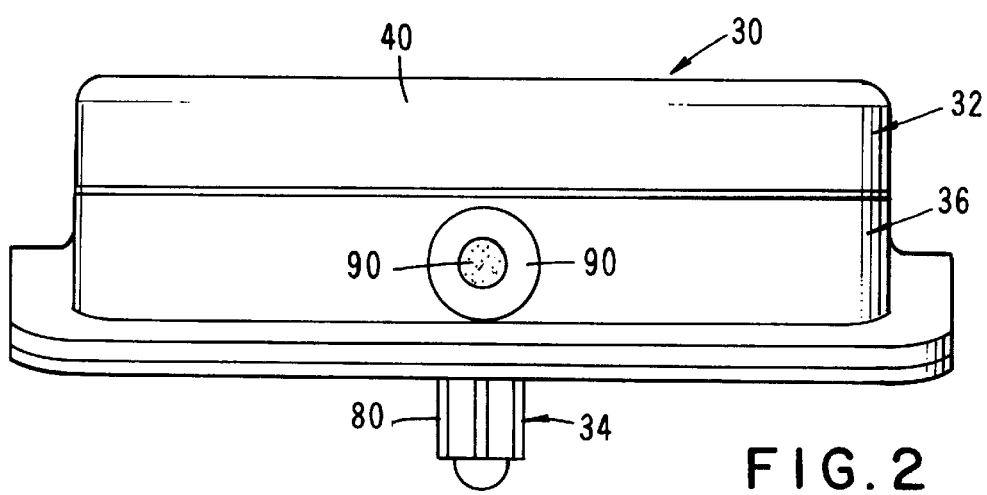
FIG. 2 is a side elevational view of the device shown in FIG. 1.

Referring to the drawings and particularly to FIGS. 1 through 9, one form of the apparatus of the invention for use in the infusion of medicinal fluids into a patient is there shown and generally designated by the numeral 30. As best seen by referring to FIG. 3, the embodiment of the invention here shown comprises a low-profile, fluid storage device 32 which includes an infusion means 34 for infusing the fluid stored in the device into the patient.

Figure 3:
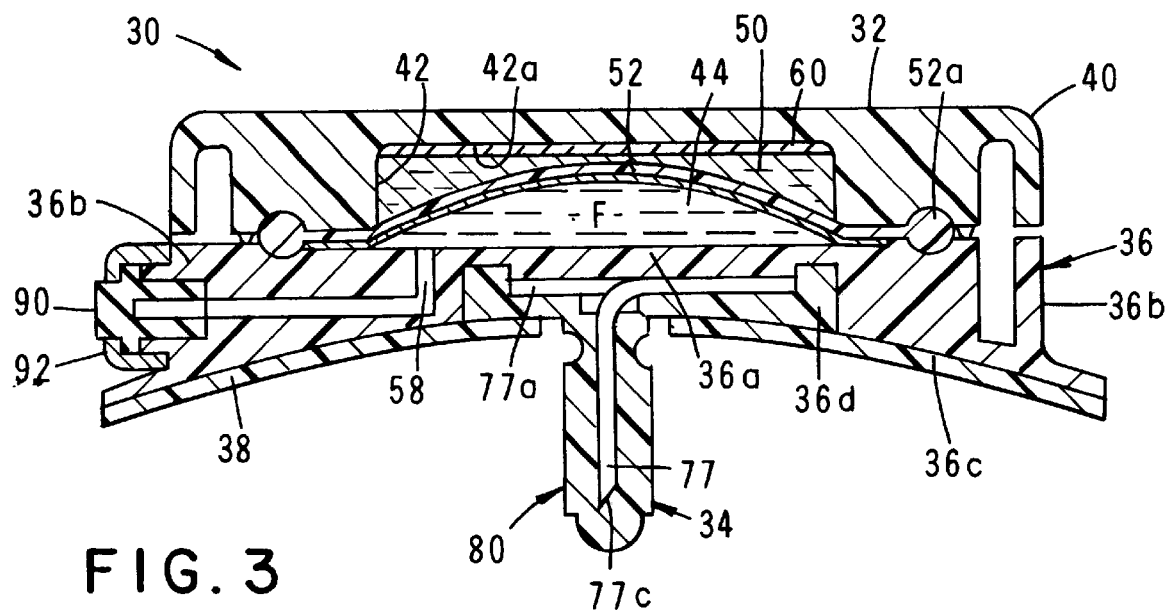
FIG. 3 is a cross-sectional view taken along lines 3—3 of FIG. 1.
Figure 3A:
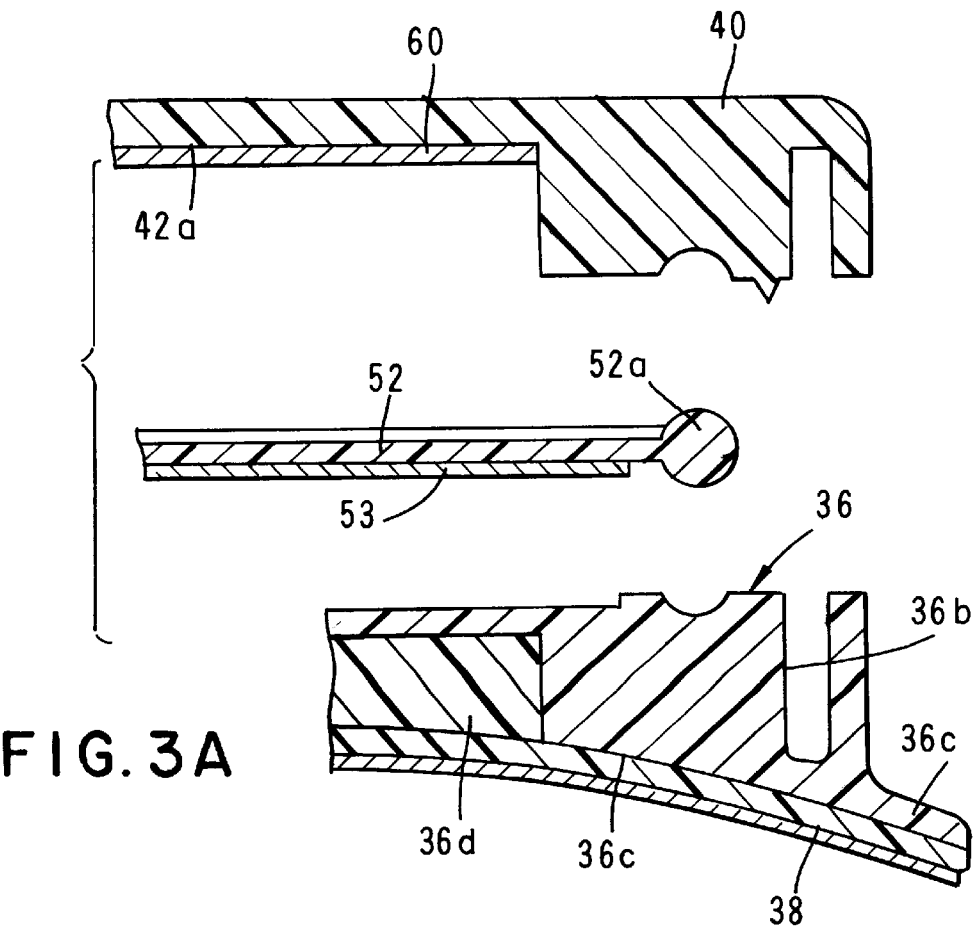
FIG. 3A is an enlarged, fragmentary, cross-sectional view of the right-hand portion of the device shown in FIG. 3 illustrating the manner of connection of the cover assembly to the base.
Figure 8:
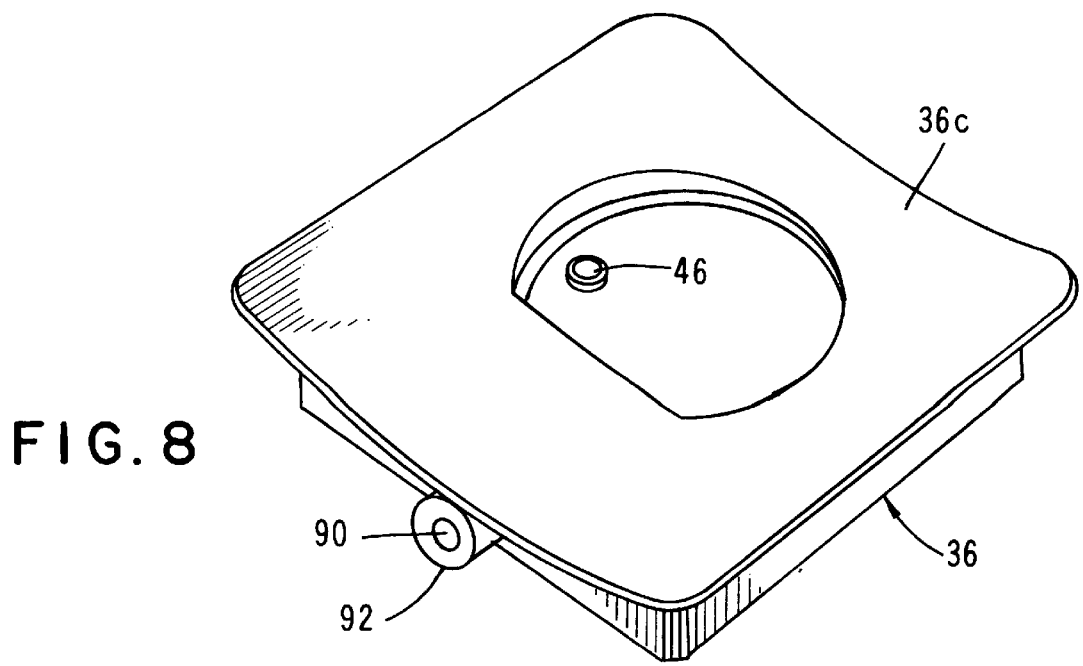
FIG. 8 is a generally perspective, bottom view of the base sub-assembly shown in FIG. 6.

Turning particularly to FIGS. 3 and 8, it can be seen that fluid storage device 32 includes a base assembly 36 having a central portion 36a and peripheral portion 36b circumscribing central portion 36a. Base assembly 36 is provided with a curved lower surface 36c which is engagable with the patient when the device is taped or otherwise removably affixed to the patient such as by a pad-like member 38 having adhesive on both sides of the member.

Figure 4:
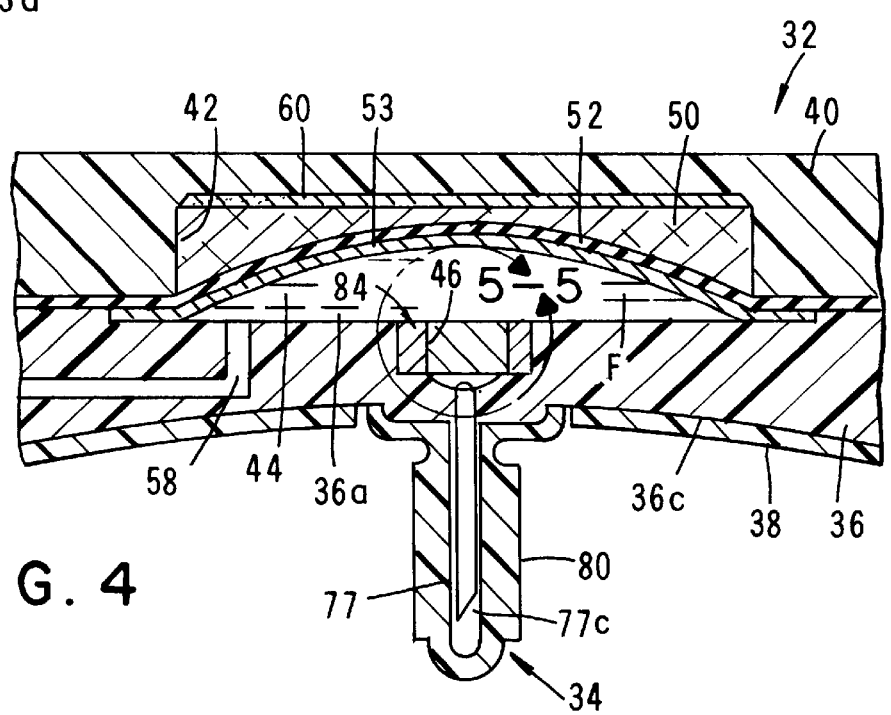
FIG. 4 is a fragmentary, cross-sectional view of the central portion of the device shown in FIG. 3.

Formed within a cover sub-assembly 40, which is connected to base 36, is a generally circular shaped chamber 42 (FIGS. 3 and 4), which houses the extremely important expandable means of the invention. This expandable means functions to cause the fluids contained within the sealed reservoir 44 of the device (FIG. 3) to flow outwardly through an outlet 46 formed in base 36 (FIG. 4). The heat-expandable means is here provided in the form of a thermal expandable polymer mass 50 which is disposed within chamber 42 in the manner best seen in FIG. 3.

Expandable mass 50 can take several forms, but a particularly attractive form for the delivery devices of the present invention, comprises a semisolid form such as a gel. Unlike liquids, which can offer no permanent resistance to change in shape and must be constrained within some type of container, the gel materials which make up the expandable means of the invention, are of a semisolid form which can advantageously be handled without external containment under ambient manufacturing conditions. By way of example, the gels comprise a cross-linked network of long polymer molecules with liquid molecules trapped within the network.

The various phase transition gels best suited for use in constructing the expandable means of the present invention are discussed in detail in incorporated by reference U.S. Pat. No. 5,961,492. Reference should be made to this patent for details concerning gels suitable for the present application which exhibit a large volume change at a given phase-transition condition and which can be made to respond to various types of external stimuli.

Figure 22A:
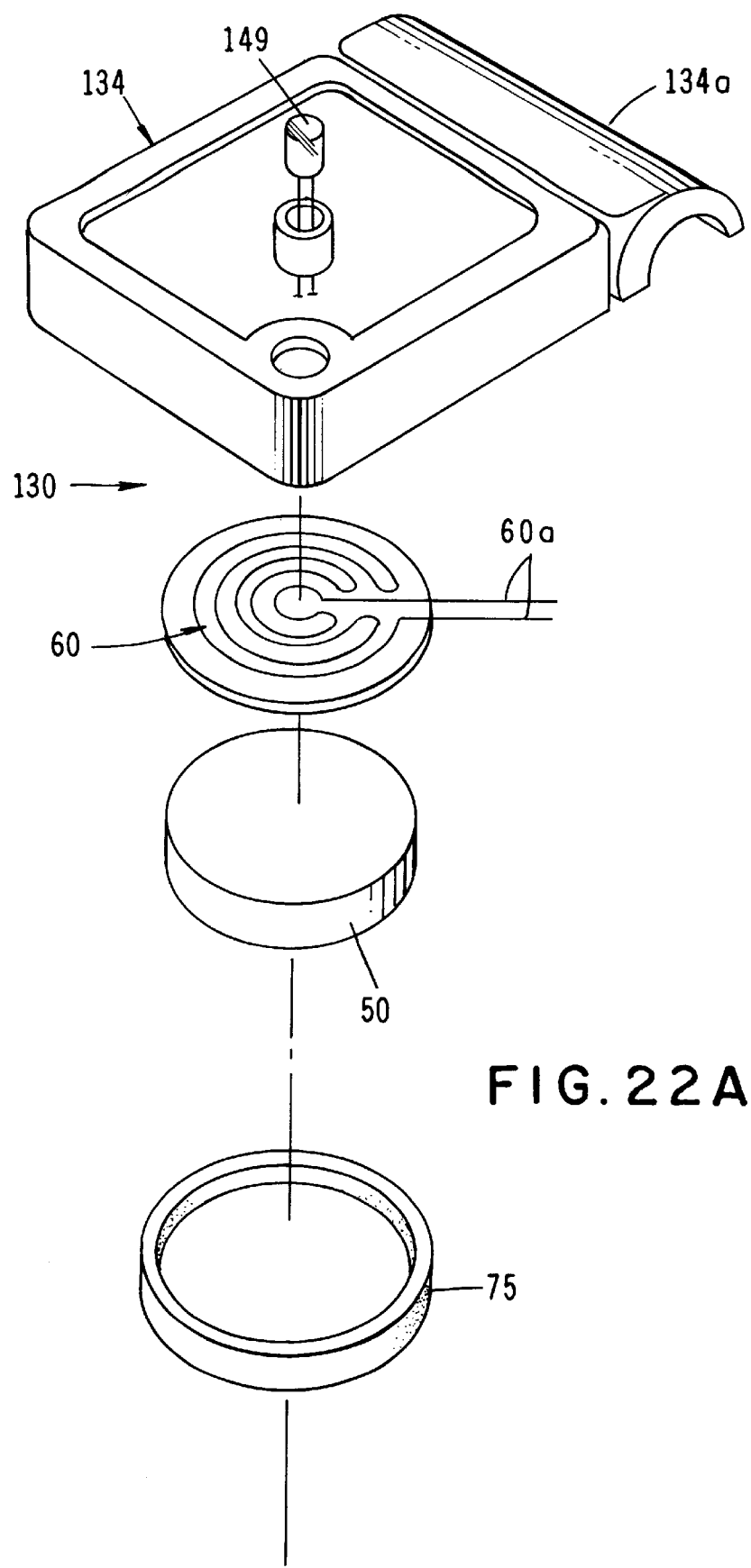
FIG. 22 is a generally perspective, exploded view of the apparatus shown in FIG. 18.
Figure 22B:
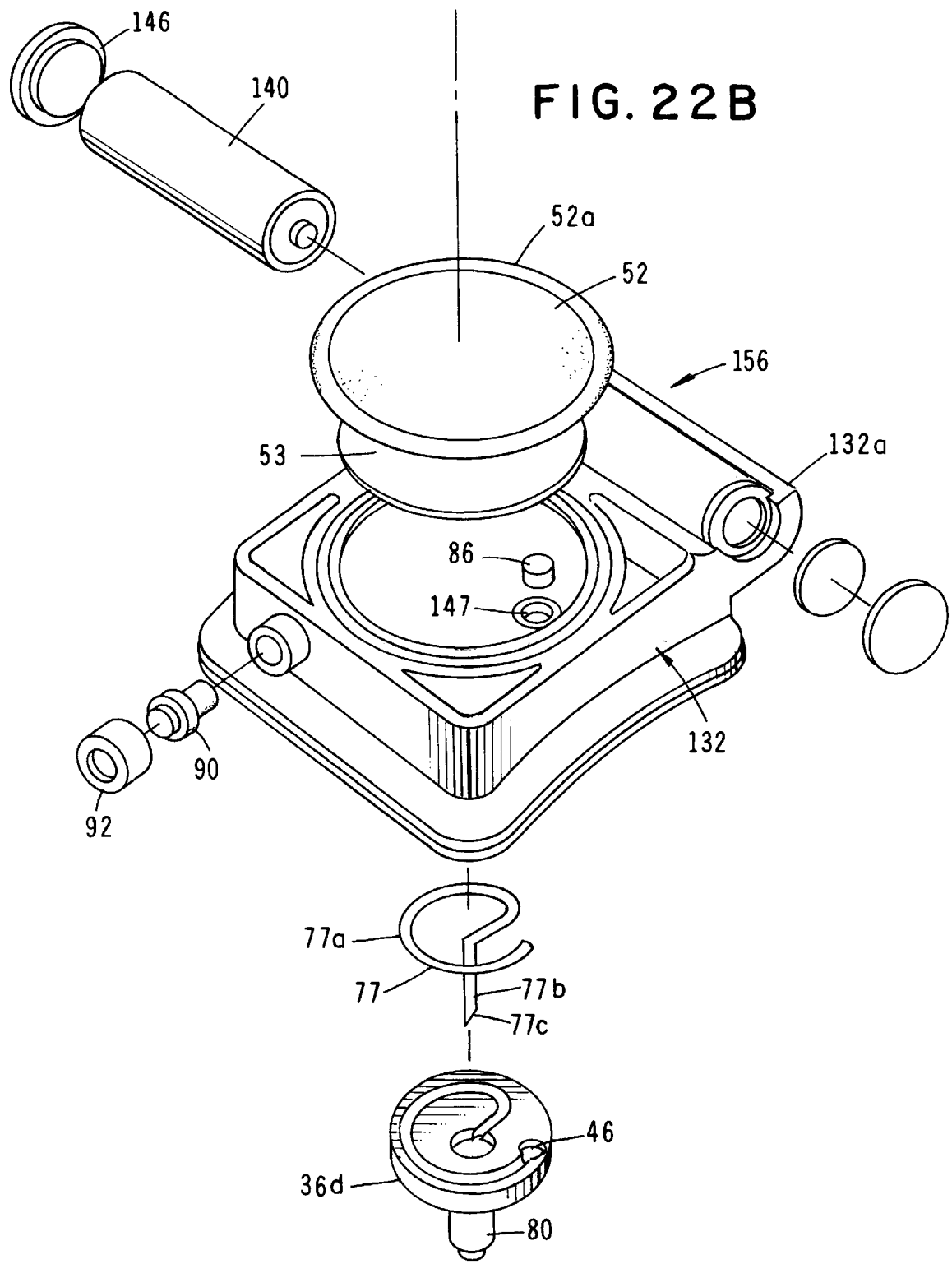

Turning once again to FIG. 3 of the drawings, it is to be noted that sealing means are superimposed over base 36 to seal chamber 42. This sealing means here comprises a distendable membrane 52 having an O-ring like periphery 52a that is sealably connected to the peripheral portion 36b of base 36 in the manner shown in FIG. 3C. Membrane 52 cooperates with base 36 to form fluid reservoir 44 (FIG. 3). It is to be understood that the reservoir-defining cavity can be of any desired geometry. In a manner presently to be described, fill means are provided for introducing fluids into reservoir 44 through a fluid inlet 58 formed in base 36 (FIG. 3). As mass 50 is heated, it will controllably expand from the compressed configuration shown in FIG. 3 to an expanded configuration shown in FIG. 3B and, in so doing, will experience a change in volume. Mass 50 can be free standing or, if desired, can be encapsulated within a yieldably deformable covering made up of interconnected membrane layers of the character shown in FIG. 22 of incorporated by reference U.S. Pat. No. 5,961,492.

Figure 6:
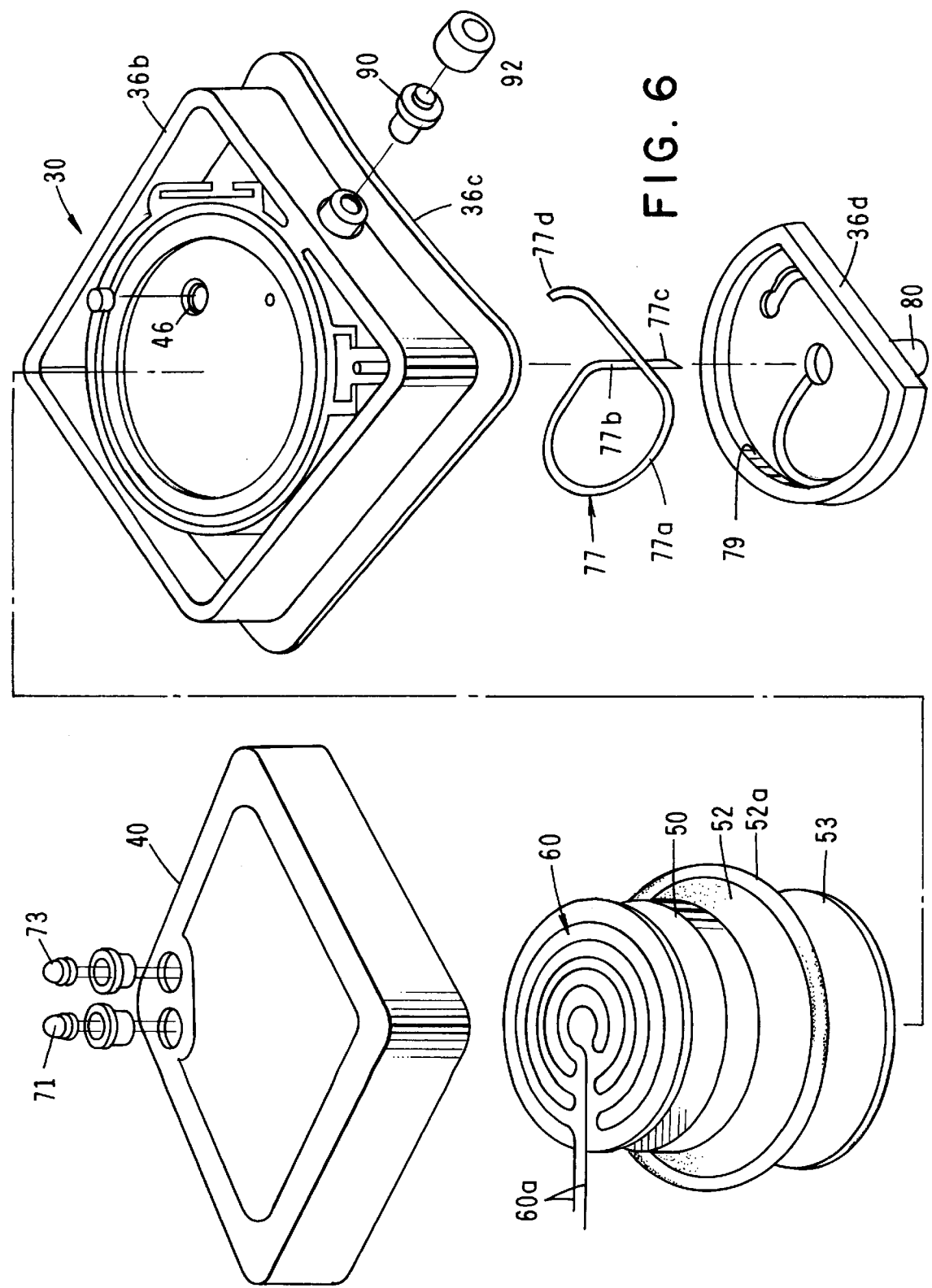
FIG. 6 is a generally perspective, exploded view of the apparatus shown in FIG. 1.

With the construction of the fluid storage device 32 shown in FIG. 3, when the heat expandable mass 50 is heated causing it to expand it will engage sealing membrane 52 which will, in turn, act on an expandable barrier membrane 53 (FIG. 6). Membrane 53, which is disposed within chamber 42, will then act on the fluid "F" which is contained within the reservoir 44 in a manner to controllably force it outwardly thereof through outlet passageway 46. As mass 50 expands, it will exert forces on sealing membrane 52 and barrier membrane 53 in a direction toward base 36 resulting in a controlled expelling of fluid from reservoir 44 through fluid outlet 46 and into the infusion means 34 of the apparatus, the details of construction, which will presently be described. If desired, medicament and instruction labels can be affixed to cover 40 to identify the medicinal fluid contained within reservoir 44 of the device.

Figure 3D:
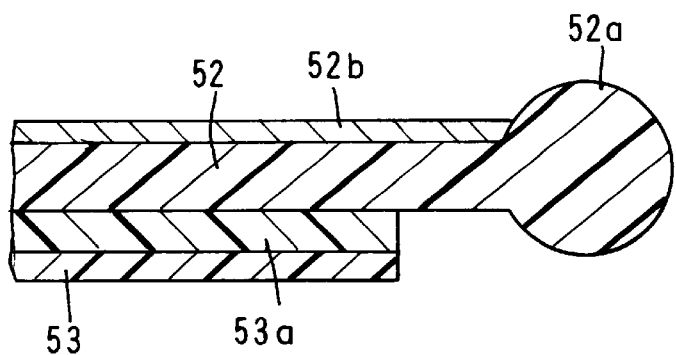
FIG. 3D is a greatly enlarged view of an alternate form of distendable membrane and barrier membrane of the invention showing the barrier membrane as a laminate construction.

For a discussion of the various materials that can be used to construct base 36, cover 40, and membrane 52, reference should be made to U.S. Pat. No. 5,205,820. This patent also discusses in greater detail techniques for labeling and venting of the fluid storage device where necessary. It should be noted that barrier membrane 53 can be of a single layer or multiple layer construction with one of the layers such as layer 53a comprising a thermal barrier (see FIG. 3D).

Thermal barrier layer 53a can be formed from various materials including a polyurethane foam material sold under the name and style Poron® by Rogers Corporation of Rogers, Conn.; silicone rubber or foam also sold by Rogers Corporation; and a polyethylene naphthalate (PEN) sold by Amoco Chemicals Co. It should also be understood that a barrier layer 52b may also be provided to overlay membrane 52 and can function as either a chemical barrier or as a thermal barrier.

Figure 7:
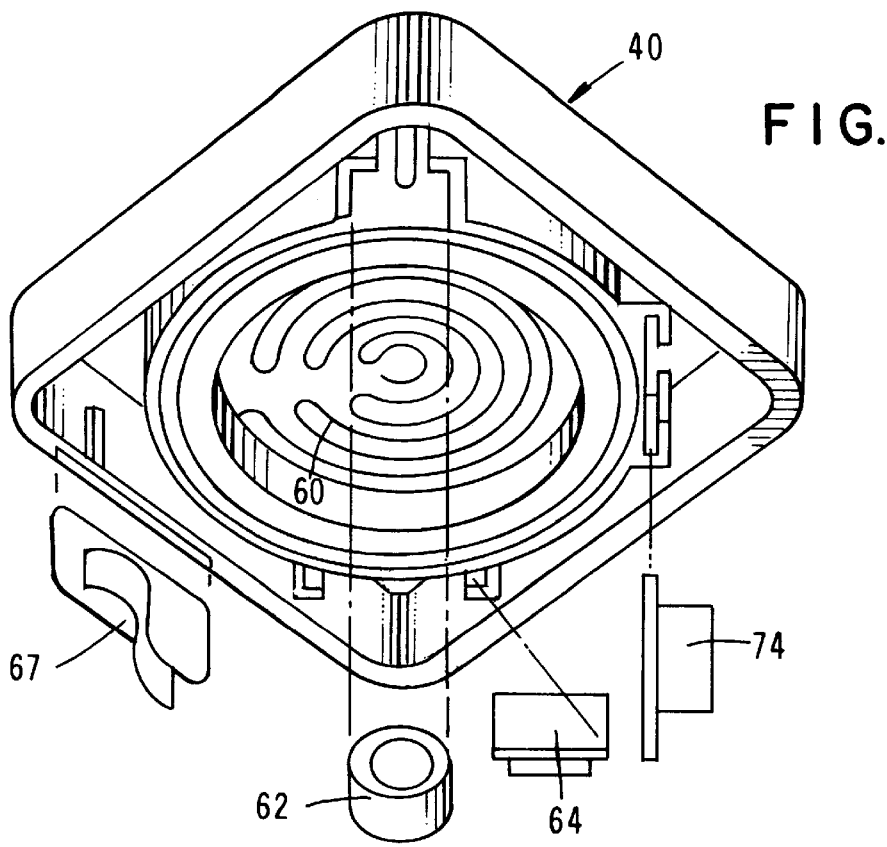
FIG. 7 is a generally perspective, bottom view of the cover sub-assembly shown in FIG. 6.
Figure 9:
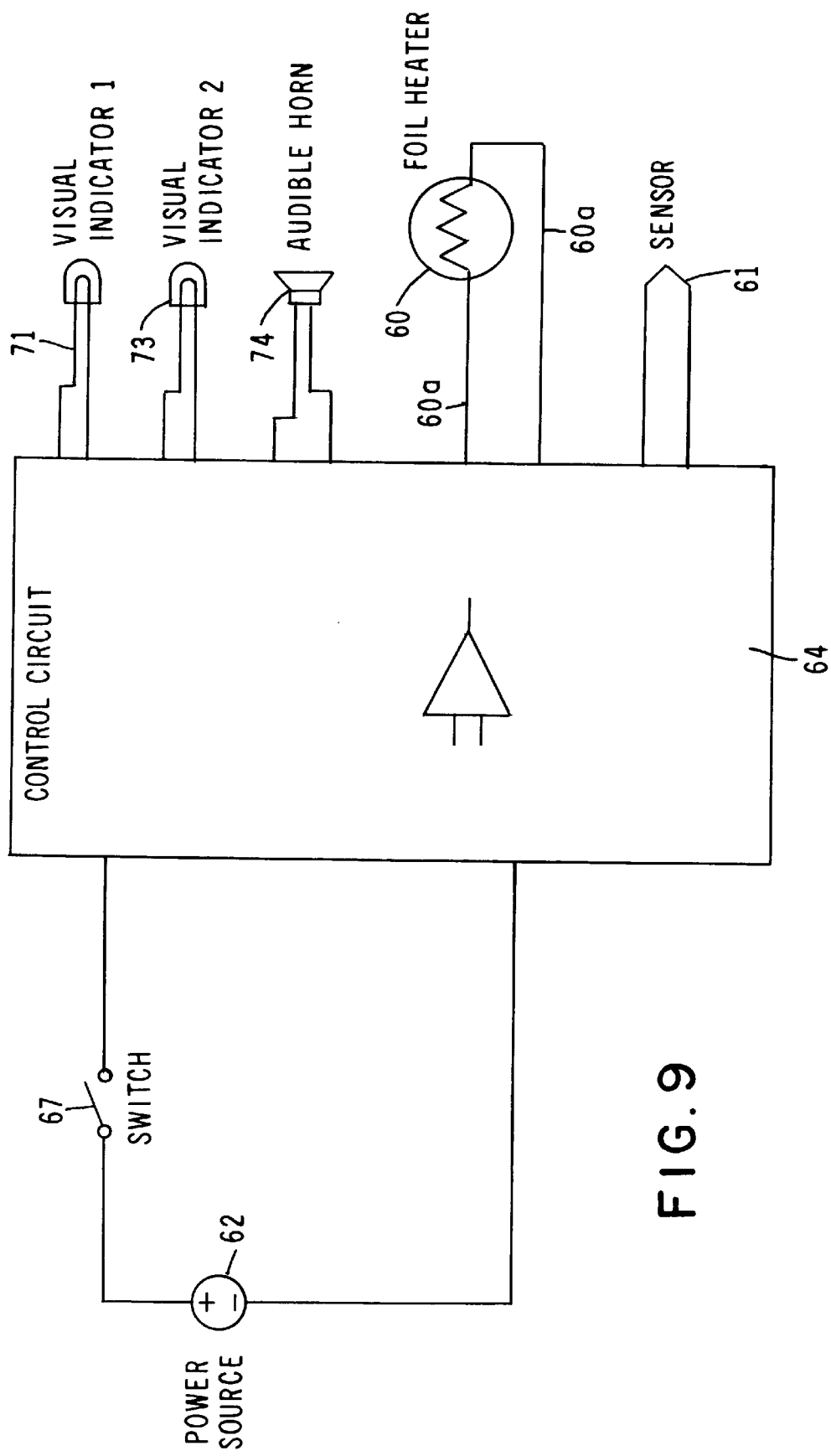
FIG. 9 is a generally schematic view of one form of the electrical circuitry of the invention.
Figure 9A:
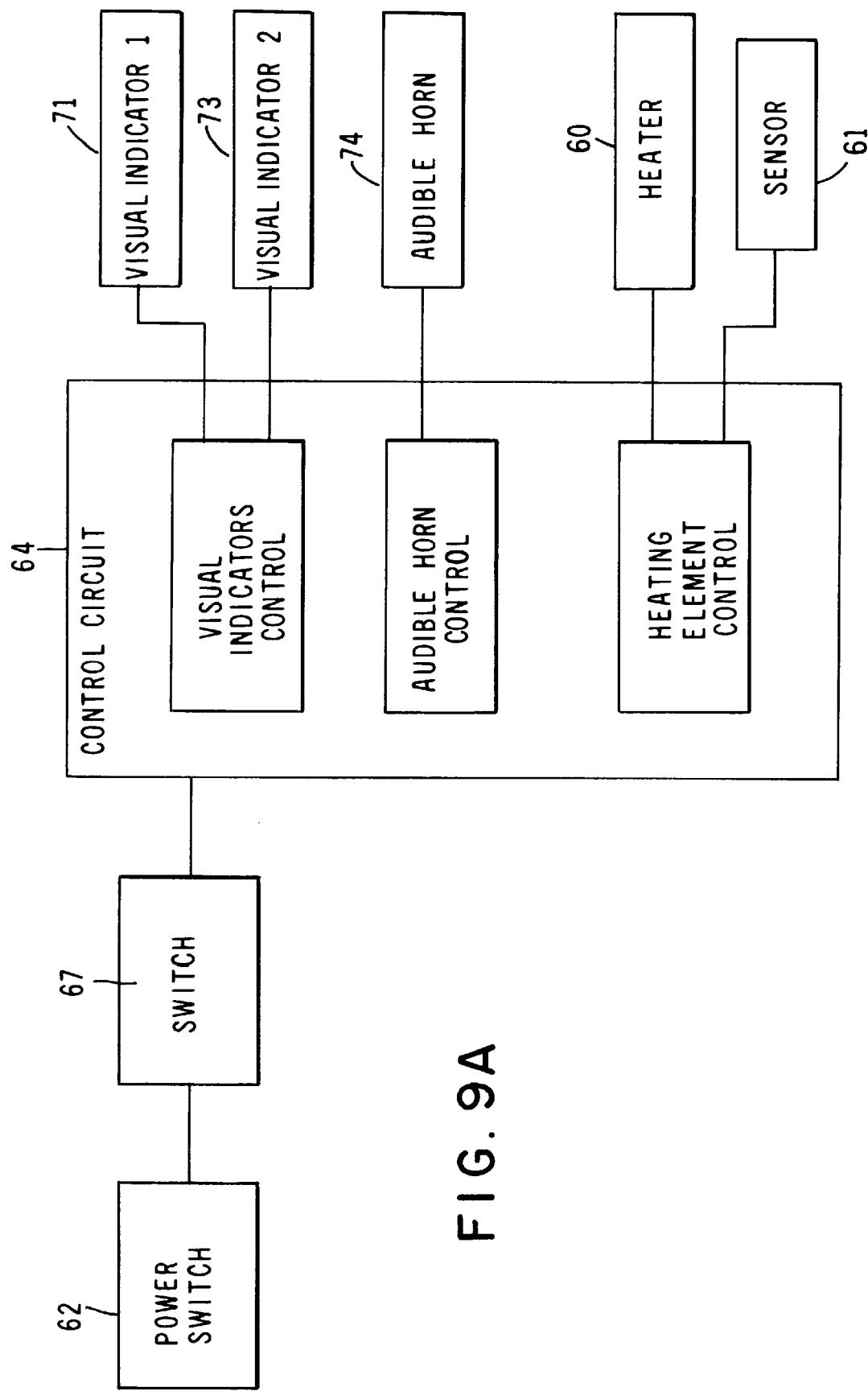
FIG. 9A is a block diagram of the electrical circuitry shown in FIG. 9.
Figure 10:
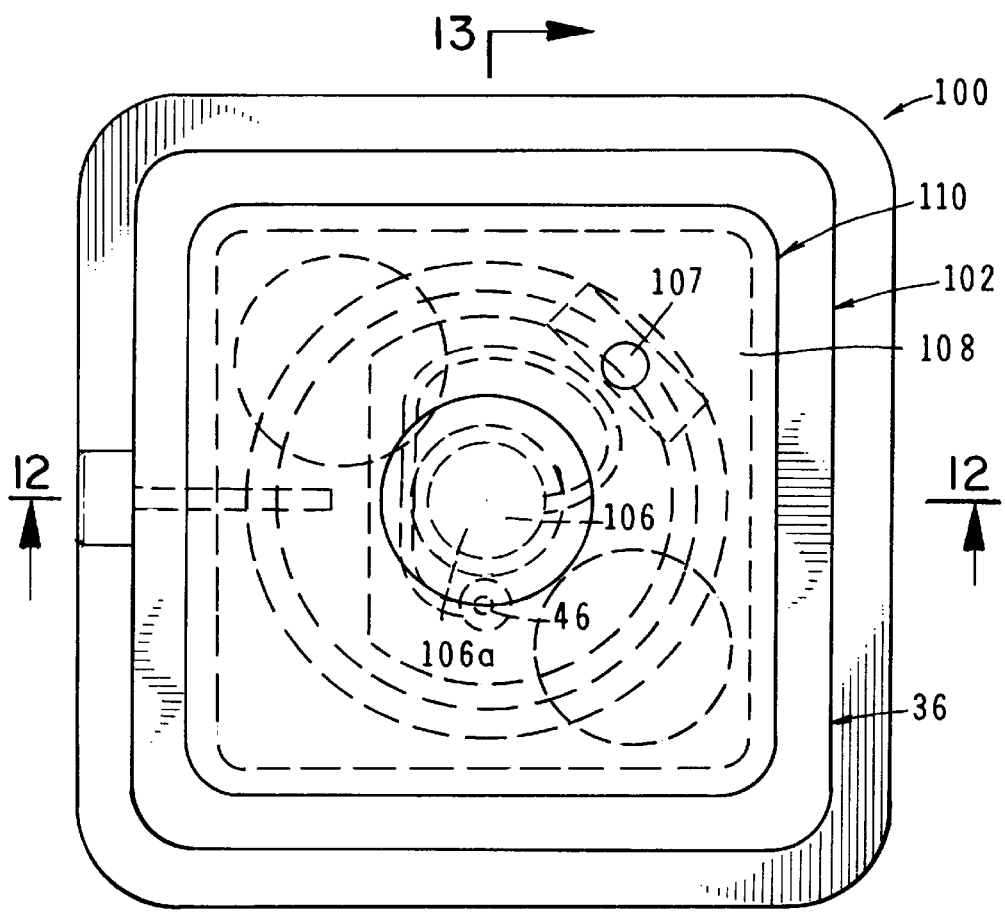
FIG. 10 is a top plan view of an alternate form of the fluid delivery apparatus of the invention.
Figure 11:
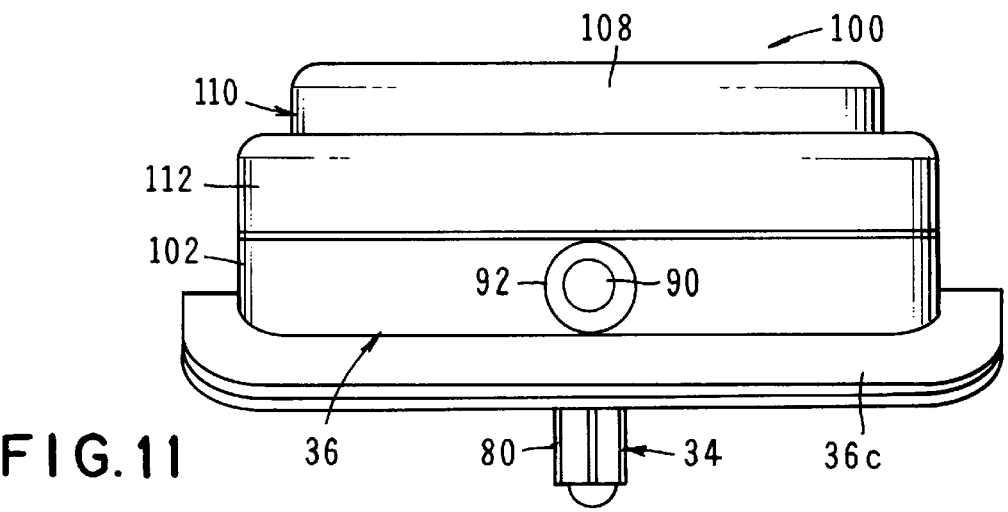
FIG. 11 is a side elevational view of the device shown in FIG. 10.

Forming a unique aspect of the apparatus of the present invention is the stimulation means for controllably heating expandable mass 50. As best seen in FIGS. 6 and 7, this stimulation means here comprises a flat printed circuit heater element 60 for heating element 60 and an operating chip 64 (FIGS. 7, 9 and 9A), which comprises the control circuit of the apparatus for operably interconnecting the heating element with the battery. As shown in FIG. 3, flat circuit heater element 60 is disposed within chamber 42 and is located between expandable mass 50 and the upper surface 42a of chamber 42. In operation, when heater element 60 is energized by operation of a membrane switch 67 (FIG. 7) it will generate heat sufficient to cause expandable mass 50 to force membrane 52 downwardly toward base 36 in the manner shown in FIG. 3B causing the fluid "F" to controllably flow through outlet 46 in a direction toward the infusion means 34. The heater element leads 60a (FIG. 6) are interconnected with battery 62 via the operating chip 64 and the membrane switch 67 in a manner well understood by those skilled in the art. Referring to FIGS. 9 and 9A, one form of the electrical circuitry of the heating means of the invention is there shown illustrating the manner of inter-connection of the various components that make up the stimulation means. Also forming a part of the stimulation means of the invention are indicator means for indicating energization and deenergization of the heater element. These indicator means here comprise red and green light emitting diodes 71 and 73 respectfully, which diodes are carried by cover 40 in the manner indicated in FIG. 6. Also comprising a part of the indicator means of the invention is an audio horn 74 which is suitably interconnected with battery 62 and chip 64 and functions to emit an audio signal when the reservoir of the device is empty (see also FIG. 9).

Turning particularly to FIGS. and 9 and 9A, the electrical circuitry of the apparatus can be seen to comprise a power source, shown here as battery 62 which, via switch 67, controls current flow to a control circuit which comprises the earlier identified chip 64. Operably interconnected with the control circuit is the previously identified foil heater 60, a heat sensor 61 for sensing the temperature of the foil heater, the visual indicators, or red and green light emitting diodes 71 and 73 and the audio horn 74.

As best seen in FIGS. 3, 3B and 6, the infusion means of the invention here comprises a uniquely configured hollow cannula 77. Cannula 77 includes a circuitously shaped body portion 77a which is disposed within a chamber 79 formed within a base insert 36d which comprises a part of base assembly 36. Cannula 77 also includes an outlet end here provided in the form of a needle-like segment 77b (FIG. 3B) which extends generally perpendicularly downward from the lower surface of the base and is used for subdermal infusion of medicinal fluids into the patient. For this purpose, segment 77b is provided with a sharp ground needlepointed extremity 77c (FIGS. 3 and 3B). Also shown in FIG. 3 is a twist-off protective sheath 80, which forms a part of base insert 36d. Sheath 80 surrounds and protects extremity 77c of the cannula. The body portion of the very small diameter spiral cannula 77 is rigidly supported within base insert 36d by encapsulation means such as a standard potting compound "P" (FIG. 3C) of a character well known to those skilled in the art.

Figure 5:
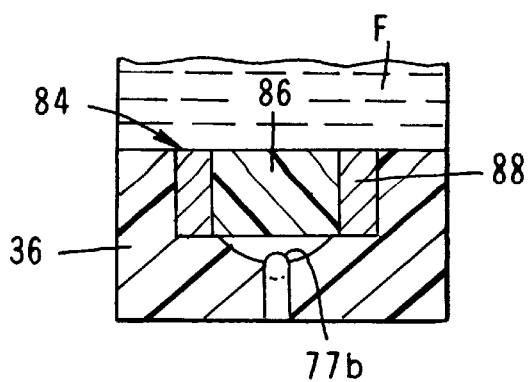
FIG. 5 is an enlarged, cross-sectional view of the area designated in FIG. 4 as 5—5.

As best seen in FIGS. 4 and 5, the inlet 77d of cannula 77 is in fluid communication with reservoir 44 via the novel flow control means of the invention which is shown here as flow control assembly 84. Flow control assembly 84 comprises a rate control or impedance member 86 that is held in position within outlet 46 by an elastomer molded ring 88. Member 86 can be constructed from a porous ceramic, a plastic, a sintered metal or other suitable materials which will control the rate of fluid flow toward cannula 77.

While cannulas of conventional construction can be used as the infusion means, a novel feature of the present invention relates to the novel design of the circuitously shaped cannula and the unique manner of its interconnection with base 36. More particularly, with the novel construction shown in the drawings, when the device is connected to the patient the needle portion 77c of the cannula penetrates the patient's skin and tissue as, for example, that found on the patient's arm, leg, or abdomen, while the body portion thereof is securely held in position within base insert 36d.

In using the apparatus of the present invention, reservoir 44 is first filled with the beneficial agent to be infused into the patient. This is accomplished through use of the fill means of the invention, which here comprises a non-coring, elastomeric septum 90. As shown in FIG. 6, septum 90 is securely held in position within base 36 by a clamping ring 92, which is, in turn affixed to base 36. Septum 90 is of standard construction and is penetrable by a cannula of a filling syringe of conventional construction. The conventional syringe (not shown) can be used to introduce the fluid to be dispensed to the patient into inlet passageway 58 and thence into reservoir 44. It is to be understood, however, that reservoir 44 can also be filled at the factory at the time of manufacture of the fluid storage device. Alternatively, the reservoir can be filled in the field shortly before use by means of the conventional syringe.

With reservoir 44 filled in the manner shown in FIGS. 3 and 4 of the drawings, protective sheath 80 is slipped from the end of cannula. With end 77c of cannula 77 thus exposed, the infusion device can be interconnected with the patient by penetrating the patient's skin with the sharp point 77c of the infusion cannula. As the infusion needle penetrates the patient's skin and tissue, the lower surface of base 36, which is preferably coated with an adhesive, or a suitable adhesive coated pad, will engage the patient's skin so as to hold the device securely in position. If desired, a peelable cover can be emplaced over a portion of the lower surface of the device to maintain the adhesive in an aseptic condition until time of use.

When the device is suitably affixed to the patient's body, such as to an arm, leg, or abdomen, energization of heating element 60 will cause heat expandable mass 50 to expand in the manner shown in FIG. 3B thereby causing the fluid "F" contained within reservoir 44 to controllably flow under pressure toward outlet passageway 46. For this purpose, mass 50 should controllably expand within a temperature range in excess of normal body temperature. The fluid "F" entering outlet passageway 46 will flow through a fluid flow control means and into inlet 77d of cannula 77 (FIG. 4).

Turning to FIGS. 10 through 17, an alternate form of the apparatus of the invention for use in the infusion of medicinal fluids into a patient is there shown and generally designated by the numeral 100. This alternate embodiment is similar in many respects to that shown in FIGS. 1 through 9 and like numerals are used in FIGS. 10 through 16 to identify like components. As best seen by referring to FIGS. 12 and 14, the apparatus here comprises a low-profile device 102 for infusing fluid contained within the device into the patient. While the base assembly, the fill means and the infusion means of the invention are substantially identical to that previously described in connection with FIGS. 1 through 9, the stimulation means is of a somewhat different construction. More specifically, the stimulation means here comprises a heater means which includes a foil heater 104 and the circuitry which controls the heater. As shown in FIGS. 14, 17 and 17A, this circuitry includes a dome switch subassembly 106 that is mounted within an electronics cover 108 that forms a part of the cover sub-assembly 110 of this latest embodiment of the invention.

Figure 12:
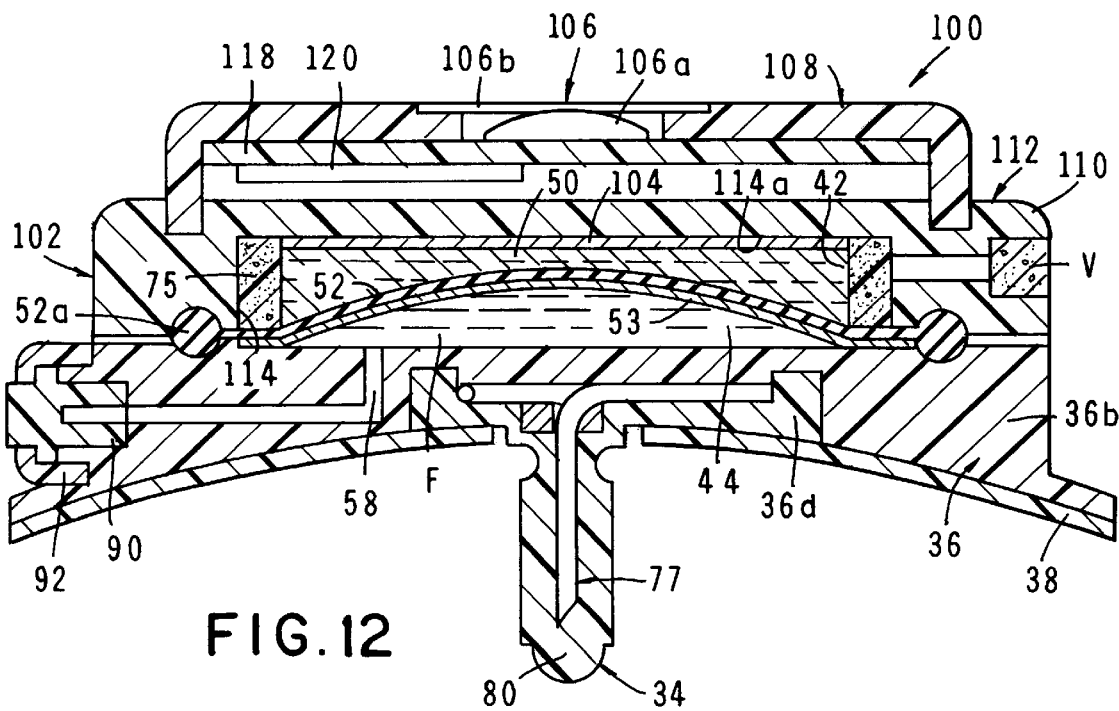
FIG. 12 is a cross-sectional view taken along lines 12—12 of FIG. 10.

Formed within cover 112 of cover sub-assembly 110, which is connected to base 36, is a generally circular shaped chamber 114 (FIGS. 12 and 13), which houses the earlier described heat-expandable means of the invention. As before, the stimulation means functions to act upon the expandable gel in a manner to cause the fluids contained within the sealed reservoir 44 of the device (FIG. 12) to flow outwardly through an outlet 46 formed in base 36 The expandable gel, or thermal expandable polymer mass 50, functions to controllably force the fluids contained within the sealed reservoir 44 of the device to flow outwardly through the previously identified outlet 46 formed in base 36. The expandable gel is of the character previously described herein and is covered by a sealing means comprising membrane 52 which is sealably connected to the peripheral portion 36b of base 36 in the manner indicated in FIGS. 12 and 12A. However, as illustrated in FIG. 12, the heat expandable gel is here mounted within a porous gas vent ring 75 that functions during the reservoir filling step to vent chamber 42 via a porous plug vent "V". Fill means of the same character described in connection with the first embodiment of the invention are provided for introducing fluids into reservoir 44 through fluid inlet 58 formed in base 36.

As best seen in FIGS. 12, 14, 17 and 17A, the heating means here comprises the previously identified foil heater element 104, a power source or battery 116 for heating element 104 and an electronics mounting board 118 which carries battery 116 as well as an audio horn 120. As shown in FIG. 12, heater element 104 is disposed within chamber 42 and is located between expandable mass 50 and the upper surface 114a of chamber 114. In operation, when heater element 104 is energized by operation of the dome switch 106a of switch assembly 106 by pressing on the flexible switch cover 106b (FIG. 12) it will generate heat sufficient to cause expandable mass 50 to force membranes 52 and 53 downwardly toward base 36 causing the fluid "F" to controllably flow throughout outlet 46 in a direction toward the infusion means 34. The heater element leads 104a (FIG. 14) are interconnected with battery 116 and with switch 106a and with a light-emitting diode or indicator 107 in a manner well understood by those skilled in the art. More particularly, referring to FIGS. 17 and 17A, the electrical circuitry of the heating means of this latest form of the the invention is there shown indicating the manner of inter-connection of the various components that make up the heating means. The indicator means of this latest embodiment comprise the previously identified diode 107 and the audio horn 120 which is suitably interconnected with battery 116 and functions to emit an audio signal when the reservoir of the device is empty.

As indicated in FIGS. 17 and 17A, the electrical circuitry of this latest form of the apparatus comprises a power source, shown here as battery 116 which, via switch 106 controls current flow from the power source to the foil heater 104. The light emitting diode 107 is interconnected between the switch 106 and the foil heater 104 in the manner shown in FIGS. 17 and 17A.

Figure 12A:
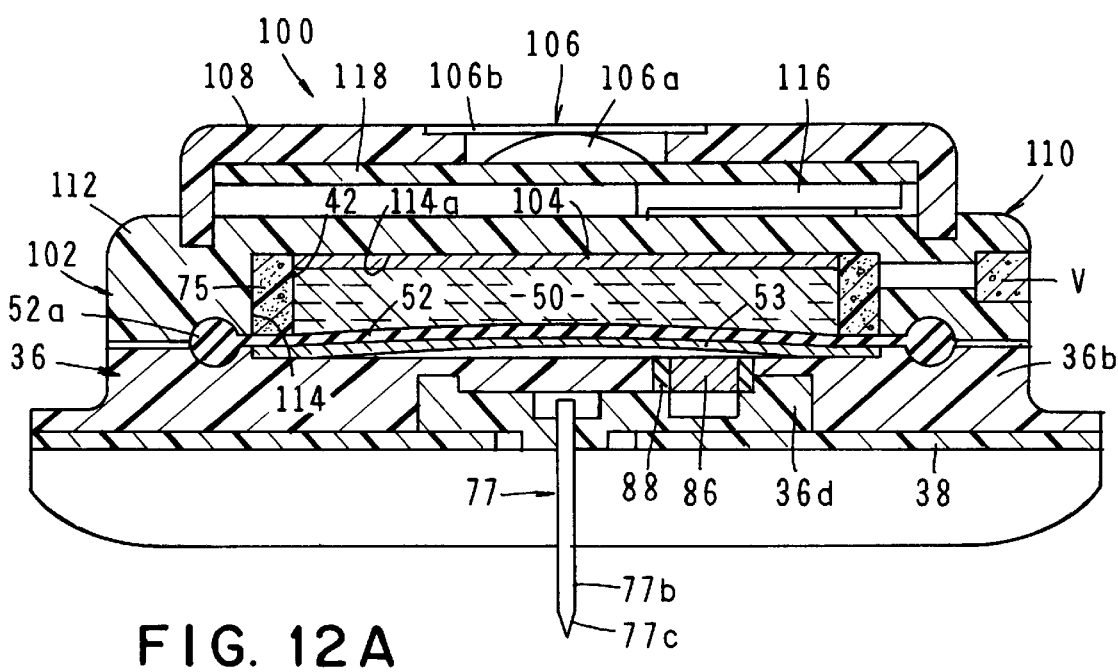
FIG. 12A is an enlarged, cross-sectional view similar to FIG. 12 but showing the heat expandable gel expanded.
Figure 12B:
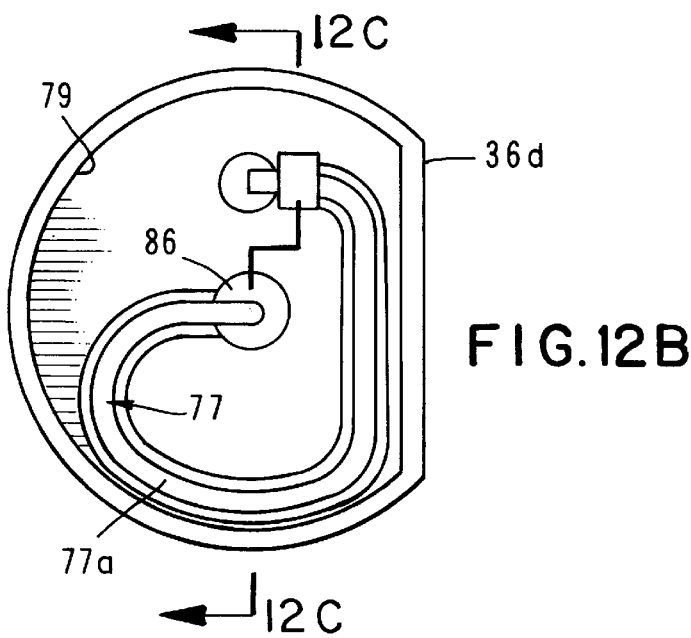
FIG. 12B is an enlarged plan view of the delivery cannula assembly.
Figure 12C:
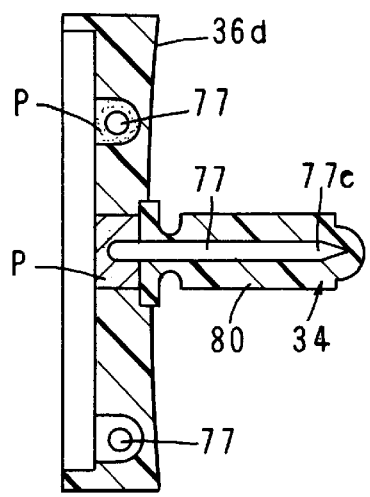
FIG. 12C is a cross-sectional view taken along lines 12C—12C of FIG. 12B.
Figure 12D:
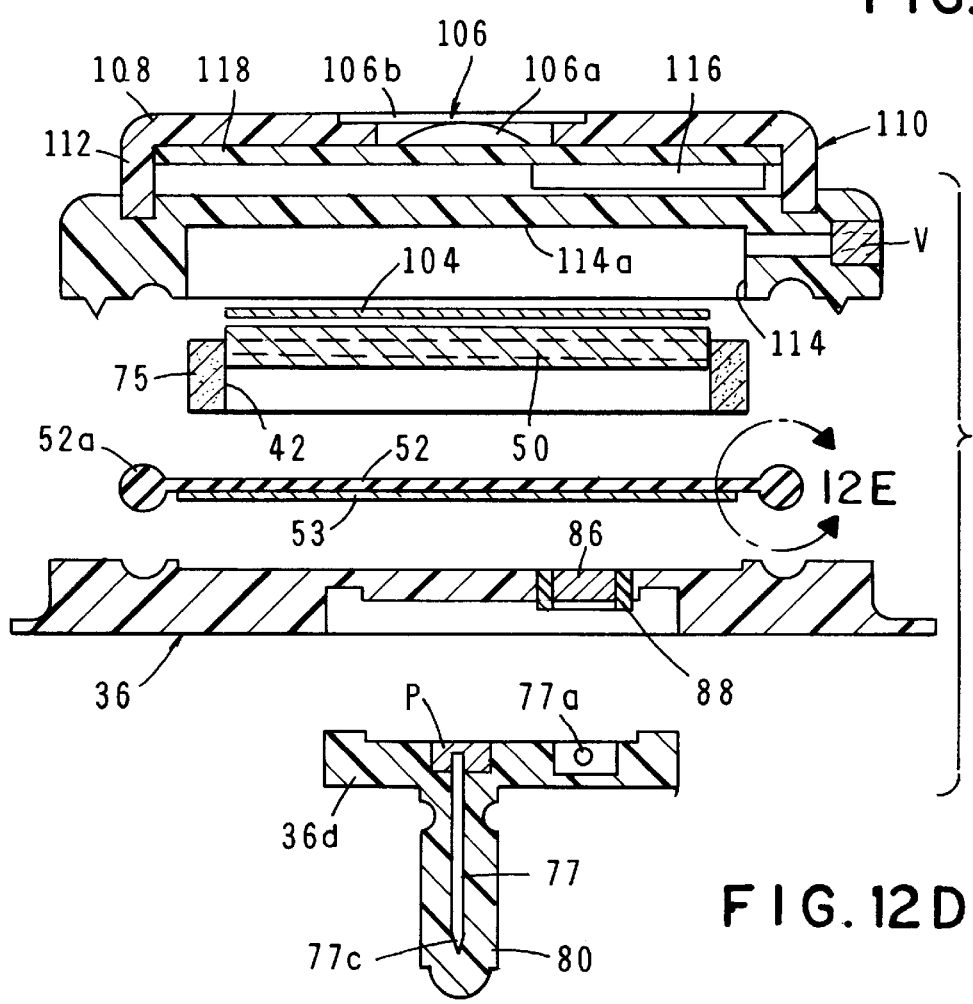
FIG. 12D is an enlarged, cross-sectional, exploded view of the assembly shown in FIG. 12.
Figure 12E:
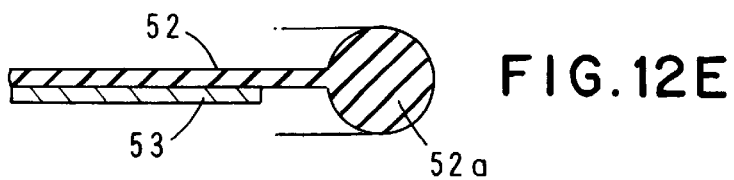
FIG. 12E is an enlarged, cross-sectional view of the area designated in FIG. 12D as 12E.
Figure 13:
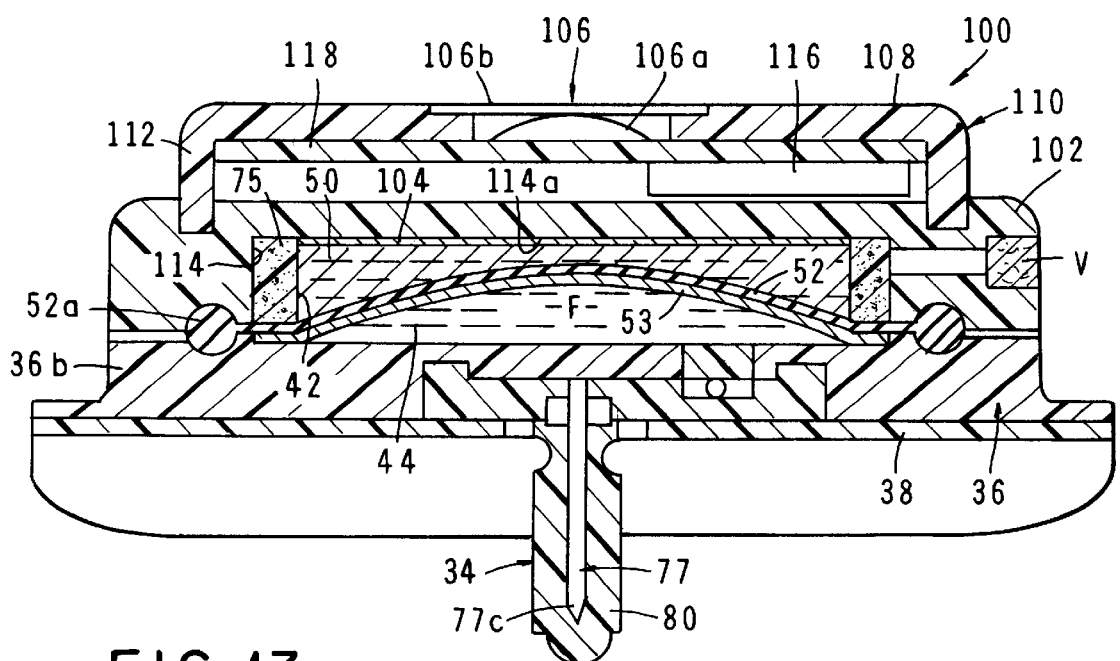
FIG. 13 is a cross-sectional view taken along lines 13—13 of FIG. 10.
Figure 13A:
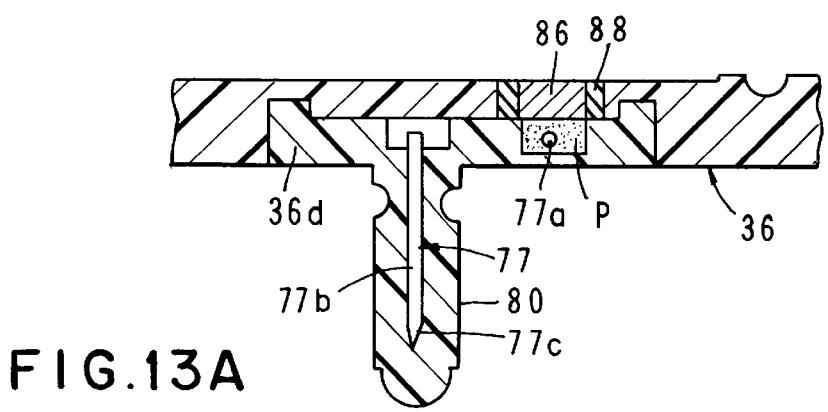
FIG. 13A is an enlarged, cross-sectional view showing the cannula assembly of FIG. 12D connected to the base assembly shown in FIG. 12D.

As illustrated in FIGS. 12B and 12C, the infusion means of this latest form of the invention is similar to that previously described and includes a base insert 36d that houses the circuitous cannula 77 and is interconnectable with the base of the delivery device in the manner shown in FIGS. 12 and 13.

In using the apparatus of this latest form of the invention, reservoir 44 is filled in the manner previously described through use of the fill means of the invention, which comprises a non-coring elastomeric septum 90 (FIG. 12). As before, reservoir 44 can be filled at the factory at the time of manufacture of the fluid storage device or it can be filled in the field shortly before use by means of a conventional syringe.

With reservoir 44 filled in the manner shown in FIGS. 12 and 13 of the drawings, protective sheath 80 is slipped from end of cannula and the device is interconnected with the patient by penetrating the patient's skin with the sharp point 77c of the infusion cannula.

With the device affixed to the patient's body, energization of heating element 104 will cause heat expandable mass 50 to expand in the manner shown in FIG. 12A thereby causing the fluid "F" contained within reservoir 44 to controllably flow under pressure toward outlet passageway 46 via the flow control means of the device which is of the character previously described.

Turning to FIGS. 18 through 22, another form of the apparatus of the invention for use in the infusion of medicinal fluids into a patient is there shown and generally designated by the numeral 130. This latest embodiment is also similar in many respects to that shown in FIGS. 1 through 9 and like numerals are used in FIGS. 18 through 22 to identify like components. As before, the apparatus here comprises a low-profile device for infusing fluid contained within the device into the patient. While the fill means and the infusion means of the invention are substantially identical to that previously described in connection with FIGS. 1 through 9, the base and cover assemblies are of a somewhat different construction and are adapted to removably support a different type of battery. More specifically, the base component 132 here includes a side extension 132a which, in conjunction with a side extension 134a of a cover assembly 134, forms a generally cylindrical shaped battery receiving chamber 136 (FIG. 19) for receiving a high performance battery 140 such as a lithium or mercury battery. Battery 140 comprises a part of the heating means of this latest form of the invention, which also comprises the previously described flat printed circuit heater element 60.

Figure 19B:
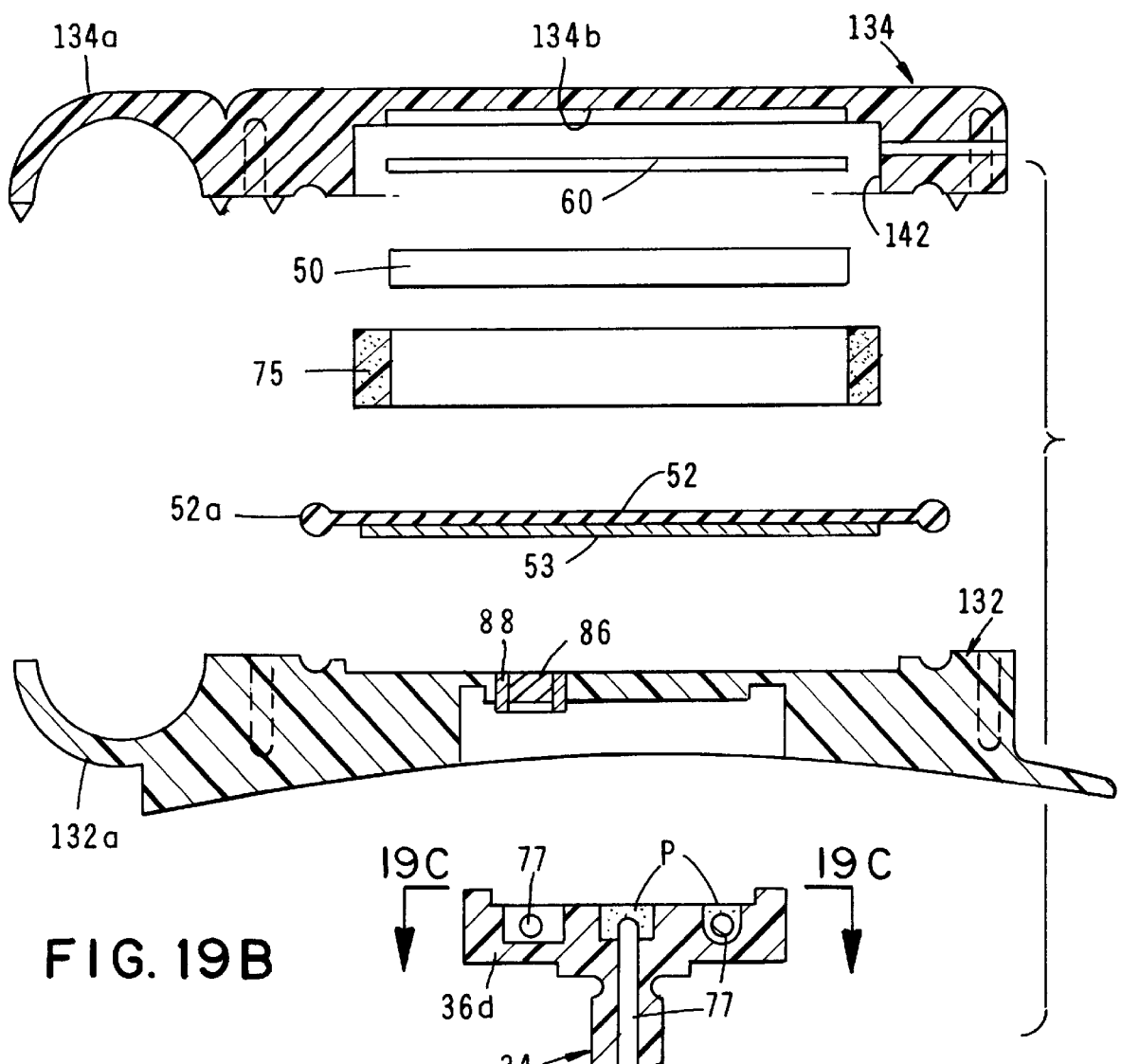
FIG. 19B is an exploded, cross-sectional view of the device shown in FIG. 19.
Figure 19C:
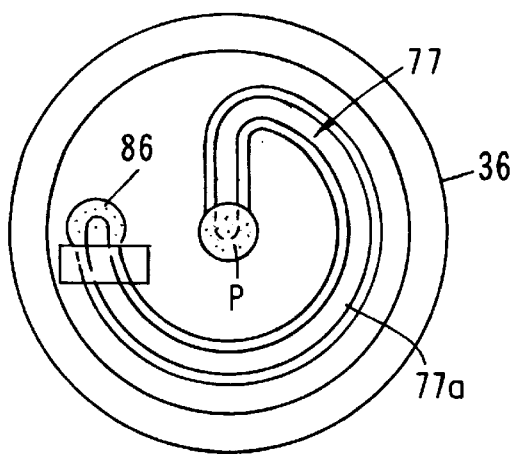
FIG. 19C is a view taken along lines 19C—19C of FIG. 19B.

As shown in FIG. 19, flat circuit heater element 60 is disposed within a chamber 142 formed in cover 134 and is located between expandable mass 50 and the upper surface 134b of chamber 142. In operation, after the reservoir has been filled using the fill means, the heater element 60 can be energized by operation of a dome switch 146 mounted proximate one end of chamber 136 (FIG. 18). Dome switch 146 can be off, on or intermittent depending upon the end use application of the device. Upon being energized, the heating element will generate heat sufficient to cause expandable mass 50 to force membranes 52 and 53 downwardly toward base 132 causing the fluid "F" to controllably flow through an outlet 147 formed in base 132 in a direction toward the infusion means 34.

Figure 26:
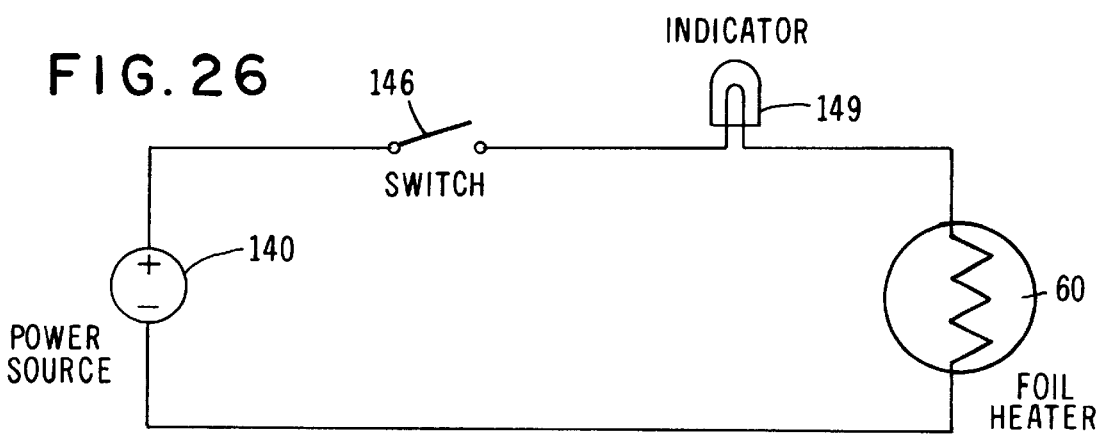
FIG. 26 is a generally schematic view of another form of the electrical circuitry of the invention.
Figure 26A:
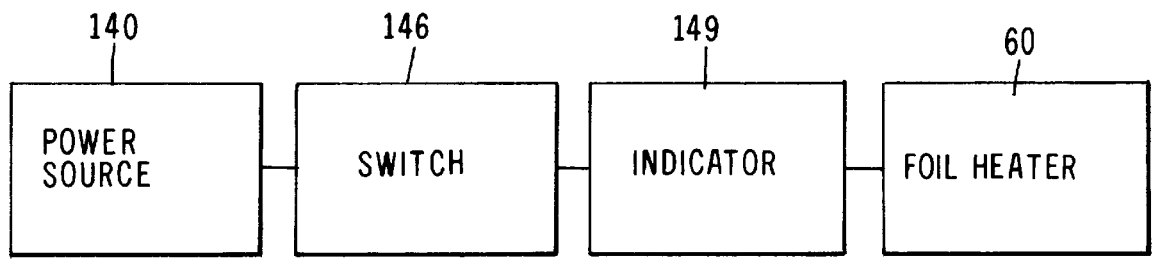
FIG. 26A is a block diagram of the electrical circuitry shown in FIG. 26.
Figure 27:
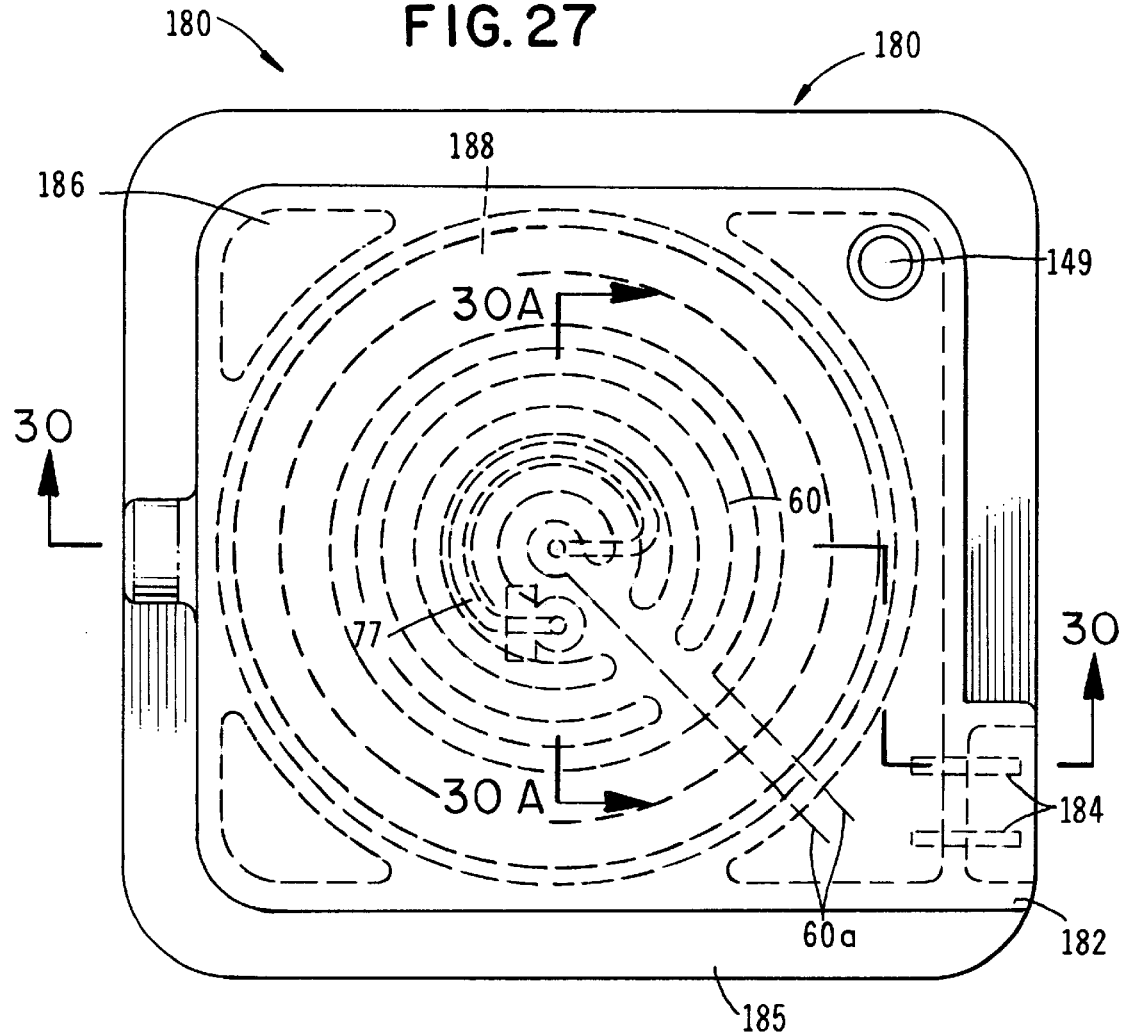
FIG. 27 is a top plan view of yet another alternate form of the fluid delivery apparatus of the invention.
Figure 31:
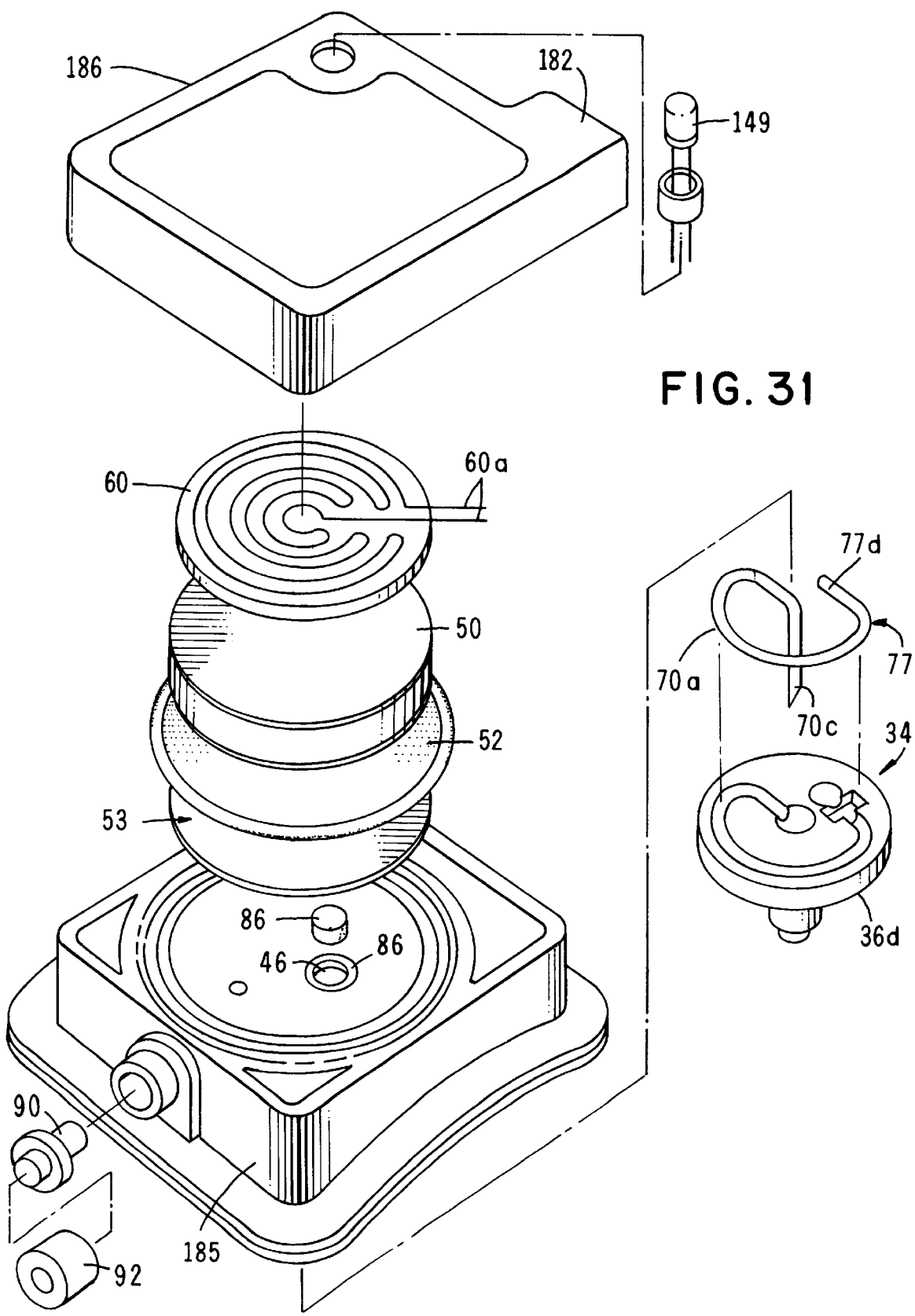
FIG. 31 is a generally perspective, exploded view of the apparatus shown in FIG. 27.
Figure 32:
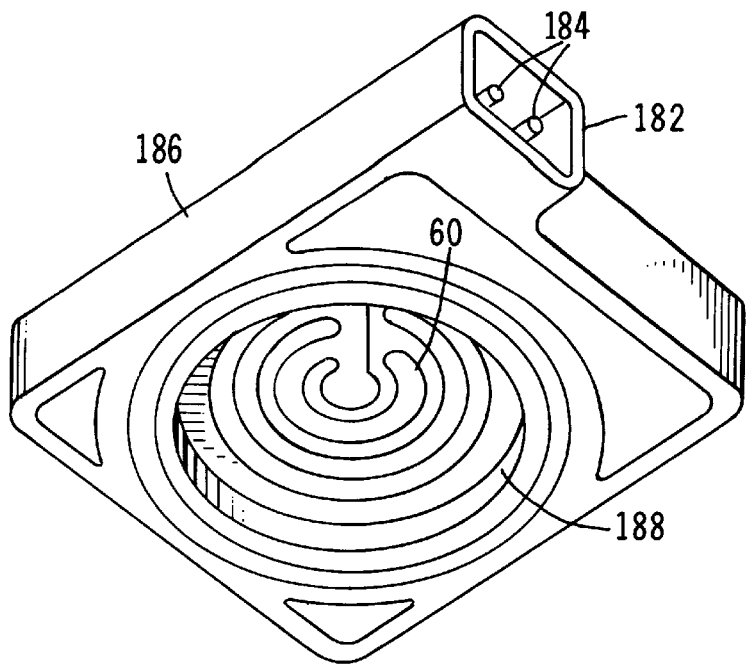
FIG. 32 is a generally perspective, bottom view of the cover sub-assembly shown in FIG. 31.
Figure 33:
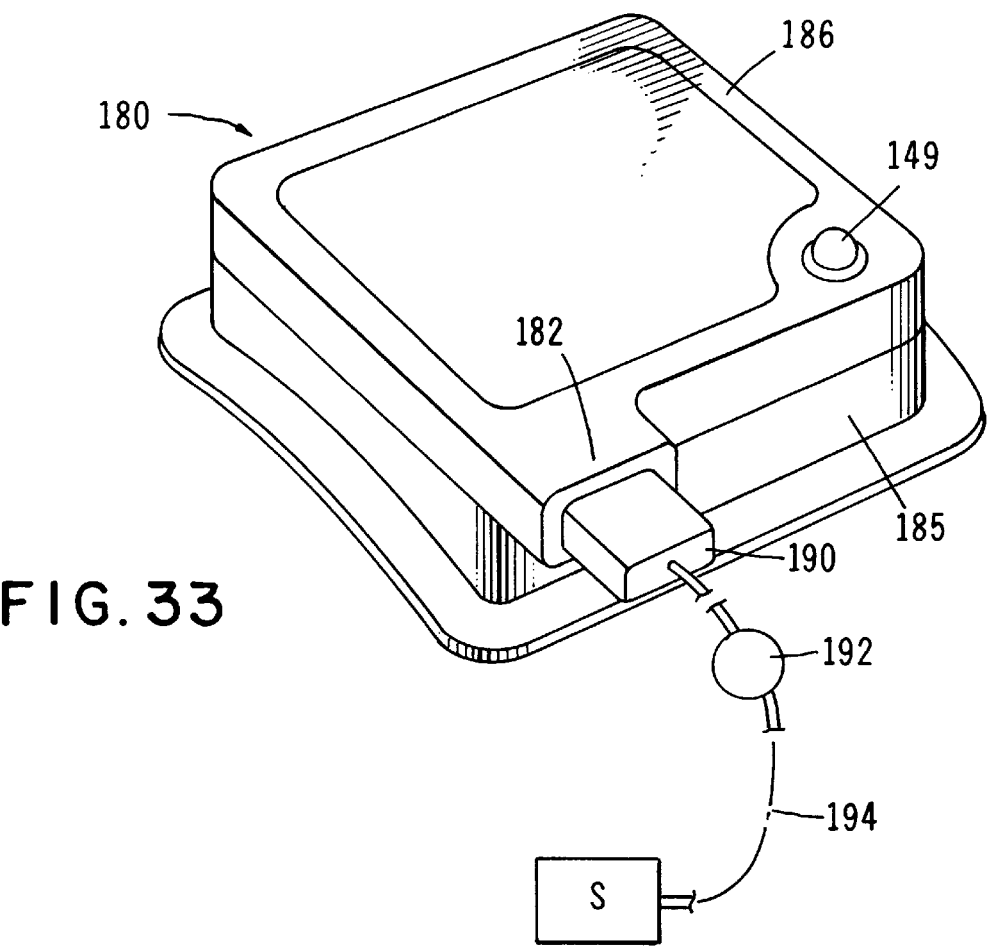
FIG. 33 is a generally perspective view of the device illustrated in FIG. 27 shown interconnected with an external power source.

The heater element leads 60a of the heater element (FIG. 22) are interconnected with battery 140 and with dome switch 146 (FIG. 18) in the manner shown in FIGS. 26 and 26A. Also forming a part of the heating means of this latest form of the invention are indicator means for indicating energization and deenergization of the heater element. This indicator means here comprises a light emitting diode 149 that is carried by cover 134 in the manner illustrated in FIG. 22.

An important aspect of the apparatus of this latter form of the invention is the previously discussed infusion means or assembly 34. Assembly 34, which comprises a subcutaneous infusion device, is of identical construction to that previously described and functions in an identical manner.

Figure 24:
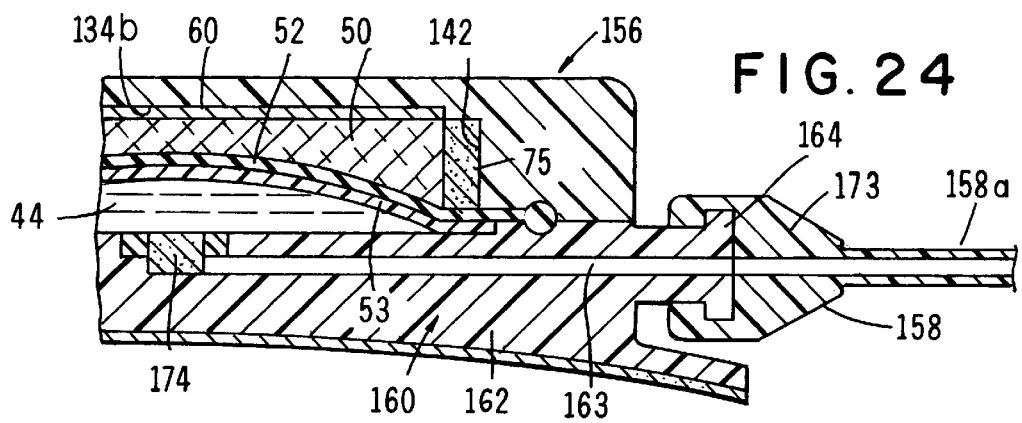
FIG. 24 is a cross-sectional view taken along lines 24—24 of FIG. 23.
Figure 25:
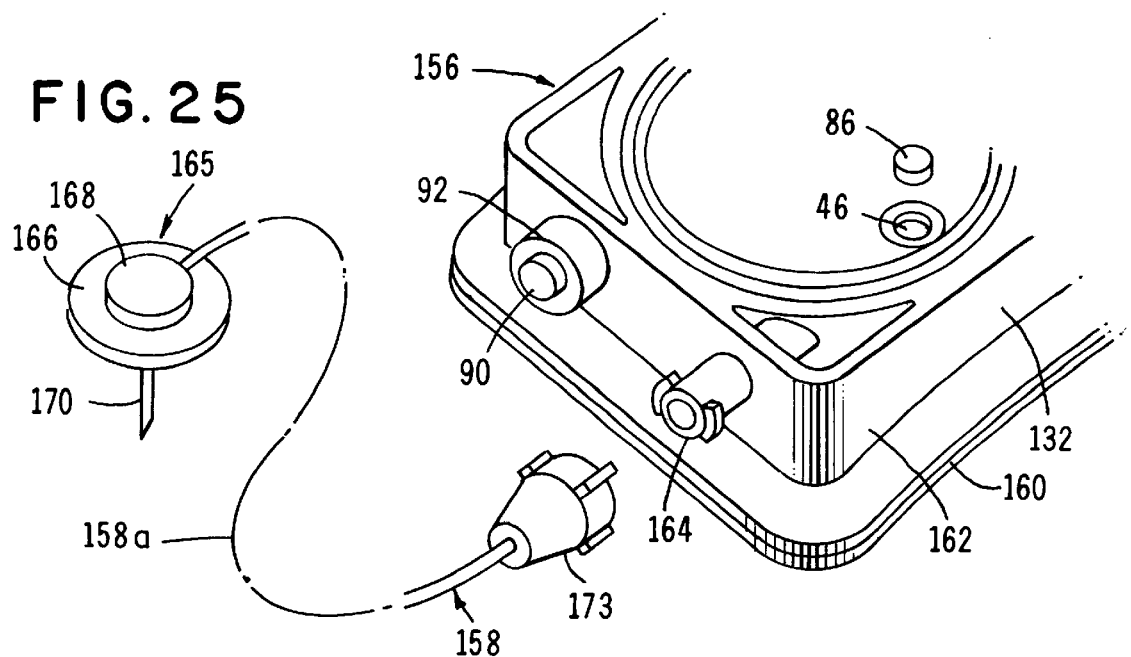
FIG. 25 is a generally perspective fragmentary view of the area of the apparatus shown in FIG. 23.

Turning to FIGS. 23 through 25, yet another form of the apparatus of the invention is there shown and generally designated by the numeral 156. This latest embodiment is similar in many respects to that shown in FIGS. 18 through 21 and like numerals are used in FIGS. 23 through 25 to identify like components. While the cover assembly, the fill means and the heating means of the invention are substantially identical to that previously described in connection with FIGS. 18 through 21, the base assembly 160 and the infusion means are of a somewhat different construction. More particularly, the infusion means here comprises a novel administration set 158 that is connected to base 162 of base assembly 160 in the manner best seen in FIGS. 23 and 25.

As shown in FIGS. 23, 24 and 25, the base assembly 160 also includes an outlet passageway 163 that communicates with reservoir 44 and with an externally accessible luer connector 164. Luer connector 164 enables quick interconnection of the infusion means with base assembly 160 so that the delivery tube or administration line 158a of the administration set 158 is placed in fluid communication with fluid passageway 163. Forming a unique aspect of the administration set is the remotely located subcutaneous infusion device 165, which is provided at the distal end of line 158a (FIG. 25). This device is similar in construction and operation to device 83 shown in FIG. 16 of incorporated by reference U.S. Pat. No. 5,961,492 and includes a base 166 that supports a generally dome-shaped cover 168. Cover 168 defines a chamber 95, which houses the body portion of a hollow cannula 170 of the invention. Cannula 170 includes a needle-like segment which extends generally perpendicularly downward from base 166 and is used for subdermal infusion of medicinal fluids into the patient. Reference should be made to U.S. Pat. No. 5,961,492 for a more detailed description of infusion device 165. Provided at the proximal end of line 158 is a luer connector 173 that can be mated with luer connector 164 to sealably connect the administration set with base 162.

With the construction thus described, after the reservoir has been filled using the fill means, the heater element 60 can be energized by operation of a dome switch 146 mounted proximate one end of chamber 142 (FIG. 18). Upon being energized, the heating element will generate heat sufficient to cause expandable mass 50 to force membranes 52 and 53 downwardly toward base 160 causing the fluid "F" to controllably flow through an outlet 147 formed in base 132 (FIG. 24) then into passageway 163 and finally into the infusion means of this latest form of the invention. After the infusion device 165 has been connected to the patient in the manner discussed in incorporated by reference U.S. Pat. No. 5,961,492, the fluid will controllably flow into the patient via the flow control means of the invention.

The heater element leads 60a of the heater element (FIG. 22) are interconnected with battery 140 and with dome switch 146 in the manner indicated in FIGS. 26 and 26A. Also forming a part of the heating means of this latest form of the invention are indicator means for indicating energization and deenergization of the heater element. This indicator means here comprises a light emitting diode 149 that is carried by cover 134 in the manner illustrated in FIG. 22 and is interconnected with the foil heater in the manner indicated in FIGS. 26 and 26A.

Turning next to FIGS. 27 through 33, yet another form of the apparatus of the invention for use in the infusion of medicinal fluids into a patient is there shown and generally designated by the numeral 180. This latest embodiment is also similar in many respects to that shown in FIGS. 1 through 9 and like numerals are used in FIGS. 27 through 33 to identify like components. While the base, the fill means and the infusion means of the invention are once again substantially identical to that previously described in connection with FIGS. 1 through 9, the cover assembly is of a somewhat different construction and is adapted to provide a port 182 for housing an electrical connection means in the form of a multi-pin electrical interconnection 184 (FIG. 27) to enable the delivery device to be interconnected with an external power source.

As best seen in FIG. 30, the cover component 186 here includes a side extension which defines port 182 and a generally cylindrical shaped chamber 188 for receiving the previously described flat printed circuit heater element 60. As shown in FIG. 30, flat circuit heater element 60 is once again located between expandable mass 50 and the upper surface 188a of chamber 188.

In operation, after the reservoir has been filled using the fill means and the power source "S" has been connected to connector 184 using female connector 190 (FIG. 33),the heater element 60 can be energized by operation of a conventional switch 192 that is disposed within an electrical line 194 which interconnects the power source "S" with female connector 190. Power source "S" can comprise a battery pack, an AC/DC converter, or other type of power source known to those skilled in the art. Upon being energized, the heating element will generate heat sufficient to cause expandable mass 50 to force membranes 52 and 53 downwardly toward base 185 causing the fluid "F" to controllably flow through an outlet 46 formed in base 185 via flow control element 86 in a direction toward the infusion means 34. The heater element leads 60a of the heater element (FIG. 31) are interconnected with power source "S" and with switch 192 in the manner shown in FIGS. 34 and 34A.

Figure 36:
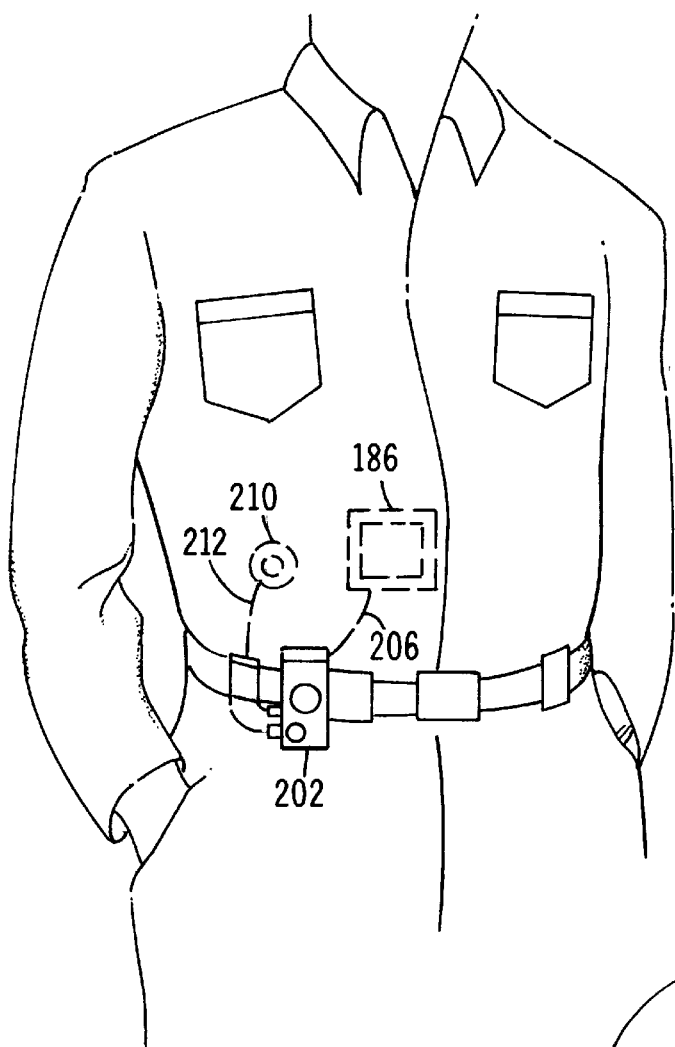
FIG. 36 is a generally perspective, diagrammatic view showing the apparatus illustrated in FIG. 35 interconnected with the patient.
Figure 37:
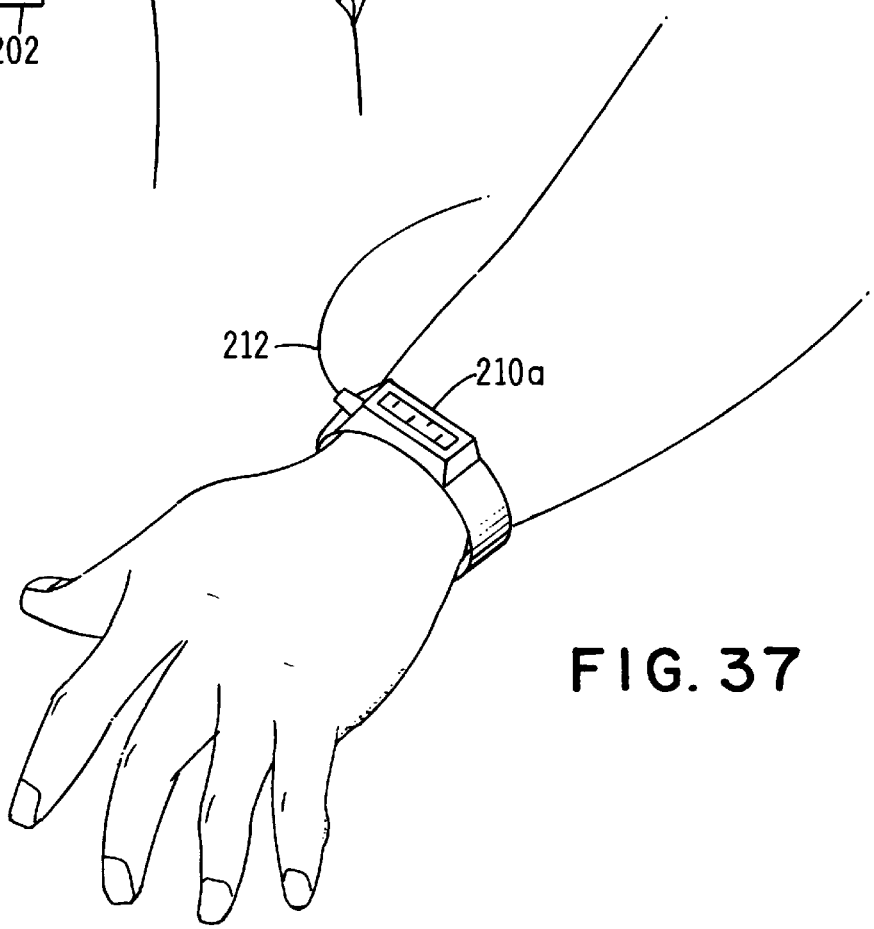
FIG. 37 is a generally perspective, diagrammatic view of an alternate form of metabolic sensing device connected to the patient's wrist.
Figure 38:
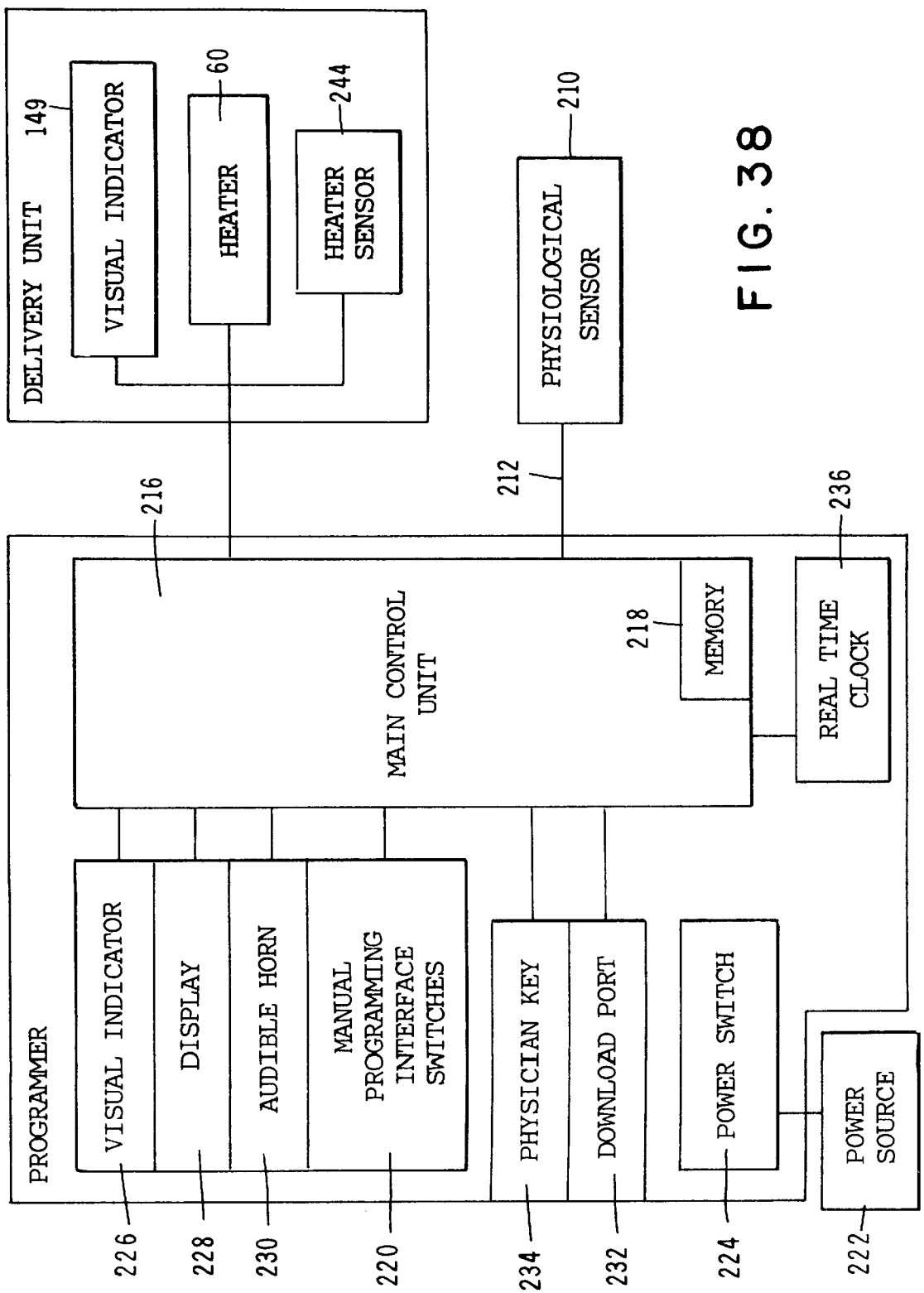
FIG. 38 is a block diagram showing the components of the controller and the fluid delivery device shown in FIG. 35.

Turning to FIGS. 35 through 37, still another form of the apparatus of the invention for use in the infusion of medicinal fluids into a patient is there shown and generally designated by the numeral 200. This latest embodiment is similar in many respects to that just described and shown in FIGS. 27 through 34 and like numerals are used to identify like components. While the base, fill means and infusion means of the invention are substantially identical to that previously described in connection with FIGS. 27 through 34, the power supply and infusion means are of a different construction. More specifically, the power supply comprises a novel belt mounted power supply and electronic controller 202 the character of which will presently be described. As best seen in FIGS. 35 and 38, controller 202 is electrically connected to cover 186 by female connector 190 and an electrical conduit 206. Female connector 190 mates with connector 184 in the manner previously described.

As indicated in FIGS. 35 and 36, controller 202 can be connected to the patient's belt or other article of clothing and is, in turn, connected to a sensor 210 by a conduit 212. The nature and purpose of sensor 210 will be discussed presently. As best seen by referring to FIGS. 35 and 38, controller 202 includes a housing 214 that houses the various operating components shown in FIG. 38, which comprise a main control unit 216 having a memory 218, manual programming interface switches 220, a conventional power source 222 and a power switch 224 (FIG. 38). Connected to main control unit 216 is a visual indicator 226, a data display 228 and an audible horn 230. Also connected to main control unit 216 is a download port 232, a physician's key 234 and a real time clock 236.

Referring also to FIG. 35, it can be seen that the delivery device, which includes base 185, cover 186 and heater 60 is connected to the patient in the manner previously described and as illustrated in FIG. 36. Located on the top of the controller 202 is a navigation keypad 240 and a function keypad 241.

In operation of the apparatus of this latest embodiment of the invention, the electronic controller can be programmed by a health care provider using an assigned physician's key and the various controls located on the controller to select the desired functions which can be displayed on the data display. By way of example, the controller can be programmed in a manner well known to those skilled in the art to precisely deliver basal, elevated basal, bolus and varying dosing volumes in response to either physiological sensor 210 or to a pre-programmed delivery protocol. In this regard, the various delivery levels can be achieved by selectively varying the power supplied to the delivery heater as, for example, by changing the voltage or current levels, by changing the pulse width modulation of the applied power, or by changing the frequency, amplitude or pulse amplitude modulation of the applied power. The electronic controller can also be programmed to monitor the heat sensor 244 of the delivery device (FIG. 38) to verify the desired delivery performance of the device and to detect the highly unlikely event of a thermal runaway failure of the heater. The user will be notified of any heater malfunction by the audio alarm or audible horn 230.

After the electronic controller is initially programmed, function keypads 241, which are operably associated with switches 220, can be used to select a different delivery schedule. If desired, once the unit is programmed, the controller can be locked using the physician's key thereby preventing any unauthorized user changes to the settings.

While the unit is operating, data display 228 will display information concerning the current basal and bolus settings, total drug amount delivery, time or dosage remaining or other information determined to be needed. Physiological sensor information could also be displayed, and downloaded to a compatible system to allow analysis of the physiological sensor data at a later time. In this regard, the previously identified physiological sensor 210 can comprise a glucose sensor of the general character developed by Minimed, Inc. of Sylmar, Calif. and Integ, Inc. of St. Paul, Minn. These devices, which may be affixed to the patient's abdomen as shown in FIG. 36, uses a small sampling cannula which is inserted into the tissue of the patient. Referring to FIG. 37, an alternate, wristmounted sensor 210a can also be used. This sensor may comprise a patch type sensor of the type developed by Cygins, Inc. of San Diego, Calif., or TCPI of Pompano Beach, Fla., or a sensor that can sample interstirial fluids.

Turning next to FIGS. 39 through 42, yet another form of the apparatus of the invention for use in the infusion of medicinal fluids into a patient is there shown. This latest embodiment is similar in many respects to that just described and shown in FIGS. 35 through 38 and like numerals are used to identify like components. While the cover, the heating means and fill means the invention are substantially identical to that previously described in connection with FIGS. 35 through 38, the infusion means are of a different construction. More specifically, the infusion means includes an infusion device 165 that is identical to that shown in FIG. 25. However, the infusion device is here connected to a slightly differently configured base component 242 by a novel quick connect assembly 244. As before, the power supply comprises a part of the novel belt mounted, electronic controller 202 which is of the character previously described.

Figure 39:
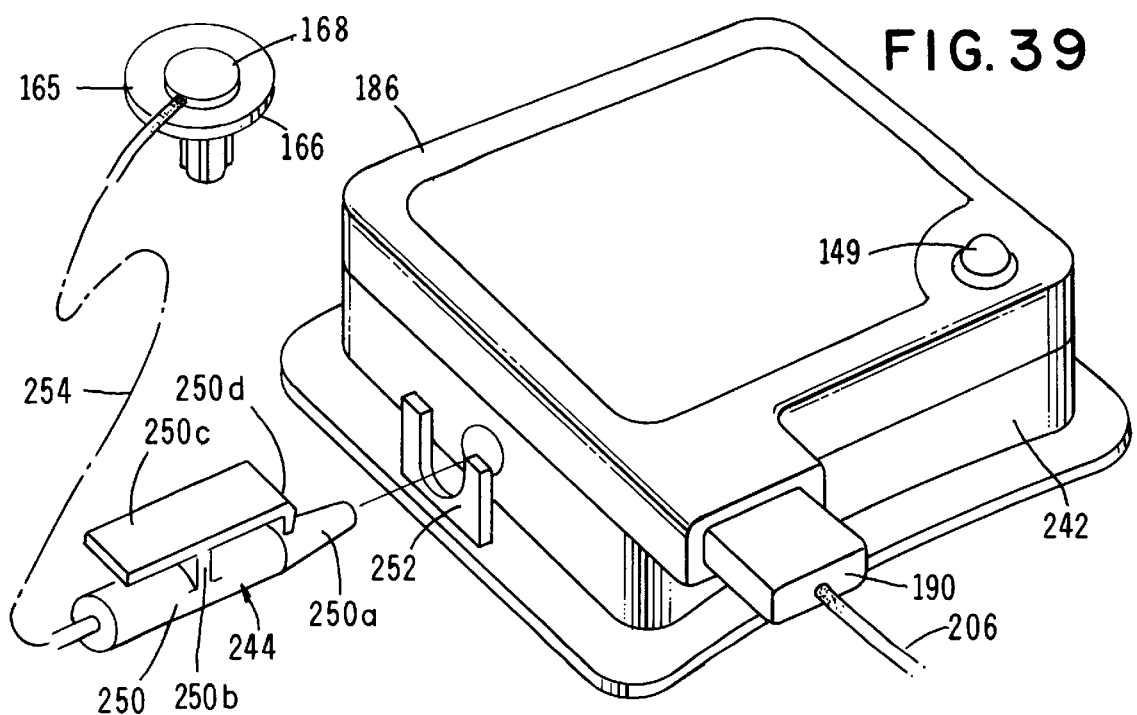
FIG. 39 is a generally perspective view of yet another embodiment of the invention.
Figure 40:
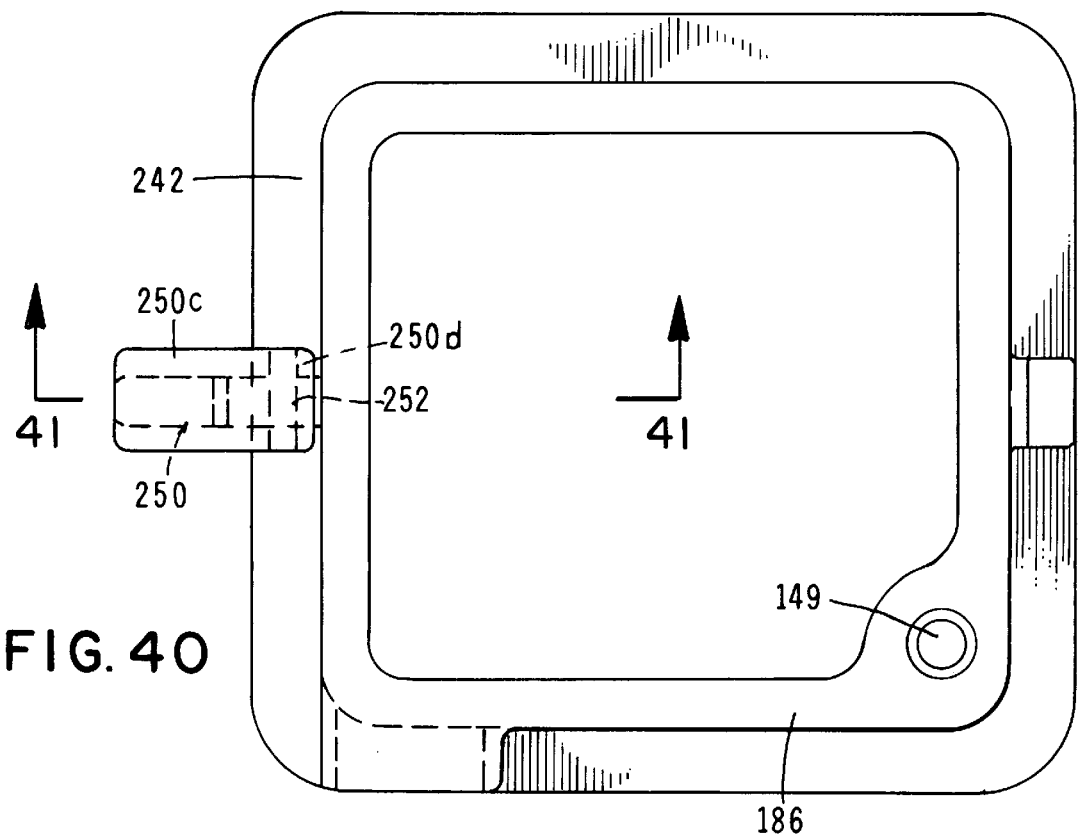
FIG. 40 is a top plan view of the base and cover assemblies of the apparatus shown in FIG. 39.

As best seen in FIGS. 39 and 41, base 242 includes a tapered chamber 246 (FIG. 41) that communicates with reservoir 44 via an outlet passageway 248. Quick connect assembly 244 here includes a body portion 250 having a tapered forward portion 250a that is sealably received within chamber 246 in the manner shown in FIG. 41. Body portion 250 also includes a centrally disposed, outwardly extending finger 250b which is either connected to, or alternatively is integrally formed with, an operating lever arm 250c to form a living hinge type construction. Formed proximate the inboard end of lever arm 250c is a locking tooth 250d which lockably engages an upwardly extending, generally "U" shaped member 252 that is provided on base component 242 (FIGS. 39 and 42). With this construction, an inward force imposed on the outboard end of arm 250c will cause locking tooth 250d to swing away from member 252 a sufficient distance to permit withdrawal of body portion 250a from chamber 246 so as to enable separation of the infusion device 165 from base 242.

In operating the apparatus of this latest form of the invention, after the reservoir 44 has been filled using the previously described fill means, the infusion device 165 can be interconnected with base 242 through appropriate manipulation of the quick connect mechanism. This done, the device can be interconnected with the patient and the heating element 60 be energized using the controller 202. The elevated temperature of the heating element will cause heat expandable mass 50 to increase in volume causing the fluid contained within reservoir 44 to controllably flow under pressure toward outlet passageway 248. The fluid will then flow through the central passageway 250e of body 250 , through a line 254 and into infusion device 165 for controlled delivery to the patient (FIG. 39).

Figure 51:
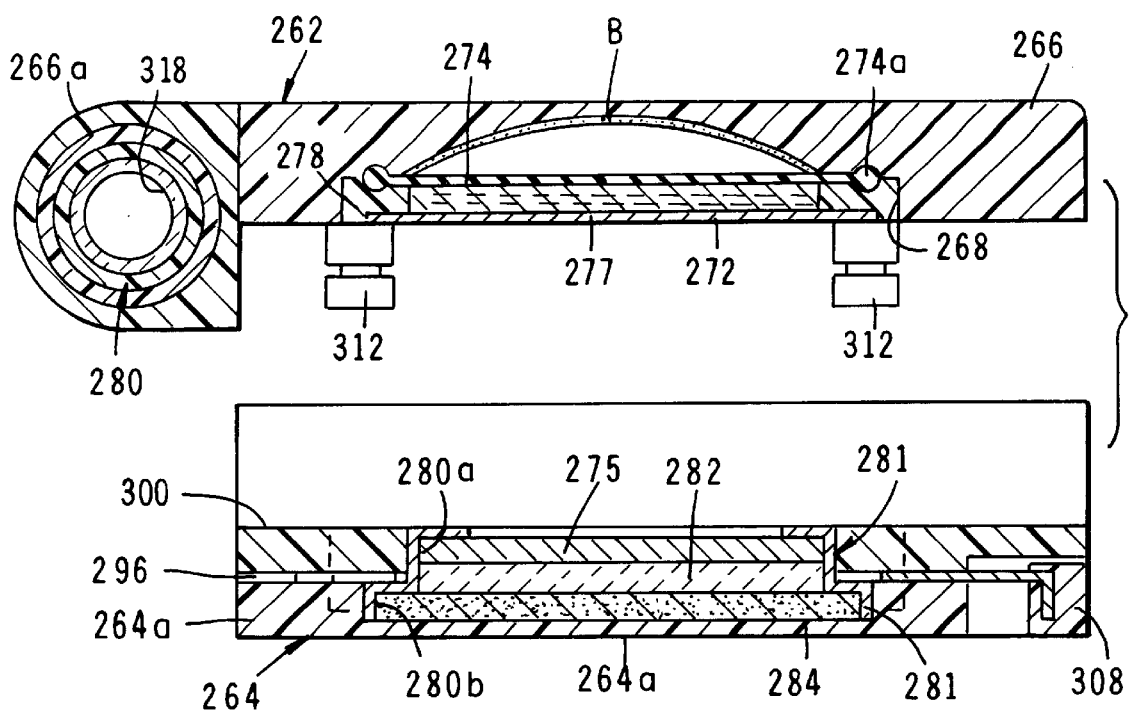
FIG. 51 is an exploded, cross-sectional view of the apparatus shown in FIG. 49.
Figure 52:
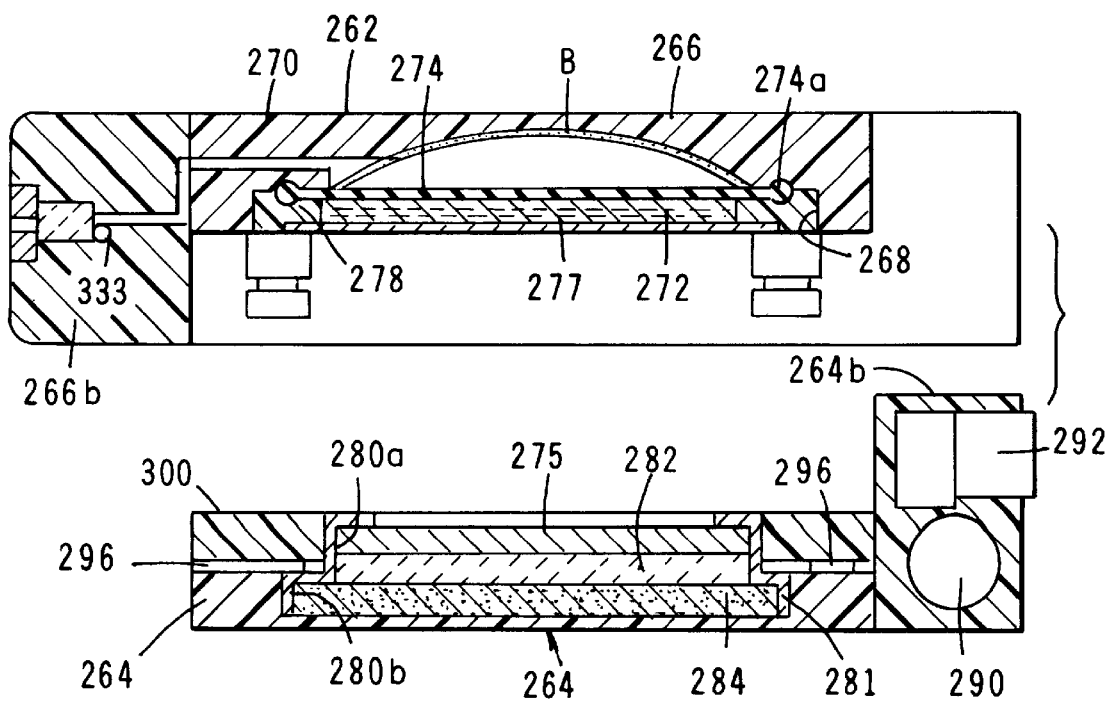
FIG. 52 is an exploded, cross-sectional view of the apparatus shown in FIG. 50.
Figure 56:
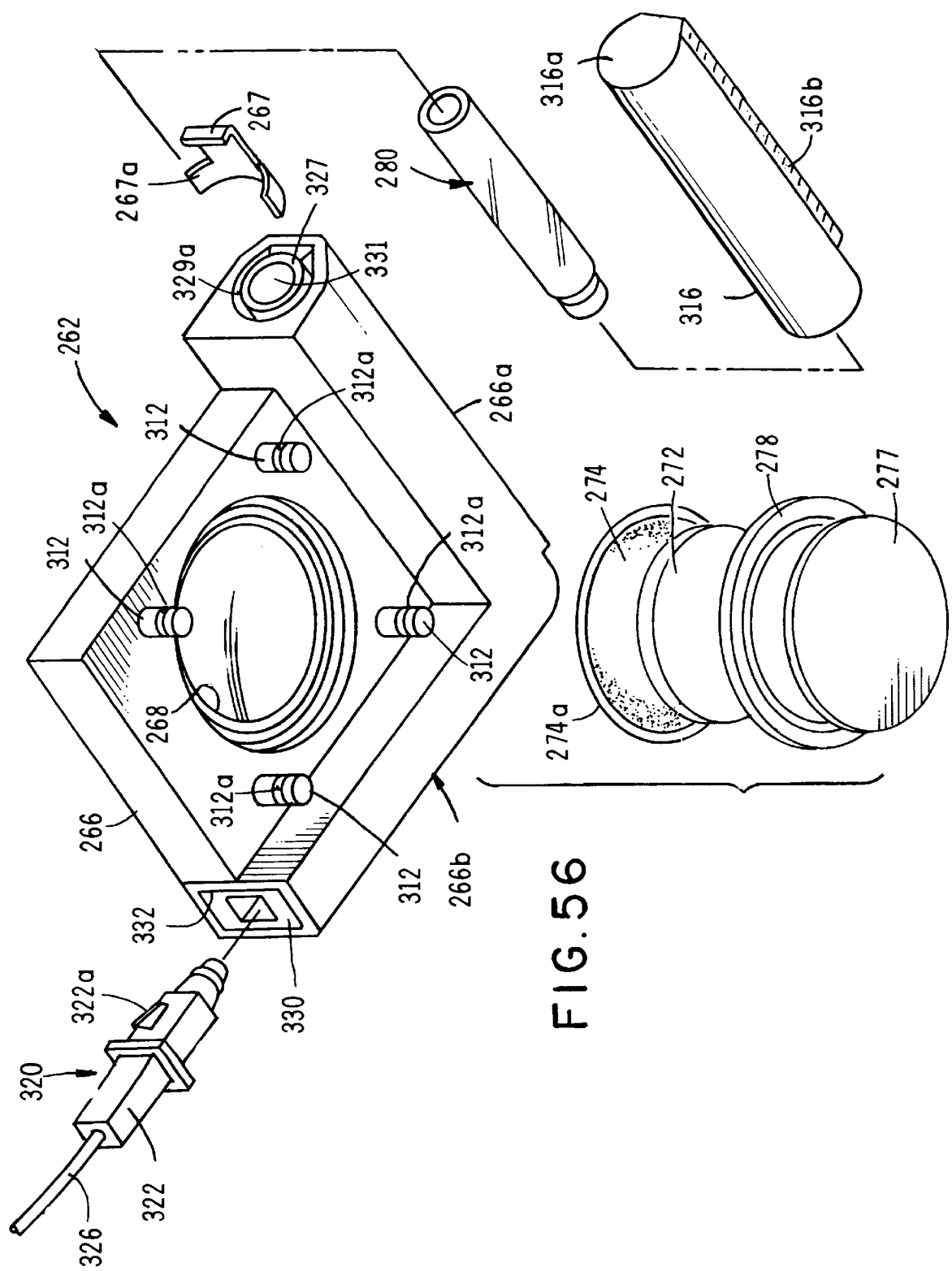
FIG. 56 is a generally perspective, bottom view of the fluid reservoir housing of the apparatus shown in FIG. 43.
Figure 57:
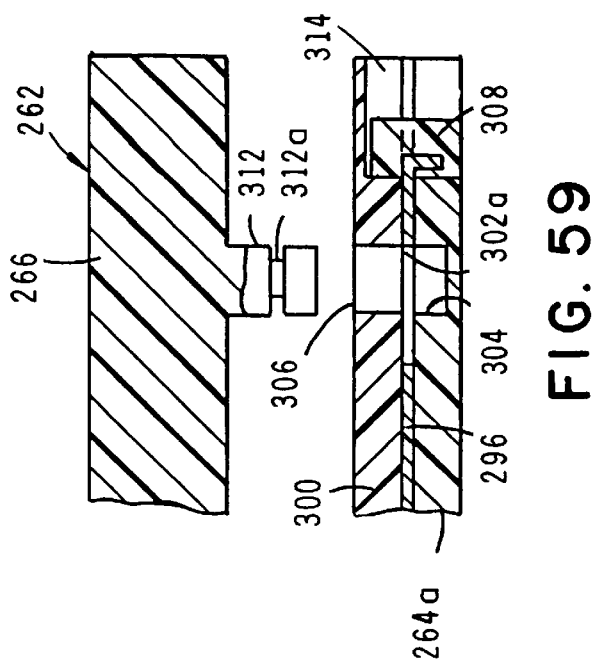
FIG. 57 is a generally perspective, fragmentary exploded view of the electronics housing and fluid reservoir housing portions of the apparatus shown in FIG. 43.

Referring next to FIGS. 43 through 60, still another form of the apparatus of the invention is there shown and generally designated by the numeral 260. This alternate embodiment is quite different from those previously described in that the heating means and the fluid housing are discrete components that can be snapped together to form the dispensing device of the invention. More particularly, as best seen in FIGS. 51 and 52, the apparatus here comprises a disposable upper reservoir component 262 and a re-usable lower electronics component 264. Referring also to FIG. 56, it can be seen that reservoir component 262 includes a cover 266 having a generally circular shaped chamber 268 which houses the heat-expandable means of the invention. As before, the heat expandable means functions to cause the fluids contained within the sealed reservoir of the device to flow outwardly through an outlet 270 formed in cover 266 (FIG. 43). The heat-expandable means is here provided in the form of a thermal expandable polymer mass 272 which is disposed within chamber 268 in the manner best seen in FIGS. 51 and 52. Once again expandable mass 272 can take several forms, but a particularly attractive form for devices of the present invention comprises a semisolid form such as a gel.

As in the earlier described embodiments, sealing means are superimposed over chamber 268. This sealing means here comprises a distendable membrane 274 having an O-ring like periphery 274a that is sealably connected to the peripheral portion of cover 266 in the manner shown in FIGS. 51 and 52. Membrane 274 cooperates with cover 266 to form a fluid reservoir that can be filled with the fluid to be dispensed by novel fill means of a character presently to be described. As mass 272 is heated by a heater coil 275, which is housed within lower electronics component 264, it will controllably expand from a compressed configuration to an expanded configuration and, in so doing, will experience a change in volume. With the construction of the device 260 shown in FIGS. 49 and 50, when the reservoir is filled heat expandable mass will be compressed by a gel barrier membrane 277 which spans chamber 268 and engages membrane 274. Then, as the heat expandable means is heated by the heating means of the invention, it will controllably expand against membrane 277 which will, in turn, act on the fluid which is contained within the reservoir in a manner to controllably force it outwardly thereof through outlet passageway 270 and into the infusion means of the apparatus, the details of construction which will presently be described.

As best seen in FIGS. 51, 52 and 55, the re-usable electronics component 264 includes a base member 264a and an electronics housing 264b, which is connected thereto. Base member 264a is apertured to receive a heater assembly frame 281 that is provided with a first chamber 280a. Chamber 280a houses heater coil 275 as well as a ceramic thermal barrier 282 that is supported by a conventional potting compound 284 that is contained within a second, lower chamber 280b formed in heater assembly frame 280.

Electronics housing 264b includes a chamber 288 which can be closed by a cover 289 and which houses the power supply, here provided as a high performance battery 290. Electronics housing 264b also houses the electronic control module 292 of the device, the character of which will presently be described. As will later be discussed, module 292 can be programmed by means of the electronic programming buttons 294 carried by housing 264b (FIG. 44).

Figure 43B:
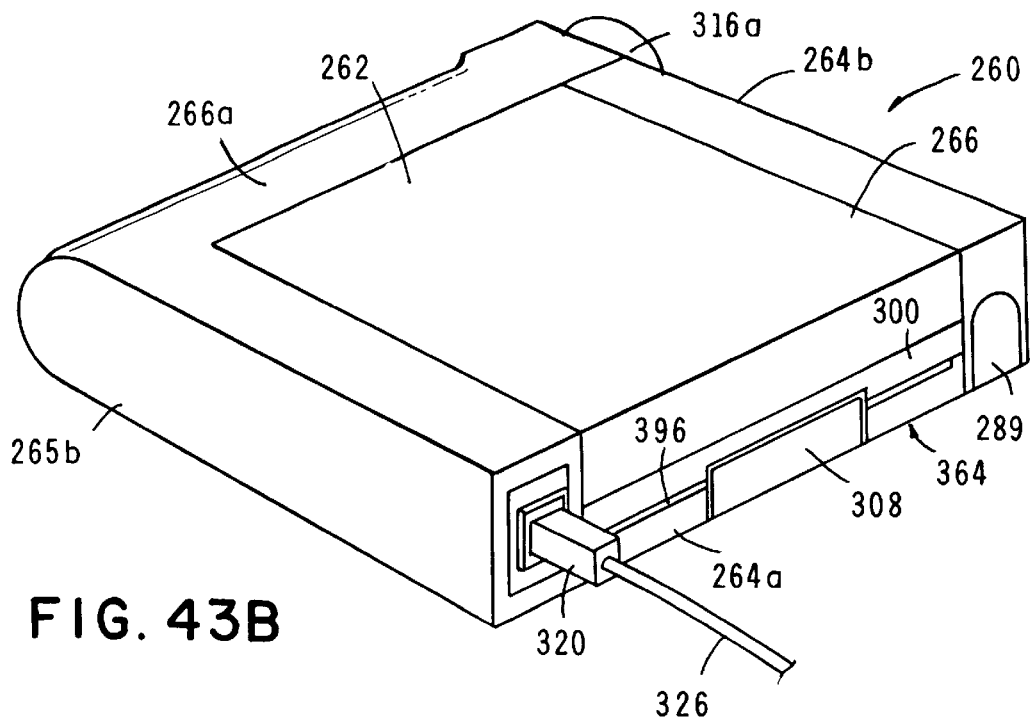
FIG. 43B is a generally perspective right-side view of the device shown in FIG. 43.
Figure 43C:
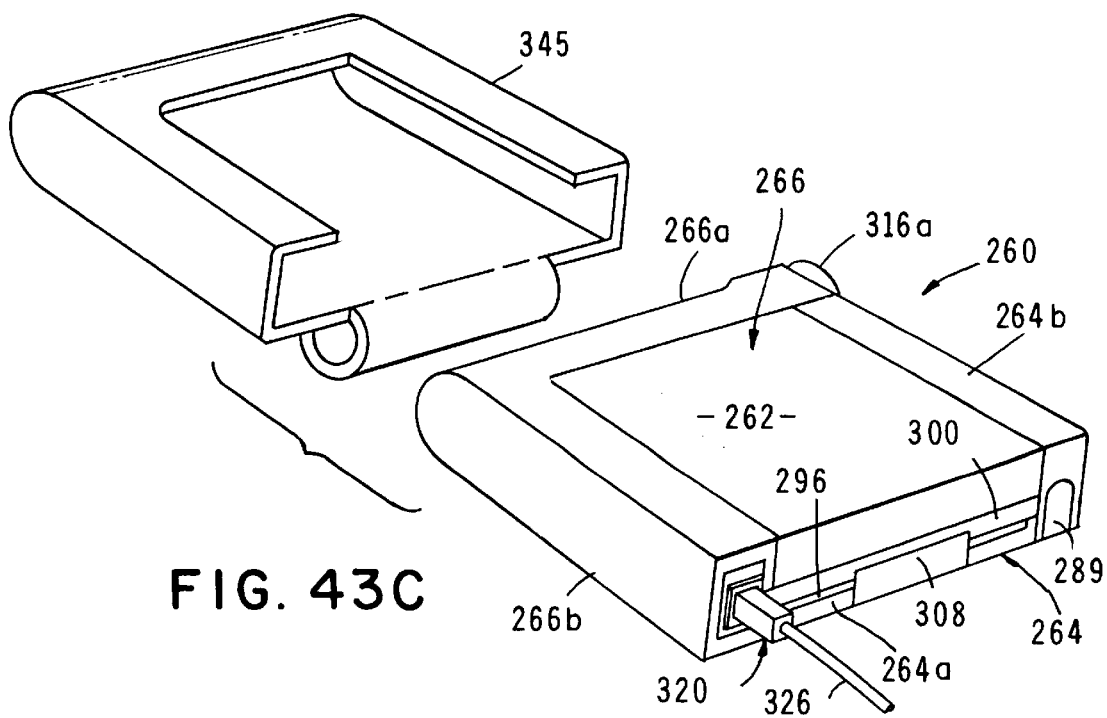
FIG. 43C is a generally perspective rear view of the device shown in FIG. 43 along with a generally perspective view of a belt clip for receiving the device to enable it to be affixed to the user's belt.
Figure 46:
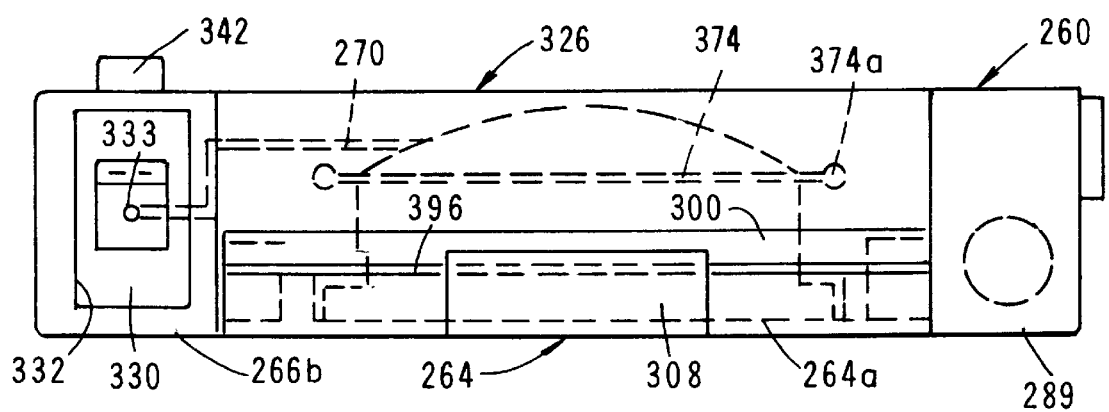
FIG. 46 is a right side elevational view of the device shown in FIG. 43.
Figure 59:
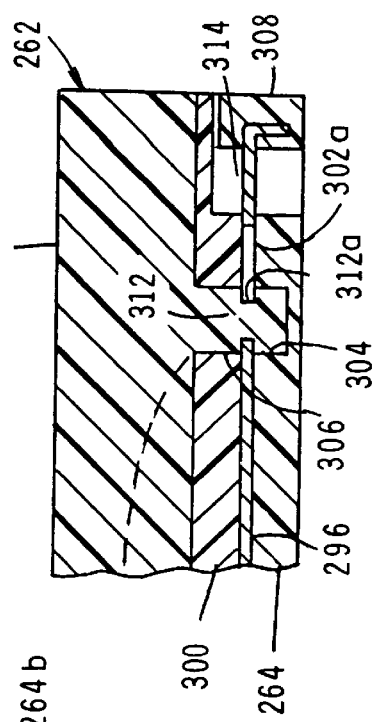
FIG. 59 is a fragmentary cross-sectional view showing the construction of the locking mechanism for connecting together the components shown in FIG. 57.
Figure 58:
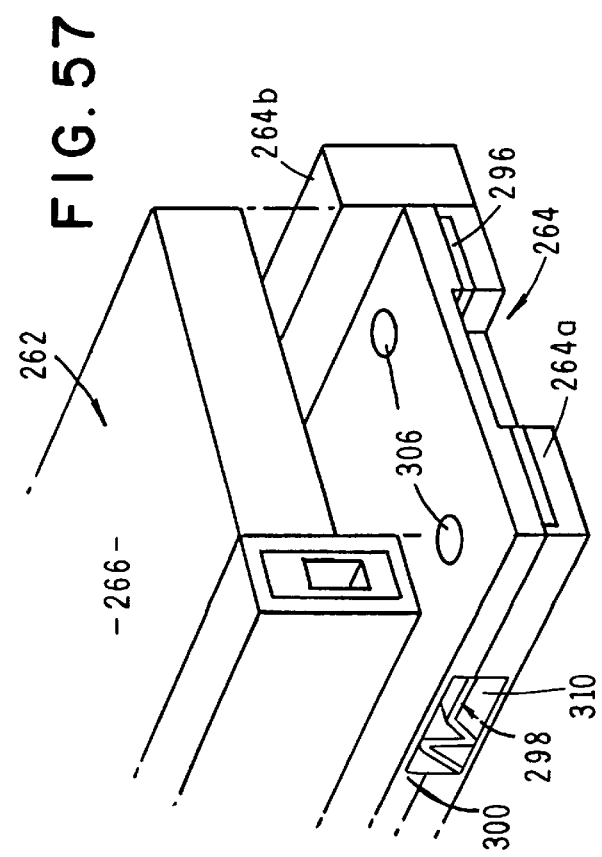
FIG. 58 is a generally perspective fragmentary view of the components shown in FIG. 57 as they appear in an assembled configuration.
Figure 60:
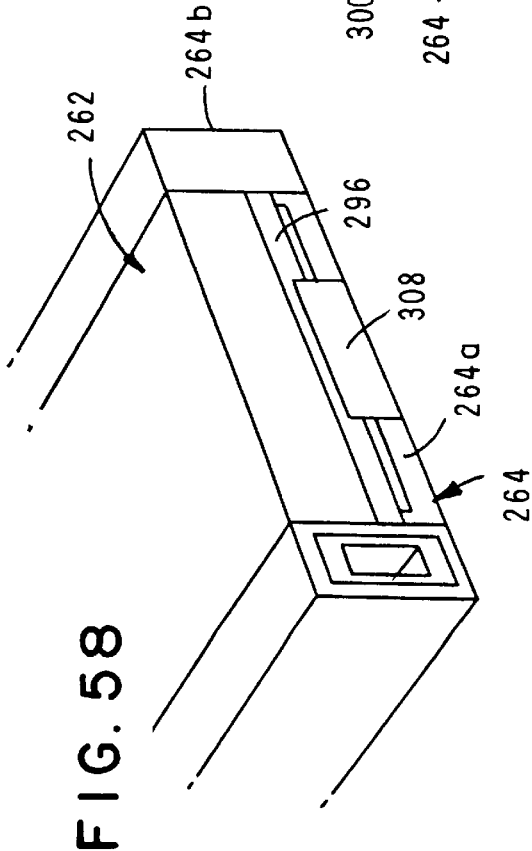
FIG. 60 is a fragmentary, cross-sectional view showing the components illustrated in FIG. 59 in an assembled configuration.

Superimposed over base member 264a is a locking plate 296, which comprises part of the component connector means of the invention, and which functions to releasably interconnect reservoir component 262 with electronics component 264 in the manner shown in FIGS. 43A and 43B. Locking plate 296, which includes opposed operating springs 298, the purpose of which will presently be described, is held in position by a retainer plate 300 which overlays base member 264a in the manner shown in FIGS. 51 and 52. As shown in FIG. 55, locking plate 296 includes a generally oval shaped central clearance opening 296a and four generally keyhole-shaped openings 302, each of which has an enlarged diameter portion 302a. Portions 302a can be moved into index with one of four bores 304 formed in base member 264a and with one of four apertures 306 formed in retainer plate 300 by pushing locking plate 296 inwardly against the urging of springs 298. More particularly, as illustrated in FIG. 59, by pushing inwardly on a push pad 308 provided at the edge of plate 296, the enlarged diameter portions 302a of keyhole-shaped openings 302 will move into index with bores 304 and with apertures 306. However, as shown in FIG. 60, when pressure on push pad 308 is released, springs 298, which are positioned within openings 310 of base member 264a, will urge locking plate 296 to the right as shown in FIG. 60, causing the neck portions 302b of openings 302 to move into index with bores 304 and apertures 306.

With the construction described in the preceding paragraph, when push pad 308 has been pushed inwardly into slot 314 of base member 264a (FIG. 59), connector pins 312 provided on the reservoir component can be freely inserted into apertures 306, past locking plate 296 and into bores 304 of base member 264a. Once the pins are fully seated within bore 304, a release of pressure on push pad 308 will cause springs 298 to urge locking plate 296 into the position shown in FIG. 60. In this position, the edges of the necked down portions 302b of the keyhole-shaped openings 302 will reside within grooves 312a formed in connector pins 312 thereby locking together reservoir component 262 and electronics component 264. When desired, the components can be separated by pushing inwardly on push pad 308 to move enlarged diameter portions 302a into index with bores 304 and apertures 306.

When the reservoir and electronic component 262 and 264 have been connected in the manner shown in FIGS. 43A, 43B, 49 and 50, energization of heater coil 275, in the manner previously described, will controllably expand mass 272 urging the fluid to be dispensed to the patient outwardly of the device reservoir which is formed by distendable membrane 274 upon filling the dispensing device using the reservoir fill means of the invention.

Figure 47:
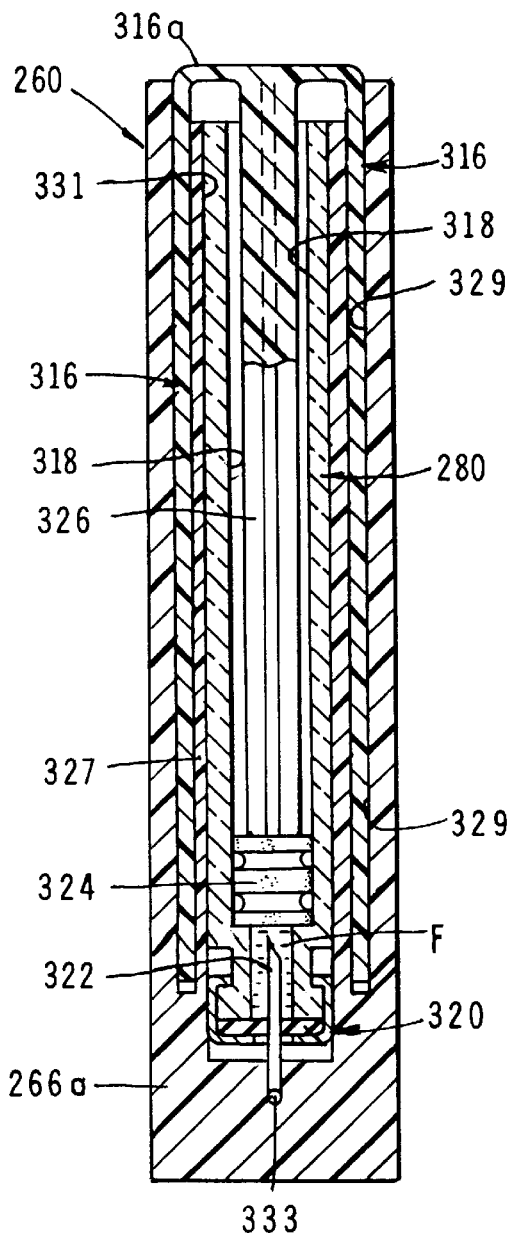
FIG. 47 is a cross-sectional view taken along lines 47—47 of FIG. 43.
Figure 48:
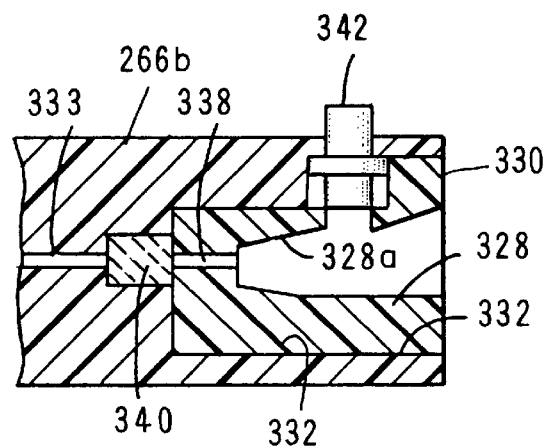
FIG. 48 is a cross-sectional view taken along lines 47—47 of FIG. 43.

Considering next the novel reservoir fill means of the invention, this means here comprises three major components, namely a side housing 266a connected to cover 262, the previously mentioned medicament vial cartridge or container assembly 280 and an adapter or pusher sleeve assembly 316 (FIGS. 47 and 56). Container assembly 280 contains the medicinal fluid with which the reservoir of the dispensing device is to be filled. As best seen in FIG. 47, container assembly 280 includes a chamber 318 having first and second open ends. The first open end is sealably closed by closure means, here provided in the form of septum assembly 320 which includes a pierceable septum and a clamping ring for connecting the septum to the container proximate the first open end. The septum of the septum assembly 320 is pierceable by a cannula means or cannula 322 which is carried by side housing 266a.

Referring next to FIGS. 49 through 52 it is to be noted that cover 266 may be constructed of a plastic material such as, for example, a polycarbonate, an acrylic polystyrene, polyvinylchloride, polyethylene, polyester, PMMA, polysulfone, polyurethane, polyinuide, polyvinylalcohol, polypropylene. With this construction, the interior surface of the cover 266 as well as fluid flow passageways which carry fluid to the infusion means can be surface modified or coated with various materials to form thin conformable, protective, interfacial barriers "B" for biological compatibility or to promote wetlubricity or wettability.

These barriers or surface treatments "B" can include hydrophilic agents that offer a wide range of wettability characteristics which can be tailored to meet the required surface wetting, priming, reduction of gas bubble adhesion, and other flow performance characteristics. Other forms of these coatings can also reduce the absorption and denaturation of other biomaterials, including proteins. Alternatively, modified proteins, peptides, carbohydrates and synthetic polymers can also be covalently bonded to surfaces to generate ultrathin coatings or crosslinked to generate other three dimensional intermediate polymer matrices to either inhibit other biochemical responses or for immobilization of related biomaterials. These coatings and surface modification treatments are readily available from multiple sources and well known to those skilled in the art.

To expel fluid from chamber 318 of the container assembly and into cannula 322 and thence into the fluid reservoir of the dispenser unit via passageways 333 and 270, displacement means are provided. This displacement means here comprises a plunger 324 which is telescopically movable within chamber 318 by pusher sleeve assembly 316. To accomplish this movement, pusher sleeve assembly 316 is provided with pusher means shown here as a pusher rod 326 which is integrally formed with end wall 316a of the pusher sleeve assembly (FIG. 47).

Referring particularly to FIGS. 47 and 56, it is to be noted that side housing 266a includes an inner, generally cylindrically shaped wall 327 which defines an elongated annular space 329 within which the pusher sleeve assembly 316 is slidably received. As shown in FIGS. 47 to 56, container assembly 280 is closely receivable within a chamber 331 formed internally of wall 327 and can be urged forwardly of chamber 331 by inward telescopic movement of the pusher sleeve assembly into annular space 329. More particularly, as indicated in FIG. 47, the inboard end of pusher rod 326 engages plunger 324 and urges it inwardly of chamber 318 as the pusher sleeve is moved inwardly of annular space 329.

During the initial mating of the pusher sleeve assembly and the container assembly with side housing 266a, the resistance of the fluid within chamber 318 will resist movement of plunger 324 inwardly of chamber 318 so as to cause the entire container assembly to initially move inwardly of chamber 331 to a position wherein the septum assembly 320 is engaged by cannula 322 of the side housing. A continued inward force on the pusher sleeve assembly will cause cannula 322 to pierce the septum in the manner shown in FIG. 47, thereby opening fluid communication between chamber 318 of the container assembly and the internal fluid passageway of cannula 322. Once the septum has been pierced, pusher rod 326 will urge plunger 324 forwardly of chamber 318 from a first location proximate the second open end to the second location shown in FIG. 47. As plunger 324 moves forwardly of chamber 318, fluid within the chamber will be caused to flow into the central fluid passageway of cannula 322 toward a passageway 333 formed in cover 266b and finally into the device reservoir via passageway 270 (FIG. 43).

It is to be noted that the pusher sleeve assembly includes a plurality of longitudinally spaced locking teeth 316b which are engaged by a locking tab 267 provided on a clip-like member 267a that is mounted within a space 329a. As the pusher sleeve assembly is urged into annular space 329a, tab 267 will ride over teeth 316b. However, teeth 316b are configured to prevent attempted removal of the pusher sleeve thereby preventing re-use of the fill means.

Following filling of the reservoir of the device with the fluid to be infused into the patient, the novel infusion means of the invention, which includes line connector 320, is connected to reservoir component 262 in the manner shown in FIGS. 43A and 43B. As indicated in FIG. 53, line connector 320 includes a body 322 having a fluid passageway 324 therethrough. Connected to the outboard end of passageway 324 is a conventional administration set delivery line 326. The forward portion of body 322 is sealably received within a tapered bore 328 formed in a connector block 330. Connector block 330 is, in turn, received within a cavity 332 formed in a second side housing 266b that is connected to cover 266. Cavity 332 is in communication with the reservoir of the device via passageways 333 and 270 (FIGS. 50 and 53). When connector block 330 is in position within cavity 332, passageway 333 is also in communication with passageway 338 formed in connector block 330 via the flow control means of the device. This flow control means here comprises a porous impedance frit 340 which functions to controllably impede or modulate fluid flow toward line 326 in the event of any unexpected environmental perterbation and during the reservoir filling step. Body 322 of line connector 320 further includes a resilient tab 322a which is engaged by a release button 342 that releasably secures the line connector in position within the connector block.

In operation of the apparatus of this latest embodiment of the invention, after the reservoir has been filled and the infusion means connected in the manner just described, the electronic controller and storage module of the device can be programmed to enable the precise delivery of basal, elevated basal, bolus and varying dosing volumes in response to either a physiological sensor of the character previously described or to a programmed delivery protocol. As was the case with the embodiment shown in FIGS. 35 through 38, the various delivery levels can be achieved by selectively varying the power supplied to the delivery heater as, for example, by changing the voltage or current levels, by changing the pulse width modulation of the applied power, or by changing the frequency, amplitude or pulse amplitude modulation of the applied power. The electronic controller can also be programmed to indicate function status to the user and to detect the highly unlikely event of a thermal runaway failure of the heater. The user will be notified of any heater malfunction by the audio alarm or audible horn 23 (see FIG. 61).

Figure 61:
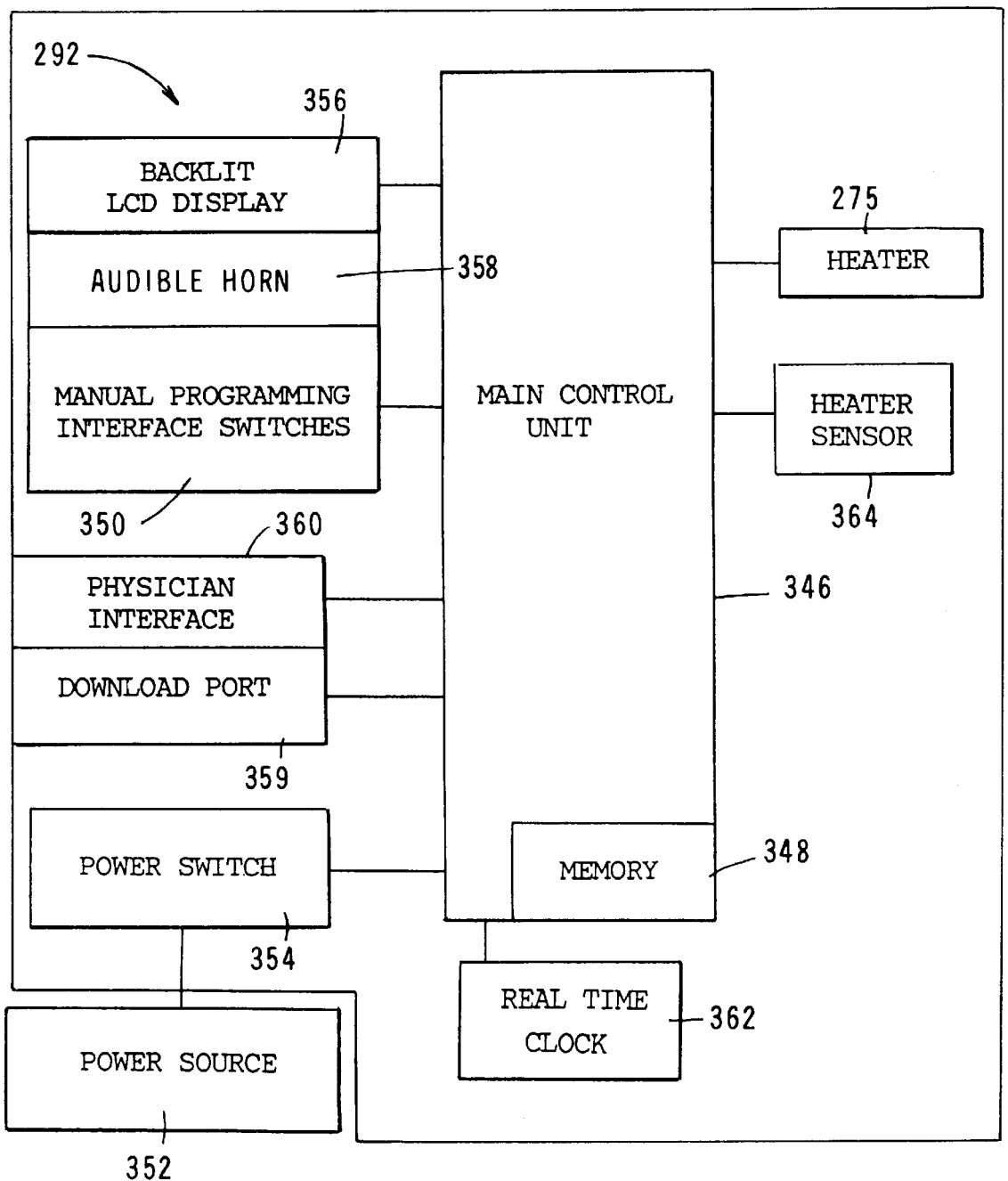
FIG. 61 is a generally diagrammatic view showing the various components of the controller and stimulation means of this latest embodiment of the invention.

Referring particularly to FIG. 61, it can be seen that the electronic controller module 292 comprises a main control unit 346 having a memory 348, manual programming interface switches 350, a conventional power source 352 and a power switch 354. Connected to main control unit 346 is a data display shown here as a backlit LCD display 356 and an audible horn 358. Also connected to main control unit 346 is a download port 359, a physician's interface 360 and a real time clock 362. Additionally, the main control unit is connected to the heater or heater coil 275 and to a heat sensor 364 in the manner shown in FIG. 61. After the electronic controller and storage means are initially programmed, programming buttons 299 (FIG. 44), which are operably associated with switches 350, can be used to select a different delivery schedule. If desired, once the unit is programmed, the controller can be locked using the physician's interface thereby preventing any changes to the settings by an unauthorized person. It is to be understood that electronic controller 292, as well as the earlier described controller 202 can readily be programmed by one skilled in the art to perform the aforementioned functions as well as other functions that may be desired by the physician.

While the unit is operating, data display 356 will display information concerning the current basal and bolus settings, total drug amount delivery, time or dosage remaining or other information determined to be needed such as battery charge level and the like. Physiological sensor information from sensors of the character previously identified can also be displayed, and downloaded to a compatible system to allow analysis of the physiological sensor date at a later time. After the device has been programmed, it can be inserted into a belt clip 345 of the character shown in FIG. 43c and then attached to the user's belt.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claimed is:

1. A device for use in infusing medicinal fluid into a patient at a controlled rate comprising:
   (a) a housing having a surface and including a base and a cover superimposed over said base;
   (b) distendable means for forming, in conjunction with said surface of said housing, a fluid reservoir having an inlet and an outlet, said distendable means comprising at least one distendable membrane at least a portion of which is movable within said housing from a first position to a second position;
   (c) expandable means disposed within said housing in proximity to said distendable membrane, said expandable means comprising a semi-solid, which, upon being stimulated, will act upon said distendable membrane to move said membrane toward said second position to cause fluid within said reservoir to flow outwardly of said outlet of said reservoir;
   (d) stimulation means for stimulating said expandable means; and
   (e) infusion means in communication with said outlet of said reservoir for infusing fluid from said fluid reservoir into the patient.

2. The device as defined in claim 1 in which said infusion means comprises a hollow cannula connected to said base and extending therefrom.

3. The device as defined in claim 1 in which said infusion means comprises a hollow cannula connected to, but spaced apart from said housing.

4. The device as defined in claim 1 in which said expandable means comprises a gel.

5. The device as defined in claim 1 in which said stimulation means comprises a heat source operably associated with said expandable means.

6. The device as defined in claim 1 further including fill means for filling said reservoir.

7. The device as defined in claim 1 in which said base and said cover are releasably interconnected.

8. The device as defined in claim 7 in which said distendable means is disposed within said cover and in which said stimulation means is disposed within said base.

9. The device as defined in claim 8 in which said expandable means is disposed within said cover.

10. A device for use in infusing medicinal fluid into a patient at a controlled rate comprising:
    (a) A housing having a surface and including a base and a cover superimposed over said base;
    (b) distendable means for forming, in conjunction with said surface of said housing, a fluid reservoir having an inlet and an outlet, said distendable means comprising at least one distendable membrane at least a portion of which is movable within said housing from a first position to a second position;
    (c) expandable means disposed within said housing in proximity to said distendable membrane, said expandable means comprising a semi-solid, which, upon being heated, will act upon said distendable membrane to move said membrane toward said second position to cause fluid within said reservoir to flow outwardly of said outlet of said reservoir;
    (d) heating means for stimulating said expandable means, said heating means comprising an electrically operated heating coil;
    (e) infusion means in communication with said outlet of said reservoir for infusing fluid from said fluid reservoir into the patient; and
    (f) fill means for filling said reservoir.

11. The device as defined in claim 10 in which said infusion means comprises a hollow cannula.

12. The device as defined in claim 10 in which said expandable means comprises a gel.

13. The device as defined in claim 10 in which said base and said cover are releasably interconnected.

14. The device as defined in claim 13 in which said distendable means is disposed within said cover and in which said stimulation means is disposed within said base.

15. The device as defined in claim 14 in which said expandable means is disposed within said cover.

16. A device for use in infusing medicinal fluid into a patient at a controlled rate comprising:
    (a) a housing having a surface and including a base and a cover superimposed over said base, said cover having an internal surface;
    (b) distendable means for forming, in conjunction with said surface of said housing, a fluid reservoir having an inlet and an outlet, said distendable means comprising at least one distendable membrane at least a portion of which is movable within said housing from a first position to a second position;
    (c) fill means for filling said fluid reservoir;
    (d) expandable means disposed within said housing in proximity to said distendable membrane, said expandable means comprising a gel which, upon being heated, will act upon said distendable membrane to move said membrane toward said second position to cause fluid within said reservoir to flow outwardly of said outlet of said reservoir;
    (e) heating means for heating said gel; and
    (f) infusion means in communication with said outlet of said reservoir for infusing fluid from said fluid reservoir into the patient.

17. The apparatus as defined in claim 16 in which the interior surface of said cover is modified to provide a protective barrier.

18. The apparatus as defined in claim 16 in which the interior surface of said cover is modified to provide wetlubricity.

19. The apparatus as defined in claim 16 in which the interior surface of said cover is modified to provide wettability.

20. The apparatus as defined in claim 16 in which the interior surface of said cover is modified to provide biological compatibility.

21. The apparatus as defined in claim 16 in which the interior surface of said cover is modified to provide an intermediate polymer matrix for immobilization of biomaterials.

22. A device for use in infusing medicinal fluid into a patient at a controlled rate comprising:

(a) a housing having a surface and including a base and a cover superimposed over said base;

(b) distendable means for forming, in conjunction with said surface of said housing, a fluid reservoir having an inlet and an outlet, said distendable means comprising at least one distendable membrane at least a portion of which is movable within said housing from a first position to a second position;

(c) expandable means disposed within said housing in proximity to said distendable membrane, said expandable means comprising a semi-solid, which, upon being stimulated, will act upon said distendable membrane to move said membrane toward said second position to cause fluid within said reservoir to flow outwardly of said outlet of said reservoir;

(d) stimulation means for stimulating said expandable means; and (e) sensor means operably associated with said stimulation means for sensing metabolic condition of the patient; and (f) infusion means in communication with said outlet of said reservoir for infusing fluid from said fluid reservoir into the patient.

23. The device as defined in claim 22 further including controller means operably associated with said sensor means and said stimulation means for controlling said stimulation means.

24. The device as defined in claim 23 in which said stimulation means comprises a heating means for heating said expandable means.

25. The device as defined in claim 24 in which said expandable means comprises a gel.

* * * * *